(12) United States Patent
Chyu et al.

(10) Patent No.: US 9,205,141 B2
(45) Date of Patent: Dec. 8, 2015

(54) IMMUNOMODULATORY METHODS AND SYSTEMS FOR TREATMENT AND/OR PREVENTION OF HYPERTENSION

(75) Inventors: Kuang-Yuh Chyu, Los Angeles, CA (US); Prediman K. Shah, Los Angeles, CA (US)

(73) Assignee: Cardio Vax, LLC, Torrance, CA (US)

( * ) Notice: Subject to any disclaimer, the term of this patent is extended or adjusted under 35 U.S.C. 154(b) by 27 days.

(21) Appl. No.: 13/884,911

(22) PCT Filed: Nov. 11, 2011

(86) PCT No.: PCT/US2011/060482
§ 371 (c)(1),
(2), (4) Date: May 10, 2013

(87) PCT Pub. No.: WO2012/074725
PCT Pub. Date: Jun. 7, 2012

(65) Prior Publication Data
US 2013/0230487 A1    Sep. 5, 2013

Related U.S. Application Data

(60) Provisional application No. 61/413,375, filed on Nov. 12, 2010.

(51) Int. Cl.

| | |
|---|---|
| *A61K 38/04* | (2006.01) |
| *A61K 38/10* | (2006.01) |
| *A61K 38/18* | (2006.01) |
| *A61K 38/19* | (2006.01) |
| *A61K 38/20* | (2006.01) |
| *A61K 39/395* | (2006.01) |
| *C12N 5/0783* | (2010.01) |
| *A61K 39/00* | (2006.01) |
| *C07K 7/04* | (2006.01) |
| *C07K 7/08* | (2006.01) |
| *C07K 14/495* | (2006.01) |
| *C07K 14/54* | (2006.01) |
| *C07K 14/775* | (2006.01) |
| *C07K 14/55* | (2006.01) |
| *C07K 16/24* | (2006.01) |

(52) U.S. Cl.
CPC .............. *A61K 39/0012* (2013.01); *A61K 38/10* (2013.01); *A61K 38/1841* (2013.01); *A61K 38/208* (2013.01); *A61K 38/2013* (2013.01); *A61K 38/2026* (2013.01); *A61K 38/2066* (2013.01); *A61K 38/2086* (2013.01); *A61K 39/0005* (2013.01); *A61K 38/04* (2013.01); *A61K 39/3955* (2013.01); *A61K 2039/5158* (2013.01); *A61K 2039/55505* (2013.01); *C07K 7/08* (2013.01); *C07K 14/495* (2013.01); *C07K 14/5406* (2013.01); *C07K 14/5428* (2013.01); *C07K 14/5443* (2013.01); *C07K 14/5446* (2013.01); *C07K 14/55* (2013.01); *C07K 14/775* (2013.01); *C07K 16/246* (2013.01); *C12N 5/0636* (2013.01)

(58) Field of Classification Search
None
See application file for complete search history.

(56) References Cited

U.S. PATENT DOCUMENTS

| | | | |
|---|---|---|---|
| 4,970,144 | A | 11/1990 | Fareed et al. |
| 5,223,426 | A | 6/1993 | Skibbens et al. |
| 5,408,038 | A | 4/1995 | Smith et al. |
| 5,766,947 | A | 6/1998 | Rittershaus et al. |
| 5,827,516 | A | 10/1998 | Urban et al. |
| 5,861,276 | A | 1/1999 | Kwak et al. |
| 5,972,890 | A | 10/1999 | Lees et al. |
| 6,156,315 | A | 12/2000 | Goldberg et al. |
| 6,635,623 | B1 | 10/2003 | Guevara et al. |
| 6,727,102 | B1 | 4/2004 | Holvoet et al. |
| 7,527,795 | B2 | 5/2009 | Nilsson et al. |
| 7,528,225 | B2 | 5/2009 | Nilsson et al. |
| 7,537,758 | B2 | 5/2009 | Nilsson et al. |
| 7,544,360 | B2 | 6/2009 | Nilsson et al. |
| 7,556,811 | B2 | 7/2009 | Nilsson et al. |
| 7,704,499 | B2 | 4/2010 | Nilsson et al. |
| 7,785,589 | B2 | 8/2010 | Nilsson et al. |
| 8,025,876 | B2 | 9/2011 | Nilsson et al. |
| 8,029,786 | B2 | 10/2011 | Nilsson et al. |
| 8,034,336 | B2 | 10/2011 | Nilsson et al. |
| RE43,581 | E | 8/2012 | Nilsson et al. |
| 9,125,850 | B2 * | 9/2015 | Chyu ................. A61K 39/0012 |
| 2002/0150891 | A1 | 10/2002 | Hood et al. |
| 2003/0105003 | A1 | 6/2003 | Nilsson et al. |
| 2003/0157113 | A1 | 8/2003 | Terman |
| 2003/0165819 | A1 | 9/2003 | McGowan et al. |
| 2004/0002111 | A1 | 1/2004 | Hansson et al. |
| 2004/0101874 | A1 | 5/2004 | Ghosh et al. |

(Continued)

FOREIGN PATENT DOCUMENTS

| | | |
|---|---|---|
| EP | 911344 | 4/1999 |
| EP | 1186299 | 3/2002 |

(Continued)

OTHER PUBLICATIONS

Tokuriki et al. Stability effects of mutations and protein evolvability. Current Opinion in Structural Biology 19: 596-604, 2009.*
Robertson et al. T cells in Atherogenesis for Better or for worse? Arterioscler Thromb Vasc Biol 26: 2421-2432, 2006.*
Bork et al., "Go hunting in sequence databases but watch out for the traps." Trends in Genetics, 1996, vol. 12, No. 10, pp. 425-427.
Bork, Peer. "Powers and Pitfalls in Sequence Analysis: The 70% Hurdle." Genome Research, vol. 10; pp: 398-400.

(Continued)

*Primary Examiner* — Bridget E Bunner
(74) *Attorney, Agent, or Firm* — Nixon Peabody LLP; Seth Levy; Hema Vakharia-Rao

(57) ABSTRACT

Immunomodulatory agents, T cell, compositions, methods and systems for treating and/or preventing hypertension and/or a condition associated thereto in an individual.

8 Claims, 16 Drawing Sheets

(56) References Cited

U.S. PATENT DOCUMENTS

| | | | |
|---|---|---|---|
| 2005/0152900 | A1 | 7/2005 | Najib et al. |
| 2005/0260222 | A1 | 11/2005 | Gupta et al. |
| 2006/0018929 | A1 | 1/2006 | Zaia et al. |
| 2006/0233817 | A1 | 10/2006 | Hansson |
| 2007/0098725 | A1* | 5/2007 | Nilsson et al. ............ 424/145.1 |
| 2008/0070265 | A1 | 3/2008 | Hansson |
| 2008/0311140 | A1 | 12/2008 | Lee |
| 2009/0092618 | A1 | 4/2009 | Hansson |
| 2009/0117137 | A1 | 5/2009 | Nilsson et al. |
| 2009/0208503 | A1* | 8/2009 | Carlsson et al. ........... 424/135.1 |
| 2009/0215697 | A1* | 8/2009 | Tedgui et al. .................. 514/13 |
| 2009/0226475 | A1 | 9/2009 | Nilsson et al. |
| 2010/0183706 | A1 | 7/2010 | Nilsson et al. |
| 2011/0300172 | A1 | 12/2011 | Nilsson et al. |
| 2012/0251513 | A1 | 10/2012 | Hansson |
| 2012/0311729 | A1 | 12/2012 | Chyu |
| 2013/0236418 | A1 | 9/2013 | Shah |

FOREIGN PATENT DOCUMENTS

| | | |
|---|---|---|
| EP | 1394177 | 3/2004 |
| EP | 1676602 A1 | 7/2006 |
| WO | 93/18067 | 9/1993 |
| WO | 94/00592 | 1/1994 |
| WO | 94/05801 A1 | 3/1994 |
| WO | 97/43331 | 11/1997 |
| WO | 98/13385 | 4/1998 |
| WO | 98/42751 | 10/1998 |
| WO | 98/56938 | 12/1998 |
| WO | 99/08109 | 2/1999 |
| WO | 99/46598 | 3/1999 |
| WO | 99/18986 | 4/1999 |
| WO | 99/31227 A2 | 6/1999 |
| WO | 00/02920 | 1/2000 |
| WO | 01/23414 A2 | 4/2001 |
| WO | 01/32070 | 5/2001 |
| WO | 01/57274 | 8/2001 |
| WO | 01/64008 | 9/2001 |
| WO | 01/68119 | 9/2001 |
| WO | 02/06314 | 1/2002 |
| WO | 02/42426 | 5/2002 |
| WO | 02/48388 | 6/2002 |
| WO | 02/080594 A1 | 10/2002 |
| WO | 02/080954 | 10/2002 |
| WO | 03/007689 | 1/2003 |
| WO | 2004/030698 A1 | 4/2004 |
| WO | 2007/116409 A2 | 10/2007 |
| WO | 2008/055354 A1 | 5/2008 |
| WO | 2011/033090 A1 | 3/2011 |
| WO | 2011/060329 A1 | 5/2011 |
| WO | 2011/095628 A1 | 8/2011 |
| WO | 2012/065133 | 5/2012 |
| WO | 2012/065133 A1 | 5/2012 |
| WO | 2012/065135 | 5/2012 |
| WO | 2012/074725 A2 | 6/2012 |

OTHER PUBLICATIONS

Brenner, Steven E. "Errors in genome annotation." Trends in Genetics, Apr. 1999, vol. 15, No. 4, pp. 132-133.

Doerks, et al., "Protein annotation: detective work for function prediction." Genetwork, 1998, 14(6):248-50.

Office Action for Chinese Patent Application No. 201180064978.9, 11 pages, Sep. 1, 2014.

Chyu et al., "Choking off plaque neovascularity: a promising atheroprotective strategy or a double edged sword?" Arteriosclerosis, Thrombosis, and Vascular Biology, May 2007, vol. 27(5), pp. 993-995.

Chyu et al., CD8 T cells mediate the athero-protective effect of immunization with an ApoB-100 peptide. PLOS One, vol. 7, No. 2, p. E30780 (2012).

Fredrickson et al., "Identification of immune responses against aldehyde-modified peptide sequences in apoB associated with cardiovascular disease." Arteriosclerosis Thrombosis and Vascular Biology, vol. 23(5), May 2003, pp. 872-878.

Fredrickson et al., Treatment with apo B peptide vaccines inhibits atherosclerosis in human apo B-100 transgenic mice without inducing an increase in peptide-specific antibodies. Journal of Internal Medicine, vol. 264, No. 6, pp. 563-570 (2008).

Fredrickson et al.,"Inhibition of atherosclerosis in apoE-null mice by immunization with apoB-100 peptide sequences." Arteriosclerosis, Thrombosis, Vascular Biology, Highwire Press, Philadelphia, PA, US, vol. 23(5), May 1, 2003, pp. 879-884.

Herbin et al.,"Continuous subcutaneous delivery of apolipoprotein B-derived peptides induces T cells anergy and reduces the progression of established atheroscelorsis in mice." Circulation, vol. 116(16), Suppl. S., Oct. 2007, p. 145.

Johnsen et al., Atherosclerosis in abdominal aortic aneurysms: a casual event or a process running in parallel? The Tromso study. Arteriosclerosis, Thrombosis, and Vascular Biology, vol. 30, No. 6, pp. 1263-1268 (2010).

Klingenberg et al., Intranasal immunization with an apolipoprotein B-100 fusion protein induces antigen-specifc regulatory T cells and reduces atherosclerosis. Arteriosclerosis, Thrombosis, and Vascular Biology, vol. 30, No. 5, pp. 946-975 (2010).

Ll et al., "Effects of rapamycin-treated HSP60-pulsed dendritic cells on progression of atherosclerotic plaque in mice." Zhongguo Bingli Shengli Zazhi (2006), 22(6), 1079-1082, Peop. Rep. China.

Miyake et al., Pharmacological treatment of abdominal aortic aneurysm. Cardiovascular Research, vol. 83, No. 3, pp. 436-443 (2009).

Nilsson et al., "Vaccines modulating lipoprotein autoimmunity as a possible future therapy for cardiovascular disease." Journal of Internal Medicine, vol. 266(3), Jun. 25, 2009, pp. 221-231.

Steinman et al., Tolerogenic dendritic cells. Annual Review of Immunology, vol. 21 (2003) pp. 685-711.

Wigren et al., Evidence for a role of regulatory T cells in mediating the atheroprotective effect of apolipoprotein B peptide vaccine. Journal of Internal Medicine, vol. 269, No. 5, pp. 546-556 (2010).

Yang et al., "Generation of HSP60-specific regulatory T cell and effect on atherosclerosis." Cellular Immunology, vol. 243, 2006, pp. 90-95.

Zhao et al., "Athero-protective Effects of Immunization with apo-B 100 Related Peptide Vaccine in apoE−/− Mice is Associated with Enhanced CD8 Regulatory T Cell Response." Circulation, vol. 120(18), Suppl. 2., Nov. 3, 2009, p. S1018.

International Search Report and Written Opinion for PCT International Application No. PCT/US2011/060480 filed on Nov. 11, 2011.

Skolnick et al., "From genes to protein structure and function: novel applications of computational approaches in the genomic era." Trends in Biotech, Jan. 2000, vol. 18; pp. 34-39.

Smith et al., "The challenges of genomes sequence annotation of the devil is in the details." Nature Biotech, Nov. 1997, vol. 15, pp. 1222-1223.

Wells, J. "Additivity of mutational effects in proteins." Biochemistry 1990, 29: 8509-8517.

Alving, C., et al., "Immunization with cholesterol-rich liposomes induces anti-cholesterol antibodies and reduces diet-induced hypercholesterolemia and plaque formation." J. Lab Clin. Med. 1996, 127: 40-49.

Ameli, S., et al., "Effect of immunization with homologous LDL and oxidized LDL on early atherosclerosis in hypercholesterolemic rabbits." Arteriosclerosis, Thrombosis and Vascular Biology 1996, 16: 1074-1079.

Ballow et al., "Immunomodulation and Immunotherapy." JAMA, Dec. 1997, vol. 278, No. 22, pp. 2008-2017.

Bancells, C., et al., "Immunological analysis of the electronegative LDL subfraction shows that abnormal n-terminal apolipoprotein B conformation is involved in increased binding to proteoglycans." The American Society for Biochemistry and Molecular Biology 2010, 1-16.

Beyar, R. "Controlling ischemic cardiovascular disease: from basic mechanisms to clinical managment." Ann N.Y. Acad Sci 1123: 232-236, 2008.

Binder, C., et al., "The role of natural anitbodies in atherogenesis." Journal of Lipid Research 2005, 46: 1353-1363.

(56) References Cited

OTHER PUBLICATIONS

Binder, C., et al., "Innate and acquired immunity in atherogenesis." Nature Medicine 2002; 8: 1218-1226.
Bork, Peer. "Powers and Pitfalls in Sequence Analysis: The 70% Hurdle." Genome Research, vol. 10; pp. 398-400. 2000.
Bourassa, P., et al., "Estrogen reduces atherosclerotic lesion development in apolipoprotein E-deficient mice." PNAS 1996, 93: 10022-10027.
Brown, J., et al., "A hypothetical model of the foreign antigen binding site of class II histocompatibility molecules." Nature 1988, 332: 845-850.
Brown et al., "A vaccine against atherosclerosis." Drug Discovery Today. 7(11):588-590, 2002.
Caligiuri, G., et al. "Interleukin-10 deficiency increases atherosclerosis, thrombosis, and Low-density Lipoproteins in apolipoprotein E knockout mice." Molecular Medicine 2003, 10-17.
Caligiuri, G., et al., Protective immunity against atherosclerosis carried by B cells of hypercholesterolemic mice. The Journal of Clinical Investigation, 2002, 109: 745-753.
Chatterton et al., "Immunoelectron microscopy of low density lipoproteins yields a ribbons and bow model for the conformation of apolipoprotein B on the lipoprotein surface." J Lipid Res 36: 2027-2037, 1995.
Chauhan, V., et al., "Evidence of lipid-dependent structural changes in specific domains of Apolipoprotein B100." Biochemistry 1998, 37: 3735-3742.
Chehin et al., "Early stages of LDL oxidation: apolipoprotein B structural changes monitored by infrared spectroscopy." J Lipid Res 42: 778-782, 2001.
Chen, San Hwan, "The Complete cDNA and Amino Acid Sequence of Human Apolipoprotein B-100" Journal of Biological Chemistry (1986), 261(28), 12918-21.
Chen et al. "Primary sequence mapping of human apolipoprotein B-100 epitopes comparisons of trypsin accessibility and immunoreactivity and implication for apoB conformation" Eur. J. Biochem. 175, 111-118 (1988).
Chen, S., et al., "Apolipoprotein B-48 is the product of a messenger RNA with organ-specific in frame stop codon." Science 1987, 238: 363-366.
Chobanian, AV., et al., "Antiatherogenic effect of captopril in the Watanave heritable hyperlipidemic rabbit." Hypertension, 1990, 15: 327-331.
Chyu, K., et al., "Immunization using Apo B-100 related epitope reduces atherosclerosis and plaque inflammation in hypercholesterolemic apo E (−/−) mice." Biochemical and Biophysical Research Communications 2005, 338: 1982-1989.
Crawford, M.H., "Chronic Ischemic Heart Disease" in Current Diagnosis and Treatment in Cardiology 2003:The McGraw-Hill Companies, Inc., Ch. 3 pp. 31-32.
Cucchiara, B., et al., "Atherosclerotic risk factors in patients with Ischemic Cerebrovascular Disease." Current Treatment Options in Neurology 2002, 40: 445.
Daniel et al., "Mapping of linear antigenic sites on the S glycoprotein of a neutropenic murine coronavirus with synthetic peptides: a combination of nine prediction algorithms fails to identify relevant epitopes and peptide immunogenicity is drastically influenced by the nature of the protein carrier" Virology 202: 540-549, 1994.
Du, X., et al., "Identification of two regions in Apolipoprotein B100 that are exposed on the cytosolic side of the endoplasmic reticulum membrane." Journal of Cell Biology, 1998, 141: 585-599.
Dunning, A., et al., "Association between epitopes detected by monoclonal antibody BIP-45 and the XbaI polymorphism of Apolipoprotein B." Clinical Genetics 1988, 33: 181-188.
Ehara, S., et al., "Elevated levels of oxidized low density lipoprotein show a positive relationship with the severity of acute coronary syndromes." Circulation 2001, 103: 1955-1960.
Fantappie, S., et al., "Monoclonal antibodies to human low density lipoprotein identify distinct areas of apolipoprotein lipoprotein-receptor interaction." Journal of Lipid Research 1992, 33: 1111-1121.
Fong L. G. et al., "Nonenzymatic oxidative cleavage of peptide bonds in apoprotein B-100." Journal of Lipid Research 1987, 28(12): 1466-1477.
Fredrikson, G., et al., "Atheroprotective immunization with MDA-modified apo B-100 peptide sequence is associated with activation of Th2 specific antibody expression." Autoimmunity 2005, 38(2): 171-179.
Fredrikson, G., et al., "Autoantibody against the amino acid sequence 661-680 in apo B-100 is associated with decreased carotid stenosis and cardiovascular events." Atherosclerosis 2007, 194: e188-e192.
Fredrikson, G., et al., "Immunization of atherosclerosis in apo E null mice by immunization with native and MDA-modified apo B peptide sequences." Journal of the American College of Cardiology 2002, 39(5): Supplement A; p. 240A.
Fredrikson, G., et al., "Association Between IgM Against an Aldehyde-Modified Peptide in Apolipoprotein B-100 and Progression of Carotid Disease." Stroke 2007, 38: 1495-1500.
Fredrikson, G., et al., "Associations between autoantibodies against apolipoprotein B-100 peptides and vascular complications in patients with type 2 diabetes." Diabetologia (2009), 52: 1426-1433.
Freigang, S., et al., "Immunization of LDL receptor-deficient mice with homologous malondialdehyde-modified and native LDL reduces progression of atherosclerosis by mechanisms other than induction of high titers of anitbodies to oxidative neoepitopes." Arterioscler. Thomb. Vasc. Bio., 1998, 18: 1972-1982.
Gandjini, H. et al., "Resistance to LDL oxidative modifications of a N-terminal apolipoprotein B epitope." Atherosclerosis 1991, 89: 83-93.
Gaubatz, JW., et al., "Isolation and characterization of the two major apoproteins in human lipoprotein[a]." Journal of Lipid research 1987, 28(1): 69-79.
George, J., et al., "Hyperimmunization of apo-E-deficient mice homologous malondialdehyde low-denisity lipoprotein suppresses early atherogenesis." Arteriosclerosis 1998, 138:147-152.
George, J., et al., "Induction of early atherosclerosis in LDL-receptor-deficient mice immunized with Beta2-Glycoprotein I." Circulation 1998, 98: 1108-1115.
Glass, CK., et al., "Atherosclerosis: the road ahead." Cell 2001, 104: 503-516.
Goldberg, IJ., et al., "The NH2-terminal region of apolipoprotein B is sufficient for lipoprotein association with glycosaminoglycans." The Journal of Biological Chemistry 1998, 273(52): 35355-35361.
Goncalves, I., et al., "Humoral immune response against defined oxidized low-density lipoprotein antigens reflects structure and disease activity of carotid plaques." Arterioscler. Thomb. Vasc. Biol. 2005, 25: 1250-1255.
Gresham, G.A. et al., "Atherosclerosis in man: natural history and effects." Proc.Nutr. Soc. 1972, 31: 303-306.
Griffin, TJ., et al., "Genetic analysis by peptide nucleic acid affinity MALDI-TOF mass spectometry." Nature Biotechnology 1997, 15: 1368-1372.
Shih, I. et al., "Focal Accumulation of an Apolipoprotein B-Based Synthetic Oligopeptide in the Healing Rabbit Arterial Wall." Proceedings of the National Academy of Sciences of the United States 1990, 87(4): 1436-1440.
Singh, R. et al., "Reagents for Rapid Reduction of Disulfide Bonds." Methods in Enzymology 1995, 251: 167-173.
Sjogren, P. et al., "High plasma concentrations of autoantibodies against native peptide 210 of apoB-100 are related to less coronary atherosclerosis and lower risk of myocardial infarction." European Heart Journal 2008, 29: 2218-2226.
Stemme, S. et al., "T lymphocytes from human atherosclerotic plaques recognize oxidized low density lipoprotein." PNAS 1995, 92: 3893-3897.
Storm, A. et al., "Inhibition of injury-induced arterial remodelling and carotid atherosclerosis by recombinant human antibodies against aldehyde-modified apoB-100." Atherosclerosis 2007, 190: 298-305.
Tailleux, A. et al., "Immunological properties of apoB-containing lipoprotein particles in human atherosclerotic arteries." Journal of Lipid Research 1993, 34: 719-728.

(56) References Cited

OTHER PUBLICATIONS

Uthaipibull, C. et al., "Inhibitory and blocking monoclonal antibody epitopes on merozoite surface protein 1 of the malaria parasite Plasmodium falciparum." Journal of Molecular Biology 2007, 307: 1381-1394.
Valentinova, N. et al., "Immunoreactivity of apolipoprotein B-100 in oxidatively modified low density lipoprotein." Biological Chemistry 1994, 375: 651-658.
Wang, X. et al., "Well-defined regions of apolipoprotein B-100 undergo confirmational change during its intravascular metabolism." Arterioscelrosis, Thrombosis, and Vascular Biology 2000, 20: 1301-1308.
Yang, C.Y. et al., "Sequence, structure, receptor-binding domains and internal repeats of human apolipoprotein B-100." Nature 1986, 23: 738-742.
Young, S. et al., "Definition of a non-linear conformational epitope for the apolipoprotein B-100-specific monoclonal antibody, MB47." Journal of Lipid Research 1994, 35: 399-407.
Zhou, X. et al., "LDL immunization induces T-cell-dependent antibody formation and protection against atherosclerosis." Arteriosclerosis, Thrombosis and Vascular Biology 2001, 21: 108-114.
Adams, H., et al.,"Ischemic cerebrovascular disease." Contemporary Neuroscience 2001, 15.
Anonymous, "APB_HUMAN." Oct. 1, 2000, pp. 1-7 XP 55019488, retrieved from the internet URL: http://www. Uniprot.org/uniprot/P04114.txt?version=23.
Bostrom, K. et al., Evidence for structural relationship between apoB75kDa and human plasma apolipoprotein B100, from translation of human liver mRNA in vitro and immunochemical studies with monoclonal and polyclonal antibodies. Eur J Biochem 1984, 143: 101-107.
PCT/SE2005/000394 International Search Report dated Dec. 16, 2005; 8 pages.
PCT/SE2010/050299 International Preliminary Report and Written Opinion dated Sep. 29, 2011; 12 pages.
Holvoet, P. et al., "Oxidized LDL and malondialdehyde-modified LDL in patients with acute coronary syndromes and stable coronary artery disease." Circulation 1998, 98: 1487-1494.
Hammer, A., et al., "Generation, Characterization, and Histohecmical Application of Monoclonal Antibodies Selectively Recognizing Oxidatively Modified ApoB-Containing Serum Lipoproteins." Arterioscl Throm Vasc Biol 1995, 15: 704-713.
Hanafusa, Y., et al., "Identification of B Cell Epitopes of a 30 kDa Babesia equi Merozoite Surface Protein." The Journal of Veterinary Medical Science 1998, 60(5): 563-567.
Hansson, GK., et al. "Vaccination against atherosclerosis? Induction of atheroprotective immunity." Semin. Immunopathol 2009, 31:95-101.
Hansson, GK., "Cell-mediated immunity in atherosclerosis." Current Opinion in Lipidology 1997, 8:301-311.
Hansson, K., "Inflammation, atherosclerosis, and coronary artery disease." The New England Journal of Medicine 2005, 352(16): 1685-1695.
Herzyk, E., et al., "Changes in the secondary structure of apolipoprotein B-100 after Cu2+-catalysed oxidation of human low-density lipoproteins monitored by Fourier transform infrared spectroscopy." Biochim Biophys Acta 1987, 922: 145-154.
Huynen, M., et al., "Predicting protein function by genomic context: Quantitive evaluation and qualitative inferences." Genome Research 2000, 10: 1204-1210.
Inoue, I., et al., "Marcrophage colony simulating factor prevents the progression of atherosclerosis in Watanabe heritable hyperlipidemic rabbits." Atherosclerosis 1992, 93: 245-254.
Itabe, H., et al., "A Monoclonal Antibody Against Oxidized Lipoprotein Recognizes Foam Cells in Atherosclerotic Lesions." The Journal of Biological Chemistry 1994, 265(21): 15274-15279.
Jocelyn, P., "Chemical Reduction of Disulfides." Methods in Enzymology 1987, 143, 246-256.

Jung, C., et al., "New ligands for HLA DRB1 *0301 by random selection of favourable amino acids ranked by competition studies with undecapeptide amide sublibraries." Journal of Immunological Methods 1998, 219: 139-149.
Knott, TJ., et al., "Complete protein sequence and identification of structural domains of human apolipoprotein B." Nature 1986, 323(6090): 734-738.
Koonin, E., et al., "Non-orthologous gene displacement" Trends in Genetics 1996, 12(9):334-336.
Kruezer, J., et al., "Amino terminus of apolipoprotein B suffices to produce recognition of malodialdehyde-modified low density lipoprotein by the scavenger receptor of human monocyte-macrophages." Journal of Lipid Research 1997, 38: 324-342.
Krul, E., "Reginal specificities of monoclonal anti-human apolipoprotein B antibodies." Journal of Lipid Research 1988, 29: 937-347.
Krych-Goldberg, M. et al., "Structure-function relationships of complement receptor type 1." Immunological Review 2001, 180: 112-122.
Kuby et al. "Immunology." Fourth Edition, Chapter 18:449-465, 2000.
Latif, N. et al., "Liposomes in immunology." Journal of Bioscience 1984, 6(4): 491-502.
Law, S.W., et al., Human liver apolipoprotein B-100 cDNA: Complete nucleic acid and derived amino acid sequence. Proceedings National Academy of Sciences 1986, 83 (21), 8142-8146.
Lecomte, E., et al., "Malondialdehyde adducts to, and fragmentation of, apolipoprotein B from human plasma." Clinica Chimica Acta 1993, 218(1): 39-46.
Lefvert, A.K., et al., "Heterogeneity of autoantibodies against cardiolipin and oxidatively modified LDLs revealed by human monoclonal antibodies." Journal of Internal Medicine 2000, 247: 385-390.
Leiper, J.M., et al., "Systematic expression of the complete coding sequence of apoB-100 does not reveal transmembrane determinants." Journal of Lipid Research 1996, 37: 2215-2231.
Libby, P. "Atherosclerosis: the new view." Scientific American 2002, 286: 47-55.
Lung, C.C., et al., "Immunochemical properties of malondialdehyde-protein adducts." Journal of Immunological Methods 1990, 128(1): 127-132.
McCormick, S. et al., "Mutagenesis of the human apolipoprotein B gene in a yeast artificial chromosome reveals the site of attachment for apolipoprotein(a)." PNAS 1995, 92: 10147-10151.
Milne, R. et al., "The use of monoclonal antibodies to localize the low density lipoprotein receptor-binding domain of apolipoprotein B." The Journal of Biological Chemistry 1989, 264(33): 19754-19760.
Moore, G.P., "Genetically Engineered Antibodies." Clinical Chemistry 1989, 35(9): 1849-1853.
Nakashima, Y., et al., "ApoE-deficient mice develop lesions of all phases of atherosclerosis throughout the arterial tree." Arteriosclerosis, Thrombosis, and Vascular Biology 1994, 14(1): 133-140.
Ngo, J. T. et al., "Computational complexity, protein structure prediction, and the levinthal paradox." The Protein Folding Problem and Tertiary Structure Prediction 1994, Birkhauser, Boston, Chapter 14: 491-495.
Nicoletti, A. et al., "Functionality of specific immunity in atherosclerosis." American Heart Journal 1999, 138(5): S438-S443.
Nilsson, J. et al., "Autoimmunity in atherosclerosis: a protective response losing control." Journal of Internal Medicine 2008, 263: 464-478.
Nilsson, J. et al., "Immunization with homologous oxidized low density lipoprotein reduces neointimal formation after balloon injury in hypercholesterolemic rabbits." Journal of American College of Cardiology 1997, 30(7): 1886-1891.
Nilsson, J. et al., "Immunomodulation of atherosclerosis: Implication for vaccine development." Arteriosclerosis, Thrombosis, and Vascular Biology 2005, 25: 18-28.
No Author. "LDLR_HUMAN." Accession No. P01130. Retrieved from Uniprot.
Palinski, W. et al., "Antisera and Monoclonal Antibodies Specific for Epitopes Generated during Oxidative Modification of Low Density Lipoprotein." Arteriosclerosis 1990, 10:325-335.

(56) References Cited

OTHER PUBLICATIONS

Palinski, W. et al., "Immunization of low density lipoprotein (LDL) receptor-deficient rabbits with homologous malondialdehyde-modified LDL reduces atherogenesis." PNAS 1995, 92: 821-825.

Pease, R. et al., "Use of bacterial expression cloning to localize the epitopes for a series of monoclonal antibodies against apolipoprotein B100." The Journal of Biological Chemistry 1990, 265(1): 553-568.

Pieters, J. "MHC Class II-Restricted Antigen Processing and Presentation." Advances in Immunology 2000, 75:159-208.

Rajapakse, M. et al., "Predicting Peptides Binding to MHC Class II Molecules Using Multi-Objective Evolutionary Algorithms." BMC Bioinformatics 2007, 8:459; 12pages.

Rammensee, H. et al., "MHC Ligands and Peptide Motifs: First Listing." Immunogenetics 1995, 41:178-228.

Reddick, R.L., et al., "Atherosclerosis in mice lacking Apo E: Evaluation of lesional development and progression." Arteriosclerosis, Thrombosis, and Vascular Biology 1994, 14: 141-147.

Robbio, L., et al., "Epitope mapping analysis of apolipoprotein B-100 using a surface plasmon resonance-based biosensor." Biosensors & Bioelectronics 2001, 16: 963-969.

Rosenfeld, ME et al., "Distribution of oxidation specific lipid-protein adducts and apolipoprotein B in atherosclerotic lesions of varying severity from WHHL rabbits." Arteriosclerosis, Thrombosis, and Vascular Biology 1990, 10(3): 336-349.

Schiopu, A. et al., "Recombinant antibodies to an oxidized low-density lipoprotein epitope induce rapid regression of atherosclerosis in Apobec-1–/– / low-density lipoprotein receptor –/– mice." Journal of the American College of Cardiology 2007, 50(24): 2313-2318.

Schiopu, A. et al., "Recombinant human antibodies against aldehyde-modified apolipoprotein B-100 peptide sequences inhibit atherosclerosis." Circulation 2004, 110: 2047-2052.

Schrem, A. et al., "Identification of a Domain in Guanylyl Cyclase-activating Protein 1 That Interacts with a Complex of Guanylyl Cyclase and Tubulin in Photoreceptors." The Journal of Biological Chemistry 1999, 274(10): 6244-6249.

Sercarz, E. et al., "MHC-guided processing: Binding of large antigen fragments." Nature Reviews 2003, 3:621-629.

Shah, P. et al., "Immunomodulation of atherosclerosis with a vaccine." Nature Clinical Practice Cardiovascular Medicine 2005, 2(12): 639-646.

Shah, P. et al., "Effects of recombinant lipoproptein A-1 milano on aortic atherosclerosis in apolipoprotein E-deficient mice." Circulation 1998, 97: 780-785.

* cited by examiner

SEQUENCE LISTING

```
<160> NUMBER OF SEQ ID NOS: 302

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Glu Glu Glu Met Leu Glu Asn Val Ser Leu Val Cys Pro Lys Asp Ala
1               5                   10                  15

Thr Arg Phe Lys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Ala Thr Arg Phe Lys His Leu Arg Lys Tyr Thr Tyr Asn Tyr Glu Ala
1               5                   10                  15

Glu Ser Ser Ser
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Ala Glu Ser Ser Ser Gly Val Pro Gly Thr Ala Asp Ser Arg Ser Ala
1               5                   10                  15

Thr Arg Ile Asn
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Ala Thr Arg Ile Asn Cys Lys Val Glu Leu Glu Val Pro Gln Leu Cys
1               5                   10                  15
```

```
Ser Phe Ile Leu
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Cys Ser Phe Ile Leu Lys Thr Ser Gln Cys Thr Leu Lys Glu Val Tyr
1               5                   10                  15

Gly Phe Asn Pro
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Tyr Gly Phe Asn Pro Glu Gly Lys Ala Leu Leu Lys Lys Thr Lys Asn
1               5                   10                  15

Ser Glu Glu Phe
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Asn Ser Glu Glu Phe Ala Ala Ala Met Ser Arg Tyr Glu Leu Lys Leu
1               5                   10                  15

Ala Ile Pro Glu
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Leu Ala Ile Pro Glu Gly Lys Gln Val Phe Leu Tyr Pro Glu Lys Asp
1               5                   10                  15

Glu Pro Thr Tyr
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Asp Glu Pro Thr Tyr Ile Leu Asn Ile Lys Arg Gly Ile Ile Ser Ala
1               5                   10                  15
```

```
Leu Leu Val Pro
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide

<400> SEQUENCE: 10

Ala Leu Leu Val Pro Pro Glu Thr Glu Glu Ala Lys Gln Val Leu Phe
1               5                   10                  15

Leu Asp Thr Val
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Phe Leu Asp Thr Val Tyr Gly Asn Cys Ser Thr His Phe Thr Val Lys
1               5                   10                  15

Thr Arg Lys Gly
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Lys Thr Arg Lys Gly Asn Val Ala Thr Glu Ile Ser Thr Glu Arg Asp
1               5                   10                  15

Leu Gly Gln Cys
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

Asp Leu Gly Gln Cys Asp Arg Phe Lys Pro Ile Arg Thr Gly Ile Ser
1               5                   10                  15

Pro Leu Ala Leu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide

<400> SEQUENCE: 14

Ser Pro Leu Ala Leu Ile Lys Gly Met Thr Arg Pro Leu Ser Thr Leu
```

```
1               5                   10                  15
Ile Ser Ser Ser
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide

<400> SEQUENCE: 15

Leu Ile Ser Ser Ser Gln Ser Cys Gln Tyr Thr Leu Asp Ala Lys Arg
1               5                   10                  15

Lys His Val Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Arg Lys His Val Ala Glu Ala Ile Cys Lys Glu Gln His Leu Phe Leu
1               5                   10                  15

Pro Phe Ser Tyr
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

Leu Pro Phe Ser Tyr Asn Asn Lys Tyr Gly Met Val Ala Gln Val Thr
1               5                   10                  15

Gln Thr Leu Lys
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide

<400> SEQUENCE: 18

Thr Gln Thr Leu Lys Leu Glu Asp Thr Pro Lys Ile Asn Ser Arg Phe
1               5                   10                  15

Phe Gly Glu Gly
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide

<400> SEQUENCE: 19
```

```
Phe Phe Gly Glu Gly Thr Lys Lys Met Gly Leu Ala Phe Glu Ser Thr
1               5                   10                  15

Lys Ser Thr Ser
            20
```

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide

<400> SEQUENCE: 20

```
Thr Lys Ser Thr Ser Pro Pro Lys Gln Ala Glu Ala Val Leu Lys Thr
1               5                   10                  15

Leu Gln Glu Leu
            20
```

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

```
Thr Leu Gln Glu Leu Lys Lys Leu Thr Ile Ser Glu Gln Asn Ile Gln
1               5                   10                  15

Arg Ala Asn Leu
            20
```

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

```
Gln Arg Ala Asn Leu Phe Asn Lys Leu Val Thr Glu Leu Arg Gly Leu
1               5                   10                  15

Ser Asp Glu Ala
            20
```

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

```
Leu Ser Asp Glu Ala Val Thr Ser Leu Leu Pro Gln Leu Ile Glu Val
1               5                   10                  15

Ser Ser Pro Ile
            20
```

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

```
Val Ser Ser Pro Ile Thr Leu Gln Ala Leu Val Gln Cys Gly Gln Pro
1               5                   10                  15

Gln Cys Ser Thr
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic peptide

<400> SEQUENCE: 25

Pro Gln Cys Ser Thr His Ile Leu Gln Trp Leu Lys Arg Val His Ala
1               5                   10                  15

Asn Pro Leu Leu
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Ala Asn Pro Leu Leu Ile Asp Val Val Thr Tyr Leu Val Ala Leu Ile
1               5                   10                  15

Pro Glu Pro Ser
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Ile Pro Glu Pro Ser Ala Gln Gln Leu Arg Glu Ile Phe Asn Met Ala
1               5                   10                  15

Arg Asp Gln Arg
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide

<400> SEQUENCE: 28

Ala Arg Asp Gln Arg Ser Arg Ala Thr Leu Tyr Ala Leu Ser His Ala
1               5                   10                  15

Val Asn Asn Tyr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 29

Ala Val Asn Asn Tyr His Lys Thr Asn Pro Thr Gly Thr Gln Glu Leu
1               5                   10                  15

Leu Asp Ile Ala
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

Leu Leu Asp Ile Ala Asn Tyr Leu Met Glu Gln Ile Gln Asp Asp Cys
1               5                   10                  15

Thr Gly Asp Glu
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide

<400> SEQUENCE: 31

Cys Thr Gly Asp Glu Asp Tyr Thr Tyr Leu Ile Leu Arg Val Ile Gly
1               5                   10                  15

Asn Met Gly Gln
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic peptide

<400> SEQUENCE: 32

Gly Asn Met Gly Gln Thr Met Glu Gln Leu Thr Pro Glu Leu Lys Ser
1               5                   10                  15

Ser Ile Leu Lys
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

Ser Ser Ile Leu Lys Cys Val Gln Ser Thr Lys Pro Ser Leu Met Ile
1               5                   10                  15

Gln Lys Ala Ala
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 34

Ile Gln Lys Ala Ala Ile Gln Ala Leu Arg Lys Met Glu Pro Lys Asp
1               5                   10                  15

Lys Asp Gln Glu
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Asp Lys Asp Gln Glu Val Leu Leu Gln Thr Phe Leu Asp Asp Ala Ser
1               5                   10                  15

Pro Gly Asp Lys
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Ser Pro Gly Asp Lys Arg Leu Ala Ala Tyr Leu Met Leu Met Arg Ser
1               5                   10                  15

Pro Ser Gln Ala
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide

<400> SEQUENCE: 37

Ser Pro Ser Gln Ala Asp Ile Asn Lys Ile Val Gln Ile Leu Pro Trp
1               5                   10                  15

Glu Gln Asn Glu
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide

<400> SEQUENCE: 38

Trp Glu Gln Asn Glu Gln Val Lys Asn Phe Val Ala Ser His Ile Ala
1               5                   10                  15

Asn Ile Leu Asn
            20

<210> SEQ ID NO 39
<211> LENGTH: 20
<212> TYPE: PRT
<213> ORGANISM: Artificial Sequence
<220> FEATURE:
```

<223> OTHER INFORMATION: Synthetic peptide

<400> SEQUENCE: 39

Ala Asn Ile Leu Asn Ser Glu Glu Leu Asp Ile Gln Asp Leu Lys Lys
1               5                   10                  15

Leu Val Lys Glu
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40

Lys Leu Val Lys Glu Ala Leu Lys Glu Ser Gln Leu Pro Thr Val Met
1               5                   10                  15

Asp Phe Arg Lys
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide

<400> SEQUENCE: 41

Met Asp Phe Arg Lys Phe Ser Arg Asn Tyr Gln Leu Tyr Lys Ser Val
1               5                   10                  15

Ser Leu Pro Ser
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide

<400> SEQUENCE: 42

Val Ser Leu Pro Ser Leu Asp Pro Ala Ser Ala Lys Ile Glu Gly Asn
1               5                   10                  15

Leu Ile Phe Asp
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic peptide

<400> SEQUENCE: 43

Asn Leu Ile Phe Asp Pro Asn Asn Tyr Leu Pro Lys Glu Ser Met Leu
1               5                   10                  15

Lys Thr Thr Leu
            20

<210> SEQ ID NO 44
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 44

Leu Lys Thr Thr Leu Thr Ala Phe Gly Phe Ala Ser Ala Asp Leu Ile
1               5                   10                  15

Glu Ile Gly Leu
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic peptide

<400> SEQUENCE: 45

Ile Glu Ile Gly Leu Glu Gly Lys Gly Phe Glu Pro Thr Leu Glu Ala
1               5                   10                  15

Leu Phe Gly Lys
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Ala Leu Phe Gly Lys Gln Gly Phe Phe Pro Asp Ser Val Asn Lys Ala
1               5                   10                  15

Leu Tyr Trp Val
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic peptide

<400> SEQUENCE: 47

Ala Leu Tyr Trp Val Asn Gly Gln Val Pro Asp Gly Val Ser Lys Val
1               5                   10                  15

Leu Val Asp His
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

Val Leu Val Asp His Phe Gly Tyr Thr Lys Asp Asp Lys His Glu Gln
1               5                   10                  15

Asp Met Val Asn
            20

<210> SEQ ID NO 49
<211> LENGTH: 20
<212> TYPE: PRT
```

<213> ORGANISM: Artificial Sequence
<220> FEATURE:
<223> OTHER INFORMATION: Synthetic peptide

<400> SEQUENCE: 49

Gln Asp Met Val Asn Gly Ile Met Leu Ser Val Glu Lys Leu Ile Lys
1               5                   10                  15

Asp Leu Lys Ser
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic peptide

<400> SEQUENCE: 50

Lys Asp Leu Lys Ser Lys Glu Val Pro Glu Ala Arg Ala Tyr Leu Arg
1               5                   10                  15

Ile Leu Gly Glu
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic peptide

<400> SEQUENCE: 51

Arg Ile Leu Gly Glu Glu Leu Gly Phe Ala Ser Leu His Asp Leu Gln
1               5                   10                  15

Leu Leu Gly Lys
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Gln Leu Leu Gly Lys Leu Leu Leu Met Gly Ala Arg Thr Leu Gln Gly
1               5                   10                  15

Ile Pro Gln Met
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic peptide

<400> SEQUENCE: 53

Gly Ile Pro Gln Met Ile Gly Glu Val Ile Arg Lys Gly Ser Lys Asn
1               5                   10                  15

Asp Phe Phe Leu
            20

<210> SEQ ID NO 54
<211> LENGTH: 20

```
<212> TYPE: PRT
<213> ORGANISM: Artificial Sequence
<220> FEATURE:
<223> OTHER INFORMATION: Synthetic peptide

<400> SEQUENCE: 54

Asn Asp Phe Phe Leu His Tyr Ile Phe Met Glu Asn Ala Phe Glu Leu
1               5                   10                  15

Pro Thr Gly Ala
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Leu Pro Thr Gly Ala Gly Leu Gln Leu Gln Ile Ser Ser Ser Gly Val
1               5                   10                  15

Ile Ala Pro Gly
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Val Ile Ala Pro Gly Ala Lys Ala Gly Val Lys Leu Glu Val Ala Asn
1               5                   10                  15

Met Gln Ala Glu
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic peptide

<400> SEQUENCE: 57

Asn Met Gln Ala Glu Leu Val Ala Lys Pro Ser Val Ser Val Glu Phe
1               5                   10                  15

Val Thr Asn Met
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic peptide

<400> SEQUENCE: 58

Phe Val Thr Asn Met Gly Ile Ile Ile Pro Asp Phe Ala Arg Ser Gly
1               5                   10                  15

Val Gln Met Asn
            20

<210> SEQ ID NO 59
```

<211> LENGTH: 20
<212> TYPE: PRT
<213> ORGANISM: Artificial Sequence
<220> FEATURE:
<223> OTHER INFORMATION: Synthetic peptide

<400> SEQUENCE: 59

Gly Val Gln Met Asn Thr Asn Phe Phe His Glu Ser Gly Leu Glu Ala
1               5                   10                  15

His Val Ala Leu
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic peptide

<400> SEQUENCE: 60

Ala His Val Ala Leu Lys Ala Gly Lys Leu Lys Phe Ile Ile Pro Ser
1               5                   10                  15

Pro Lys Arg Pro
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic peptide

<400> SEQUENCE: 61

Ser Pro Lys Arg Pro Val Lys Leu Leu Ser Gly Gly Asn Thr Leu His
1               5                   10                  15

Leu Val Ser Thr
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic peptide

<400> SEQUENCE: 62

His Leu Val Ser Thr Thr Lys Thr Glu Val Ile Pro Pro Leu Ile Glu
1               5                   10                  15

Asn Arg Gln Ser
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic peptide

<400> SEQUENCE: 63

Glu Asn Arg Gln Ser Trp Ser Val Cys Lys Gln Val Phe Pro Gly Leu
1               5                   10                  15

Asn Tyr Cys Thr
            20

```
<210> SEQ ID NO 64
<211> LENGTH: 20
<212> TYPE: PRT
<213> ORGANISM: Artificial Sequence
<220> FEATURE:
<223> OTHER INFORMATION: Synthetic peptide

<400> SEQUENCE: 64

Leu Asn Tyr Cys Thr Ser Gly Ala Tyr Ser Asn Ala Ser Ser Thr Asp
1               5                   10                  15

Ser Ala Ser Tyr
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic peptide

<400> SEQUENCE: 65

Asp Ser Ala Ser Tyr Tyr Pro Leu Thr Gly Asp Thr Arg Leu Glu Leu
1               5                   10                  15

Glu Leu Arg Pro
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide

<400> SEQUENCE: 66

Leu Glu Leu Arg Pro Thr Gly Glu Ile Glu Gln Tyr Ser Val Ser Ala
1               5                   10                  15

Thr Tyr Glu Leu
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic peptide

<400> SEQUENCE: 67

Ala Thr Tyr Glu Leu Gln Arg Glu Asp Arg Ala Leu Val Asp Thr Leu
1               5                   10                  15

Lys Phe Val Thr
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic peptide

<400> SEQUENCE: 68

Leu Lys Phe Val Thr Gln Ala Glu Gly Ala Lys Gln Thr Glu Ala Thr
1               5                   10                  15

Met Thr Phe Lys
            20
```

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide

<400> SEQUENCE: 69

Thr Met Thr Phe Lys Tyr Asn Arg Gln Ser Met Thr Leu Ser Glu
1               5                   10                  15

Val Gln Ile Pro
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic peptide

<400> SEQUENCE: 70

Glu Val Gln Ile Pro Asp Phe Asp Val Asp Leu Gly Thr Ile Leu Arg
1               5                   10                  15

Val Asn Asp Glu
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide

<400> SEQUENCE: 71

Arg Val Asn Asp Glu Ser Thr Glu Gly Lys Thr Ser Tyr Arg Leu Thr
1               5                   10                  15

Leu Asp Ile Gln
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic peptide

<400> SEQUENCE: 72

Thr Leu Asp Ile Gln Asn Lys Lys Ile Thr Glu Val Ala Leu Met Gly
1               5                   10                  15

His Leu Ser Cys
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic peptide

<400> SEQUENCE: 73

Gly His Leu Ser Cys Asp Thr Lys Glu Glu Arg Lys Ile Lys Gly Val
1               5                   10                  15

Ile Ser Ile Pro
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic peptide

<400> SEQUENCE: 74

Val Ile Ser Ile Pro Arg Leu Gln Ala Glu Ala Arg Ser Glu Ile Leu
1               5                   10                  15

Ala His Trp Ser
            20

<210> SEQ ID NO 75
<211> LENGTH: 20
<212> TYPE: PRT
<213> ORGANISM: Artificial Sequence
<220> FEATURE:
<223> OTHER INFORMATION: Synthetic peptide

<400> SEQUENCE: 75

Leu Ala His Trp Ser Pro Ala Lys Leu Leu Leu Gln Met Asp Ser Ser
1               5                   10                  15

Ala Thr Ala Tyr
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic peptide

<400> SEQUENCE: 76

Ser Ala Thr Ala Tyr Gly Ser Thr Val Ser Lys Arg Val Ala Trp His
1               5                   10                  15

Tyr Asp Glu Glu
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic peptide

<400> SEQUENCE: 77

His Tyr Asp Glu Glu Lys Ile Glu Phe Glu Trp Asn Thr Gly Thr Asn
1               5                   10                  15

Val Asp Thr Lys
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic peptide

<400> SEQUENCE: 78

Asn Val Asp Thr Lys Lys Met Thr Ser Asn Phe Pro Val Asp Leu Ser
1               5                   10                  15

Asp Tyr Pro Lys

```
                        20

<210> SEQ ID NO 79
<211> LENGTH: 20
<212> TYPE: PRT
<213> ORGANISM: Artificial Sequence
<220> FEATURE:
<223> OTHER INFORMATION: Synthetic peptide

<400> SEQUENCE: 79

Ser Asp Tyr Pro Lys Ser Leu His Met Tyr Ala Asn Arg Leu Leu Asp
1               5                   10                  15

His Arg Val Pro
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic peptide

<400> SEQUENCE: 80

Asp His Arg Val Pro Glu Thr Asp Met Thr Phe Arg His Val Gly Ser
1               5                   10                  15

Lys Leu Ile Val
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic peptide

<400> SEQUENCE: 81

Ser Lys Leu Ile Val Ala Met Ser Ser Trp Leu Gln Lys Ala Ser Gly
1               5                   10                  15

Ser Leu Pro Tyr
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic peptide

<400> SEQUENCE: 82

Gly Ser Leu Pro Tyr Thr Gln Thr Leu Gln Asp His Leu Asn Ser Leu
1               5                   10                  15

Lys Glu Phe Asn
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic peptide

<400> SEQUENCE: 83

Leu Lys Glu Phe Asn Leu Gln Asn Met Gly Leu Pro Asp Phe His Ile
1               5                   10                  15
```

```
Pro Glu Asn Leu
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic peptide

<400> SEQUENCE: 84

Ile Pro Glu Asn Leu Phe Leu Lys Ser Asp Gly Arg Val Lys Tyr Thr
1               5                   10                  15

Leu Asn Lys Asn
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic peptide

<400> SEQUENCE: 85

Thr Leu Asn Lys Asn Ser Leu Lys Ile Glu Ile Pro Leu Pro Phe Gly
1               5                   10                  15

Gly Lys Ser Ser
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic peptide

<400> SEQUENCE: 86

Gly Gly Lys Ser Ser Arg Asp Leu Lys Met Leu Glu Thr Val Arg Thr
1               5                   10                  15

Pro Ala Leu His
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic peptide

<400> SEQUENCE: 87

Thr Pro Ala Leu His Phe Lys Ser Val Gly Phe His Leu Pro Ser Arg
1               5                   10                  15

Glu Phe Gln Val
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic peptide

<400> SEQUENCE: 88

Arg Glu Phe Gln Val Pro Thr Phe Thr Ile Pro Lys Leu Tyr Gln Leu
1               5                   10                  15
```

Gln Val Pro Leu
            20

<210> SEQ ID NO 89
<211> LENGTH: 20
<212> TYPE: PRT
<213> ORGANISM: Artificial Sequence
<220> FEATURE:
<223> OTHER INFORMATION: Synthetic peptide

<400> SEQUENCE: 89

Leu Gln Val Pro Leu Leu Gly Val Leu Asp Leu Ser Thr Asn Val Tyr
1               5                   10                  15

Ser Asn Leu Tyr
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic peptide

<400> SEQUENCE: 90

Tyr Ser Asn Leu Tyr Asn Trp Ser Ala Ser Tyr Ser Gly Gly Asn Thr
1               5                   10                  15

Ser Thr Asp His
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic peptide

<400> SEQUENCE: 91

Thr Ser Thr Asp His Phe Ser Leu Arg Ala Arg Tyr His Met Lys Ala
1               5                   10                  15

Asp Ser Val Val
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic peptide

<400> SEQUENCE: 92

Ala Asp Ser Val Val Asp Leu Leu Ser Tyr Asn Val Gln Gly Ser Gly
1               5                   10                  15

Glu Thr Thr Tyr
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic peptide

<400> SEQUENCE: 93

Gly Glu Thr Thr Tyr Asp His Lys Asn Thr Phe Thr Leu Ser Cys Asp

```
1               5                   10                  15

Gly Ser Leu Arg
            20

<210> SEQ ID NO 94
<211> LENGTH: 20
<212> TYPE: PRT
<213> ORGANISM: Artificial Sequence
<220> FEATURE:
<223> OTHER INFORMATION: Synthetic peptide

<400> SEQUENCE: 94

Asp Gly Ser Leu Arg His Lys Phe Leu Asp Ser Asn Ile Lys Phe Ser
1               5                   10                  15

His Val Glu Lys
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic peptide

<400> SEQUENCE: 95

Ser His Val Glu Lys Leu Gly Asn Asn Pro Val Ser Lys Gly Leu Leu
1               5                   10                  15

Ile Phe Asp Ala
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic peptide

<400> SEQUENCE: 96

Leu Ile Phe Asp Ala Ser Ser Ser Trp Gly Pro Gln Met Ser Ala Ser
1               5                   10                  15

Val His Leu Asp
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic peptide

<400> SEQUENCE: 97

Ser Val His Leu Asp Ser Lys Lys Gln His Leu Phe Val Lys Glu
1               5                   10                  15

Val Lys Ile Asp
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic peptide

<400> SEQUENCE: 98
```

```
Glu Val Lys Ile Asp Gly Gln Phe Arg Val Ser Ser Phe Tyr Ala Lys
1               5                   10                  15

Gly Thr Tyr Gly
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic peptide

<400> SEQUENCE: 99

Lys Gly Thr Tyr Gly Leu Ser Cys Gln Arg Asp Pro Asn Thr Gly Arg
1               5                   10                  15

Leu Asn Gly Glu
            20

<210> SEQ ID NO 100
<211> LENGTH: 20
<212> TYPE: PRT
<213> ORGANISM: Artificial Sequence
<220> FEATURE:
<223> OTHER INFORMATION: Synthetic peptide

<400> SEQUENCE: 100

Arg Leu Asn Gly Glu Ser Asn Leu Arg Phe Asn Ser Ser Tyr Leu Gln
1               5                   10                  15

Gly Thr Asn Gln
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic peptide

<400> SEQUENCE: 101

Gln Gly Thr Asn Gln Ile Thr Gly Arg Tyr Glu Asp Gly Thr Leu Ser
1               5                   10                  15

Leu Thr Ser Thr
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic peptide

<400> SEQUENCE: 102

Ser Leu Thr Ser Thr Ser Asp Leu Gln Ser Gly Ile Ile Lys Asn Thr
1               5                   10                  15

Ala Ser Leu Lys
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic peptide

<400> SEQUENCE: 103
```

```
Thr Ala Ser Leu Lys Tyr Glu Asn Tyr Glu Leu Thr Leu Lys Ser Asp
1               5                   10                  15

Thr Asn Gly Lys
            20
```

<210> SEQ ID NO 104
<211> LENGTH: 20
<212> TYPE: PRT
<213> ORGANISM: Artificial Sequence
<220> FEATURE:
<223> OTHER INFORMATION: Synthetic peptide

<400> SEQUENCE: 104

```
Asp Thr Asn Gly Lys Tyr Lys Asn Phe Ala Thr Ser Asn Lys Met Asp
1               5                   10                  15

Met Thr Phe Ser
            20
```

<210> SEQ ID NO 105
<211> LENGTH: 20
<212> TYPE: PRT
<213> ORGANISM: Artificial Sequence
<220> FEATURE:
<223> OTHER INFORMATION: Synthetic peptide

<400> SEQUENCE: 105

```
Asp Met Thr Phe Ser Lys Gln Asn Ala Leu Leu Arg Ser Glu Tyr Gln
1               5                   10                  15

Ala Asp Tyr Glu
            20
```

<210> SEQ ID NO 106
<211> LENGTH: 20
<212> TYPE: PRT
<213> ORGANISM: Artificial Sequence
<220> FEATURE:
<223> OTHER INFORMATION: Synthetic peptide

<400> SEQUENCE: 106

```
Gln Ala Asp Tyr Glu Ser Leu Arg Phe Phe Ser Leu Leu Ser Gly Ser
1               5                   10                  15

Leu Asn Ser His
            20
```

<210> SEQ ID NO 107
<211> LENGTH: 20
<212> TYPE: PRT
<213> ORGANISM: Artificial Sequence
<220> FEATURE:
<223> OTHER INFORMATION: Synthetic peptide

<400> SEQUENCE: 107

```
Ser Leu Asn Ser His Gly Leu Glu Leu Asn Ala Asp Ile Leu Gly Thr
1               5                   10                  15

Asp Lys Ile Asn
            20
```

<210> SEQ ID NO 108
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 108

Thr Asp Lys Ile Asn Ser Gly Ala His Lys Ala Thr Leu Arg Ile Gly
1               5                   10                  15

Gln Asp Gly Ile
            20

<210> SEQ ID NO 109
<211> LENGTH: 20
<212> TYPE: PRT
<213> ORGANISM: Artificial Sequence
<220> FEATURE:
<223> OTHER INFORMATION: Synthetic peptide

<400> SEQUENCE: 109

Gly Gln Asp Gly Ile Ser Thr Ser Ala Thr Thr Asn Leu Lys Cys Ser
1               5                   10                  15

Leu Leu Val Leu
            20

<210> SEQ ID NO 110
<211> LENGTH: 20
<212> TYPE: PRT
<213> ORGANISM: Artificial Sequence
<220> FEATURE:
<223> OTHER INFORMATION: Synthetic peptide

<400> SEQUENCE: 110

Ser Leu Leu Val Leu Glu Asn Glu Leu Asn Ala Glu Leu Gly Leu Ser
1               5                   10                  15

Gly Ala Ser Met
            20

<210> SEQ ID NO 111
<211> LENGTH: 20
<212> TYPE: PRT
<213> ORGANISM: Artificial Sequence
<220> FEATURE:
<223> OTHER INFORMATION: Synthetic peptide

<400> SEQUENCE: 111

Ser Gly Ala Ser Met Lys Leu Thr Thr Asn Gly Arg Phe Arg Glu His
1               5                   10                  15

Asn Ala Lys Phe
            20

<210> SEQ ID NO 112
<211> LENGTH: 20
<212> TYPE: PRT
<213> ORGANISM: Artificial Sequence
<220> FEATURE:
<223> OTHER INFORMATION: Synthetic peptide

<400> SEQUENCE: 112

His Asn Ala Lys Phe Ser Leu Asp Gly Lys Ala Ala Leu Thr Glu Leu
1               5                   10                  15

Ser Leu Gly Ser
            20

<210> SEQ ID NO 113
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 113

Leu Ser Leu Gly Ser Ala Tyr Gln Ala Met Ile Leu Gly Val Asp Ser
1               5                   10                  15

Lys Asn Ile Phe
            20

<210> SEQ ID NO 114
<211> LENGTH: 20
<212> TYPE: PRT
<213> ORGANISM: Artificial Sequence
<220> FEATURE:
<223> OTHER INFORMATION: Synthetic peptide

<400> SEQUENCE: 114

Ser Lys Asn Ile Phe Asn Phe Lys Val Ser Gln Glu Gly Leu Lys Leu
1               5                   10                  15

Ser Asn Asp Met
            20

<210> SEQ ID NO 115
<211> LENGTH: 20
<212> TYPE: PRT
<213> ORGANISM: Artificial Sequence
<220> FEATURE:
<223> OTHER INFORMATION: Synthetic peptide

<400> SEQUENCE: 115

Leu Ser Asn Asp Met Met Gly Ser Tyr Ala Glu Met Lys Phe Asp His
1               5                   10                  15

Thr Asn Ser Leu
            20

<210> SEQ ID NO 116
<211> LENGTH: 20
<212> TYPE: PRT
<213> ORGANISM: Artificial Sequence
<220> FEATURE:
<223> OTHER INFORMATION: Synthetic peptide

<400> SEQUENCE: 116

His Thr Asn Ser Leu Asn Ile Ala Gly Leu Ser Leu Asp Phe Ser Ser
1               5                   10                  15

Lys Leu Asp Asn
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic peptide

<400> SEQUENCE: 117

Ser Lys Leu Asp Asn Ile Tyr Ser Ser Asp Lys Phe Tyr Lys Gln Thr
1               5                   10                  15

Val Asn Leu Gln
            20

<210> SEQ ID NO 118
<211> LENGTH: 20
<212> TYPE: PRT
<213> ORGANISM: Artificial Sequence
<220> FEATURE:
```

```
<223> OTHER INFORMATION: Synthetic peptide

<400> SEQUENCE: 118

Thr Val Asn Leu Gln Leu Gln Pro Tyr Ser Leu Val Thr Thr Leu Asn
1               5                   10                  15

Ser Asp Leu Lys
            20

<210> SEQ ID NO 119
<211> LENGTH: 20
<212> TYPE: PRT
<213> ORGANISM: Artificial Sequence
<220> FEATURE:
<223> OTHER INFORMATION: Synthetic peptide

<400> SEQUENCE: 119

Asn Ser Asp Leu Lys Tyr Asn Ala Leu Asp Leu Thr Asn Asn Gly Lys
1               5                   10                  15

Leu Arg Leu Glu
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic peptide

<400> SEQUENCE: 120

Lys Leu Arg Leu Glu Pro Leu Lys Leu His Val Ala Gly Asn Leu Lys
1               5                   10                  15

Gly Ala Tyr Gln
            20

<210> SEQ ID NO 121
<211> LENGTH: 20
<212> TYPE: PRT
<213> ORGANISM: Artificial Sequence
<220> FEATURE:
<223> OTHER INFORMATION: Synthetic peptide

<400> SEQUENCE: 121

Lys Gly Ala Tyr Gln Asn Asn Glu Ile Lys His Ile Tyr Ala Ile Ser
1               5                   10                  15

Ser Ala Ala Leu
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic peptide

<400> SEQUENCE: 122

Ser Ser Ala Ala Leu Ser Ala Ser Tyr Lys Ala Asp Thr Val Ala Lys
1               5                   10                  15

Val Gln Gly Val
            20

<210> SEQ ID NO 123
<211> LENGTH: 20
<212> TYPE: PRT
<213> ORGANISM: Artificial Sequence
```

```
<220> FEATURE:
<223> OTHER INFORMATION: Synthetic peptide

<400> SEQUENCE: 123

Lys Val Gln Gly Val Glu Phe Ser His Arg Leu Asn Thr Asp Ile Ala
1               5                   10                  15

Gly Leu Ala Ser
            20

<210> SEQ ID NO 124
<211> LENGTH: 20
<212> TYPE: PRT
<213> ORGANISM: Artificial Sequence
<220> FEATURE:
<223> OTHER INFORMATION: Synthetic peptide

<400> SEQUENCE: 124

Ala Gly Leu Ala Ser Ala Ile Asp Met Ser Thr Asn Tyr Asn Ser Asp
1               5                   10                  15

Ser Leu His Phe
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic peptide

<400> SEQUENCE: 125

Asp Ser Leu His Phe Ser Asn Val Phe Arg Ser Val Met Ala Pro Phe
1               5                   10                  15

Thr Met Thr Ile
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic peptide

<400> SEQUENCE: 126

Phe Thr Met Thr Ile Asp Ala His Thr Asn Gly Asn Gly Lys Leu Ala
1               5                   10                  15

Leu Trp Gly Glu
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic peptide

<400> SEQUENCE: 127

Ala Leu Trp Gly Glu His Thr Gly Gln Leu Tyr Ser Lys Phe Leu Leu
1               5                   10                  15

Lys Ala Glu Pro
            20

<210> SEQ ID NO 128
<211> LENGTH: 20
<212> TYPE: PRT
```

```
<213> ORGANISM: Artificial Sequence
<220> FEATURE:
<223> OTHER INFORMATION: Synthetic peptide

<400> SEQUENCE: 128

Leu Lys Ala Glu Pro Leu Ala Phe Thr Phe Ser His Asp Tyr Lys Gly
1               5                   10                  15

Ser Thr Ser His
            20

<210> SEQ ID NO 129
<211> LENGTH: 20
<212> TYPE: PRT
<213> ORGANISM: Artificial Sequence
<220> FEATURE:
<223> OTHER INFORMATION: Synthetic peptide

<400> SEQUENCE: 129

Gly Ser Thr Ser His His Leu Val Ser Arg Lys Ser Ile Ser Ala Ala
1               5                   10                  15

Leu Glu His Lys
            20

<210> SEQ ID NO 130
<211> LENGTH: 20
<212> TYPE: PRT
<213> ORGANISM: Artificial Sequence
<220> FEATURE:
<223> OTHER INFORMATION: Synthetic peptide

<400> SEQUENCE: 130

Ala Leu Glu His Lys Val Ser Ala Leu Leu Thr Pro Ala Glu Gln Thr
1               5                   10                  15

Gly Thr Trp Lys
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic peptide

<400> SEQUENCE: 131

Thr Gly Thr Trp Lys Leu Lys Thr Gln Phe Asn Asn Asn Glu Tyr Ser
1               5                   10                  15

Gln Asp Leu Asp
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide

<400> SEQUENCE: 132

Ser Gln Asp Leu Asp Ala Tyr Asn Thr Lys Asp Lys Ile Gly Val Glu
1               5                   10                  15

Leu Thr Gly Arg
            20

<210> SEQ ID NO 133
<211> LENGTH: 20
```

```
<212> TYPE: PRT
<213> ORGANISM: Artificial Sequence
<220> FEATURE:
<223> OTHER INFORMATION: Synthetic peptide

<400> SEQUENCE: 133

Glu Leu Thr Gly Arg Thr Leu Ala Asp Leu Thr Leu Leu Asp Ser Pro
1               5                   10                  15

Ile Lys Val Pro
            20

<210> SEQ ID NO 134
<211> LENGTH: 20
<212> TYPE: PRT
<213> ORGANISM: Artificial Sequence
<220> FEATURE:
<223> OTHER INFORMATION: Synthetic peptide

<400> SEQUENCE: 134

Pro Ile Lys Val Pro Leu Leu Ser Glu Pro Ile Asn Ile Ile Asp
1               5                   10                  15

Ala Leu Glu Met
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic peptide

<400> SEQUENCE: 135

Asp Ala Leu Glu Met Arg Asp Ala Val Glu Lys Pro Gln Glu Phe Thr
1               5                   10                  15

Ile Val Ala Phe
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic peptide

<400> SEQUENCE: 136

Thr Ile Val Ala Phe Val Lys Tyr Asp Lys Asn Gln Asp Val His Ser
1               5                   10                  15

Ile Asn Leu Pro
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic peptide

<400> SEQUENCE: 137

Ser Ile Asn Leu Pro Phe Phe Glu Thr Leu Gln Glu Tyr Phe Glu Arg
1               5                   10                  15

Asn Arg Gln Thr
            20

<210> SEQ ID NO 138
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 138

Arg Asn Arg Gln Thr Ile Ile Val Val Val Glu Asn Val Gln Arg Asn
1               5                   10                  15

Leu Lys His Ile
            20

<210> SEQ ID NO 139
<211> LENGTH: 20
<212> TYPE: PRT
<213> ORGANISM: Artificial Sequence
<220> FEATURE:
<223> OTHER INFORMATION: Synthetic peptide

<400> SEQUENCE: 139

Asn Leu Lys His Ile Asn Ile Asp Gln Phe Val Arg Lys Tyr Arg Ala
1               5                   10                  15

Ala Leu Gly Lys
            20

<210> SEQ ID NO 140
<211> LENGTH: 20
<212> TYPE: PRT
<213> ORGANISM: Artificial Sequence
<220> FEATURE:
<223> OTHER INFORMATION: Synthetic peptide

<400> SEQUENCE: 140

Ala Ala Leu Gly Lys Leu Pro Gln Gln Ala Asn Asp Tyr Leu Asn Ser
1               5                   10                  15

Phe Asn Trp Glu
            20

<210> SEQ ID NO 141
<211> LENGTH: 20
<212> TYPE: PRT
<213> ORGANISM: Artificial Sequence
<220> FEATURE:
<223> OTHER INFORMATION: Synthetic peptide

<400> SEQUENCE: 141

Ser Phe Asn Trp Glu Arg Gln Val Ser His Ala Lys Glu Lys Leu Thr
1               5                   10                  15

Ala Leu Thr Lys
            20

<210> SEQ ID NO 142
<211> LENGTH: 20
<212> TYPE: PRT
<213> ORGANISM: Artificial Sequence
<220> FEATURE:
<223> OTHER INFORMATION: Synthetic peptide

<400> SEQUENCE: 142

Thr Ala Leu Thr Lys Lys Tyr Arg Ile Thr Glu Asn Asp Ile Gln Ile
1               5                   10                  15

Ala Leu Asp Asp
            20
```

<210> SEQ ID NO 143
<211> LENGTH: 20
<212> TYPE: PRT
<213> ORGANISM: Artificial Sequence
<220> FEATURE:
<223> OTHER INFORMATION: Synthetic peptide

<400> SEQUENCE: 143

Ile Ala Leu Asp Asp Ala Lys Ile Asn Phe Asn Glu Lys Leu Ser Gln
1               5                   10                  15

Leu Gln Thr Tyr
            20

<210> SEQ ID NO 144
<211> LENGTH: 20
<212> TYPE: PRT
<213> ORGANISM: Artificial Sequence
<220> FEATURE:
<223> OTHER INFORMATION: Synthetic peptide

<400> SEQUENCE: 144

Gln Leu Gln Thr Tyr Met Ile Gln Phe Asp Gln Tyr Ile Lys Asp Ser
1               5                   10                  15

Tyr Asp Leu His
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic peptide

<400> SEQUENCE: 145

Ser Tyr Asp Leu His Asp Leu Lys Ile Ala Ile Ala Asn Ile Ile Asp
1               5                   10                  15

Glu Ile Ile Glu
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic peptide

<400> SEQUENCE: 146

Asp Glu Ile Ile Glu Lys Leu Lys Ser Leu Asp Glu His Tyr His Ile
1               5                   10                  15

Arg Val Asn Leu
            20

<210> SEQ ID NO 147
<211> LENGTH: 20
<212> TYPE: PRT
<213> ORGANISM: Artificial Sequence
<220> FEATURE:
<223> OTHER INFORMATION: Synthetic peptide

<400> SEQUENCE: 147

Ile Arg Val Asn Leu Val Lys Thr Ile His Asp Leu His Leu Phe Ile
1               5                   10                  15

Glu Asn Ile Asp
            20

```
<210> SEQ ID NO 148
<211> LENGTH: 20
<212> TYPE: PRT
<213> ORGANISM: Artificial Sequence
<220> FEATURE:
<223> OTHER INFORMATION: Synthetic peptide

<400> SEQUENCE: 148

Ile Glu Asn Ile Asp Phe Asn Lys Ser Gly Ser Ser Thr Ala Ser Trp
1               5                   10                  15

Ile Gln Asn Val
            20

<210> SEQ ID NO 149
<211> LENGTH: 20
<212> TYPE: PRT
<213> ORGANISM: Artificial Sequence
<220> FEATURE:
<223> OTHER INFORMATION: Synthetic peptide

<400> SEQUENCE: 149

Trp Ile Gln Asn Val Asp Thr Lys Tyr Gln Ile Arg Ile Gln Ile Gln
1               5                   10                  15

Glu Lys Leu Gln
            20

<210> SEQ ID NO 150
<211> LENGTH: 20
<212> TYPE: PRT
<213> ORGANISM: Artificial Sequence
<220> FEATURE:
<223> OTHER INFORMATION: Synthetic peptide

<400> SEQUENCE: 150

Gln Glu Lys Leu Gln Gln Leu Lys Arg His Ile Gln Asn Ile Asp Ile
1               5                   10                  15

Gln His Leu Ala
            20

<210> SEQ ID NO 151
<211> LENGTH: 20
<212> TYPE: PRT
<213> ORGANISM: Artificial Sequence
<220> FEATURE:
<223> OTHER INFORMATION: Synthetic peptide

<400> SEQUENCE: 151

Ile Gln His Leu Ala Gly Lys Leu Lys Gln His Ile Glu Ala Ile Asp
1               5                   10                  15

Val Arg Val Leu
            20

<210> SEQ ID NO 152
<211> LENGTH: 20
<212> TYPE: PRT
<213> ORGANISM: Artificial Sequence
<220> FEATURE:
<223> OTHER INFORMATION: Synthetic peptide

<400> SEQUENCE: 152

Asp Val Arg Val Leu Leu Asp Gln Leu Gly Thr Thr Ile Ser Phe Glu
1               5                   10                  15

Arg Ile Asn Asp
            20
```

```
<210> SEQ ID NO 153
<211> LENGTH: 20
<212> TYPE: PRT
<213> ORGANISM: Artificial Sequence
<220> FEATURE:
<223> OTHER INFORMATION: Synthetic peptide

<400> SEQUENCE: 153

Glu Arg Ile Asn Asp Val Leu Glu His Val Lys His Phe Val Ile Asn
1               5                   10                  15

Leu Ile Gly Asp
            20

<210> SEQ ID NO 154
<211> LENGTH: 20
<212> TYPE: PRT
<213> ORGANISM: Artificial Sequence
<220> FEATURE:
<223> OTHER INFORMATION: Synthetic peptide

<400> SEQUENCE: 154

Asn Leu Ile Gly Asp Phe Glu Val Ala Glu Lys Ile Asn Ala Phe Arg
1               5                   10                  15

Ala Lys Val His
            20

<210> SEQ ID NO 155
<211> LENGTH: 20
<212> TYPE: PRT
<213> ORGANISM: Artificial Sequence
<220> FEATURE:
<223> OTHER INFORMATION: Synthetic peptide

<400> SEQUENCE: 155

Arg Ala Lys Val His Glu Leu Ile Glu Arg Tyr Glu Val Asp Gln Gln
1               5                   10                  15

Ile Gln Val Leu
            20

<210> SEQ ID NO 156
<211> LENGTH: 20
<212> TYPE: PRT
<213> ORGANISM: Artificial Sequence
<220> FEATURE:
<223> OTHER INFORMATION: Synthetic peptide

<400> SEQUENCE: 156

Gln Ile Gln Val Leu Met Asp Lys Leu Val Glu Leu Thr His Gln Tyr
1               5                   10                  15

Lys Leu Lys Glu
            20

<210> SEQ ID NO 157
<211> LENGTH: 20
<212> TYPE: PRT
<213> ORGANISM: Artificial Sequence
<220> FEATURE:
<223> OTHER INFORMATION: Synthetic peptide

<400> SEQUENCE: 157

Tyr Lys Leu Lys Glu Thr Ile Gln Lys Leu Ser Asn Val Leu Gln Gln
1               5                   10                  15

Val Lys Ile Lys
```

<210> SEQ ID NO 158
<211> LENGTH: 20
<212> TYPE: PRT
<213> ORGANISM: Artificial Sequence
<220> FEATURE:
<223> OTHER INFORMATION: Synthetic peptide

<400> SEQUENCE: 158

Gln Val Lys Ile Lys Asp Tyr Phe Glu Lys Leu Val Gly Phe Ile Asp
1               5                   10                  15

Asp Ala Val Lys
            20

<210> SEQ ID NO 159
<211> LENGTH: 20
<212> TYPE: PRT
<213> ORGANISM: Artificial Sequence
<220> FEATURE:
<223> OTHER INFORMATION: Synthetic peptide

<400> SEQUENCE: 159

Asp Asp Ala Val Lys Lys Leu Asn Glu Leu Ser Phe Lys Thr Phe Ile
1               5                   10                  15

Glu Asp Val Asn
            20

<210> SEQ ID NO 160
<211> LENGTH: 20
<212> TYPE: PRT
<213> ORGANISM: Artificial Sequence
<220> FEATURE:
<223> OTHER INFORMATION: Synthetic peptide

<400> SEQUENCE: 160

Ile Glu Asp Val Asn Lys Phe Leu Asp Met Leu Ile Lys Lys Leu Lys
1               5                   10                  15

Ser Phe Asp Tyr
            20

<210> SEQ ID NO 161
<211> LENGTH: 20
<212> TYPE: PRT
<213> ORGANISM: Artificial Sequence
<220> FEATURE:
<223> OTHER INFORMATION: Synthetic peptide

<400> SEQUENCE: 161

Lys Ser Phe Asp Tyr His Gln Phe Val Asp Glu Thr Asn Asp Lys Ile
1               5                   10                  15

Arg Glu Val Thr
            20

<210> SEQ ID NO 162
<211> LENGTH: 20
<212> TYPE: PRT
<213> ORGANISM: Artificial Sequence
<220> FEATURE:
<223> OTHER INFORMATION: Synthetic peptide

<400> SEQUENCE: 162

Ile Arg Glu Val Thr Gln Arg Leu Asn Gly Glu Ile Gln Ala Leu Glu
1               5                   10                  15

-continued

Leu Pro Gln Lys
            20

<210> SEQ ID NO 163
<211> LENGTH: 20
<212> TYPE: PRT
<213> ORGANISM: Artificial Sequence
<220> FEATURE:
<223> OTHER INFORMATION: Synthetic peptide

<400> SEQUENCE: 163

Glu Leu Pro Gln Lys Ala Glu Ala Leu Lys Leu Phe Leu Glu Glu Thr
1               5                   10                  15

Lys Ala Thr Val
            20

<210> SEQ ID NO 164
<211> LENGTH: 20
<212> TYPE: PRT
<213> ORGANISM: Artificial Sequence
<220> FEATURE:
<223> OTHER INFORMATION: Synthetic peptide

<400> SEQUENCE: 164

Thr Lys Ala Thr Val Ala Val Tyr Leu Glu Ser Leu Gln Asp Thr Lys
1               5                   10                  15

Ile Thr Leu Ile
            20

<210> SEQ ID NO 165
<211> LENGTH: 20
<212> TYPE: PRT
<213> ORGANISM: Artificial Sequence
<220> FEATURE:
<223> OTHER INFORMATION: Synthetic peptide

<400> SEQUENCE: 165

Lys Ile Thr Leu Ile Ile Asn Trp Leu Gln Glu Ala Leu Ser Ser Ala
1               5                   10                  15

Ser Leu Ala His
            20

<210> SEQ ID NO 166
<211> LENGTH: 20
<212> TYPE: PRT
<213> ORGANISM: Artificial Sequence
<220> FEATURE:
<223> OTHER INFORMATION: Synthetic peptide

<400> SEQUENCE: 166

Ala Ser Leu Ala His Met Lys Ala Lys Phe Arg Glu Thr Leu Glu Asp
1               5                   10                  15

Thr Arg Asp Arg
            20

<210> SEQ ID NO 167
<211> LENGTH: 20
<212> TYPE: PRT
<213> ORGANISM: Artificial Sequence
<220> FEATURE:
<223> OTHER INFORMATION: Synthetic peptide

<400> SEQUENCE: 167

Asp Thr Arg Asp Arg Met Tyr Gln Met Asp Ile Gln Gln Glu Leu Gln
1               5                   10                  15

Arg Tyr Leu Ser
            20

<210> SEQ ID NO 168
<211> LENGTH: 20
<212> TYPE: PRT
<213> ORGANISM: Artificial Sequence
<220> FEATURE:
<223> OTHER INFORMATION: Synthetic peptide

<400> SEQUENCE: 168

Gln Arg Tyr Leu Ser Leu Val Gly Gln Val Tyr Ser Thr Leu Val Thr
1               5                   10                  15

Tyr Ile Ser Asp
            20

<210> SEQ ID NO 169
<211> LENGTH: 20
<212> TYPE: PRT
<213> ORGANISM: Artificial Sequence
<220> FEATURE:
<223> OTHER INFORMATION: Synthetic peptide

<400> SEQUENCE: 169

Thr Tyr Ile Ser Asp Trp Trp Thr Leu Ala Ala Lys Asn Leu Thr Asp
1               5                   10                  15

Phe Ala Glu Gln
            20

<210> SEQ ID NO 170
<211> LENGTH: 20
<212> TYPE: PRT
<213> ORGANISM: Artificial Sequence
<220> FEATURE:
<223> OTHER INFORMATION: Synthetic peptide

<400> SEQUENCE: 170

Asp Phe Ala Glu Gln Tyr Ser Ile Gln Asp Trp Ala Lys Arg Met Lys
1               5                   10                  15

Ala Leu Val Glu
            20

<210> SEQ ID NO 171
<211> LENGTH: 20
<212> TYPE: PRT
<213> ORGANISM: Artificial Sequence
<220> FEATURE:
<223> OTHER INFORMATION: Synthetic peptide

<400> SEQUENCE: 171

Lys Ala Leu Val Glu Gln Gly Phe Thr Val Pro Glu Ile Lys Thr Ile
1               5                   10                  15

Leu Gly Thr Met
            20

<210> SEQ ID NO 172
<211> LENGTH: 20
<212> TYPE: PRT
<213> ORGANISM: Artificial Sequence
<220> FEATURE:
<223> OTHER INFORMATION: Synthetic peptide

<400> SEQUENCE: 172

Ile Leu Gly Thr Met Pro Ala Phe Glu Val Ser Leu Gln Ala Leu Gln

```
1               5                   10                  15
Lys Ala Thr Phe
            20

<210> SEQ ID NO 173
<211> LENGTH: 20
<212> TYPE: PRT
<213> ORGANISM: Artificial Sequence
<220> FEATURE:
<223> OTHER INFORMATION: Synthetic peptide

<400> SEQUENCE: 173

Gln Lys Ala Thr Phe Gln Thr Pro Asp Phe Ile Val Pro Leu Thr Asp
1               5                   10                  15

Leu Arg Ile Pro
            20

<210> SEQ ID NO 174
<211> LENGTH: 20
<212> TYPE: PRT
<213> ORGANISM: Artificial Sequence
<220> FEATURE:
<223> OTHER INFORMATION: Synthetic peptide

<400> SEQUENCE: 174

Asp Leu Arg Ile Pro Ser Val Gln Ile Asn Phe Lys Asp Leu Lys Asn
1               5                   10                  15

Ile Lys Ile Pro
            20

<210> SEQ ID NO 175
<211> LENGTH: 20
<212> TYPE: PRT
<213> ORGANISM: Artificial Sequence
<220> FEATURE:
<223> OTHER INFORMATION: Synthetic peptide

<400> SEQUENCE: 175

Asn Ile Lys Ile Pro Ser Arg Phe Ser Thr Pro Glu Phe Thr Ile Leu
1               5                   10                  15

Asn Thr Phe His
            20

<210> SEQ ID NO 176
<211> LENGTH: 20
<212> TYPE: PRT
<213> ORGANISM: Artificial Sequence
<220> FEATURE:
<223> OTHER INFORMATION: Synthetic peptide

<400> SEQUENCE: 176

Leu Asn Thr Phe His Ile Pro Ser Phe Thr Ile Asp Phe Val Glu Met
1               5                   10                  15

Lys Val Lys Ile
            20

<210> SEQ ID NO 177
<211> LENGTH: 20
<212> TYPE: PRT
<213> ORGANISM: Artificial Sequence
<220> FEATURE:
<223> OTHER INFORMATION: Synthetic peptide

<400> SEQUENCE: 177
```

```
Met Lys Val Lys Ile Ile Arg Thr Ile Asp Gln Met Gln Asn Ser Glu
1               5                   10                  15

Leu Gln Trp Pro
            20

<210> SEQ ID NO 178
<211> LENGTH: 20
<212> TYPE: PRT
<213> ORGANISM: Artificial Sequence
<220> FEATURE:
<223> OTHER INFORMATION: Synthetic peptide

<400> SEQUENCE: 178

Glu Leu Gln Trp Pro Val Pro Asp Ile Tyr Leu Arg Asp Leu Lys Val
1               5                   10                  15

Glu Asp Ile Pro
            20

<210> SEQ ID NO 179
<211> LENGTH: 20
<212> TYPE: PRT
<213> ORGANISM: Artificial Sequence
<220> FEATURE:
<223> OTHER INFORMATION: Synthetic peptide

<400> SEQUENCE: 179

Val Glu Asp Ile Pro Leu Ala Arg Ile Thr Leu Pro Asp Phe Arg Leu
1               5                   10                  15

Pro Glu Ile Ala
            20

<210> SEQ ID NO 180
<211> LENGTH: 20
<212> TYPE: PRT
<213> ORGANISM: Artificial Sequence
<220> FEATURE:
<223> OTHER INFORMATION: Synthetic peptide

<400> SEQUENCE: 180

Leu Pro Glu Ile Ala Ile Pro Glu Phe Ile Ile Pro Thr Leu Asn Leu
1               5                   10                  15

Asn Asp Phe Gln
            20

<210> SEQ ID NO 181
<211> LENGTH: 20
<212> TYPE: PRT
<213> ORGANISM: Artificial Sequence
<220> FEATURE:
<223> OTHER INFORMATION: Synthetic peptide

<400> SEQUENCE: 181

Leu Asn Asp Phe Gln Val Pro Asp Leu His Ile Pro Glu Phe Gln Leu
1               5                   10                  15

Pro His Ile Ser
            20

<210> SEQ ID NO 182
<211> LENGTH: 20
<212> TYPE: PRT
<213> ORGANISM: Artificial Sequence
<220> FEATURE:
<223> OTHER INFORMATION: Synthetic peptide

<400> SEQUENCE: 182
```

```
Leu Pro His Ile Ser His Thr Ile Glu Val Pro Thr Phe Gly Lys Leu
1               5                   10                  15

Tyr Ser Ile Leu
            20

<210> SEQ ID NO 183
<211> LENGTH: 20
<212> TYPE: PRT
<213> ORGANISM: Artificial Sequence
<220> FEATURE:
<223> OTHER INFORMATION: Synthetic peptide

<400> SEQUENCE: 183

Leu Tyr Ser Ile Leu Lys Ile Gln Ser Pro Leu Phe Thr Leu Asp Ala
1               5                   10                  15

Asn Ala Asp Ile
            20

<210> SEQ ID NO 184
<211> LENGTH: 20
<212> TYPE: PRT
<213> ORGANISM: Artificial Sequence
<220> FEATURE:
<223> OTHER INFORMATION: Synthetic peptide

<400> SEQUENCE: 184

Ala Asn Ala Asp Ile Gly Asn Gly Thr Thr Ser Ala Asn Glu Ala Gly
1               5                   10                  15

Ile Ala Ala Ser
            20

<210> SEQ ID NO 185
<211> LENGTH: 20
<212> TYPE: PRT
<213> ORGANISM: Artificial Sequence
<220> FEATURE:
<223> OTHER INFORMATION: Synthetic peptide

<400> SEQUENCE: 185

Gly Ile Ala Ala Ser Ile Thr Ala Lys Gly Glu Ser Lys Leu Glu Val
1               5                   10                  15

Leu Asn Phe Asp
            20

<210> SEQ ID NO 186
<211> LENGTH: 20
<212> TYPE: PRT
<213> ORGANISM: Artificial Sequence
<220> FEATURE:
<223> OTHER INFORMATION: Synthetic peptide

<400> SEQUENCE: 186

Val Leu Asn Phe Asp Phe Gln Ala Asn Ala Gln Leu Ser Asn Pro Lys
1               5                   10                  15

Ile Asn Pro Leu
            20

<210> SEQ ID NO 187
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 187

Lys Ile Asn Pro Leu Ala Leu Lys Glu Ser Val Lys Phe Ser Ser Lys
1               5                   10                  15

Tyr Leu Arg Thr
            20

<210> SEQ ID NO 188
<211> LENGTH: 20
<212> TYPE: PRT
<213> ORGANISM: Artificial Sequence
<220> FEATURE:
<223> OTHER INFORMATION: Synthetic peptide

<400> SEQUENCE: 188

Lys Tyr Leu Arg Thr Glu His Gly Ser Glu Met Leu Phe Phe Gly Asn
1               5                   10                  15

Ala Ile Glu Gly
            20

<210> SEQ ID NO 189
<211> LENGTH: 20
<212> TYPE: PRT
<213> ORGANISM: Artificial Sequence
<220> FEATURE:
<223> OTHER INFORMATION: Synthetic peptide

<400> SEQUENCE: 189

Asn Ala Ile Glu Gly Lys Ser Asn Thr Val Ala Ser Leu His Thr Glu
1               5                   10                  15

Lys Asn Thr Leu
            20

<210> SEQ ID NO 190
<211> LENGTH: 20
<212> TYPE: PRT
<213> ORGANISM: Artificial Sequence
<220> FEATURE:
<223> OTHER INFORMATION: Synthetic peptide

<400> SEQUENCE: 190

Glu Lys Asn Thr Leu Glu Leu Ser Asn Gly Val Ile Val Lys Ile Asn
1               5                   10                  15

Asn Gln Leu Thr
            20

<210> SEQ ID NO 191
<211> LENGTH: 20
<212> TYPE: PRT
<213> ORGANISM: Artificial Sequence
<220> FEATURE:
<223> OTHER INFORMATION: Synthetic peptide

<400> SEQUENCE: 191

Asn Asn Gln Leu Thr Leu Asp Ser Asn Thr Lys Tyr Phe His Lys Leu
1               5                   10                  15

Asn Ile Pro Lys
            20

<210> SEQ ID NO 192
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 192

Leu Asn Ile Pro Lys Leu Asp Phe Ser Ser Gln Ala Asp Leu Arg Asn
1               5                   10                  15

Glu Ile Lys Thr
            20

<210> SEQ ID NO 193
<211> LENGTH: 20
<212> TYPE: PRT
<213> ORGANISM: Artificial Sequence
<220> FEATURE:
<223> OTHER INFORMATION: Synthetic peptide

<400> SEQUENCE: 193

Asn Glu Ile Lys Thr Leu Leu Lys Ala Gly His Ile Ala Trp Thr Ser
1               5                   10                  15

Ser Gly Lys Gly
            20

<210> SEQ ID NO 194
<211> LENGTH: 20
<212> TYPE: PRT
<213> ORGANISM: Artificial Sequence
<220> FEATURE:
<223> OTHER INFORMATION: Synthetic peptide

<400> SEQUENCE: 194

Ser Ser Gly Lys Gly Ser Trp Lys Trp Ala Cys Pro Arg Phe Ser Asp
1               5                   10                  15

Glu Gly Thr His
            20

<210> SEQ ID NO 195
<211> LENGTH: 20
<212> TYPE: PRT
<213> ORGANISM: Artificial Sequence
<220> FEATURE:
<223> OTHER INFORMATION: Synthetic peptide

<400> SEQUENCE: 195

Asp Glu Gly Thr His Glu Ser Gln Ile Ser Phe Thr Ile Glu Gly Pro
1               5                   10                  15

Leu Thr Ser Phe
            20

<210> SEQ ID NO 196
<211> LENGTH: 20
<212> TYPE: PRT
<213> ORGANISM: Artificial Sequence
<220> FEATURE:
<223> OTHER INFORMATION: Synthetic peptide

<400> SEQUENCE: 196

Pro Leu Thr Ser Phe Gly Leu Ser Asn Lys Ile Asn Ser Lys His Leu
1               5                   10                  15

Arg Val Asn Gln
            20

<210> SEQ ID NO 197
<211> LENGTH: 20
<212> TYPE: PRT
<213> ORGANISM: Artificial Sequence
<220> FEATURE:

```
<223> OTHER INFORMATION: Synthetic peptide

<400> SEQUENCE: 197

Leu Arg Val Asn Gln Asn Leu Val Tyr Glu Ser Gly Ser Leu Asn Phe
1               5                   10                  15

Ser Lys Leu Glu
            20

<210> SEQ ID NO 198
<211> LENGTH: 20
<212> TYPE: PRT
<213> ORGANISM: Artificial Sequence
<220> FEATURE:
<223> OTHER INFORMATION: Synthetic peptide

<400> SEQUENCE: 198

Phe Ser Lys Leu Glu Ile Gln Ser Gln Val Asp Ser Gln His Val Gly
1               5                   10                  15

His Ser Val Leu
            20

<210> SEQ ID NO 199
<211> LENGTH: 20
<212> TYPE: PRT
<213> ORGANISM: Artificial Sequence
<220> FEATURE:
<223> OTHER INFORMATION: Synthetic peptide

<400> SEQUENCE: 199

Gly His Ser Val Leu Thr Ala Lys Gly Met Ala Leu Phe Gly Glu Gly
1               5                   10                  15

Lys Ala Glu Phe
            20

<210> SEQ ID NO 200
<211> LENGTH: 20
<212> TYPE: PRT
<213> ORGANISM: Artificial Sequence
<220> FEATURE:
<223> OTHER INFORMATION: Synthetic peptide

<400> SEQUENCE: 200

Gly Lys Ala Glu Phe Thr Gly Arg His Asp Ala His Leu Asn Gly Lys
1               5                   10                  15

Val Ile Gly Thr
            20

<210> SEQ ID NO 201
<211> LENGTH: 20
<212> TYPE: PRT
<213> ORGANISM: Artificial Sequence
<220> FEATURE:
<223> OTHER INFORMATION: Synthetic peptide

<400> SEQUENCE: 201

Lys Val Ile Gly Thr Leu Lys Asn Ser Leu Phe Phe Ser Ala Gln Pro
1               5                   10                  15

Phe Glu Ile Thr
            20

<210> SEQ ID NO 202
<211> LENGTH: 20
<212> TYPE: PRT
<213> ORGANISM: Artificial Sequence
```

```
<220> FEATURE:
<223> OTHER INFORMATION: Synthetic peptide

<400> SEQUENCE: 202

Pro Phe Glu Ile Thr Ala Ser Thr Asn Asn Glu Gly Asn Leu Lys Val
1               5                   10                  15

Arg Phe Pro Leu
            20

<210> SEQ ID NO 203
<211> LENGTH: 20
<212> TYPE: PRT
<213> ORGANISM: Artificial Sequence
<220> FEATURE:
<223> OTHER INFORMATION: Synthetic peptide

<400> SEQUENCE: 203

Val Arg Phe Pro Leu Arg Leu Thr Gly Lys Ile Asp Phe Leu Asn Asn
1               5                   10                  15

Tyr Ala Leu Phe
            20

<210> SEQ ID NO 204
<211> LENGTH: 20
<212> TYPE: PRT
<213> ORGANISM: Artificial Sequence
<220> FEATURE:
<223> OTHER INFORMATION: Synthetic peptide

<400> SEQUENCE: 204

Asn Tyr Ala Leu Phe Leu Ser Pro Ser Ala Gln Gln Ala Ser Trp Gln
1               5                   10                  15

Val Ser Ala Arg
            20

<210> SEQ ID NO 205
<211> LENGTH: 20
<212> TYPE: PRT
<213> ORGANISM: Artificial Sequence
<220> FEATURE:
<223> OTHER INFORMATION: Synthetic peptide

<400> SEQUENCE: 205

Gln Val Ser Ala Arg Phe Asn Gln Tyr Lys Tyr Asn Gln Asn Phe Ser
1               5                   10                  15

Ala Gly Asn Asn
            20

<210> SEQ ID NO 206
<211> LENGTH: 20
<212> TYPE: PRT
<213> ORGANISM: Artificial Sequence
<220> FEATURE:
<223> OTHER INFORMATION: Synthetic peptide

<400> SEQUENCE: 206

Ser Ala Gly Asn Asn Glu Asn Ile Met Glu Ala His Val Gly Ile Asn
1               5                   10                  15

Gly Glu Ala Asn
            20

<210> SEQ ID NO 207
<211> LENGTH: 20
<212> TYPE: PRT
```

<213> ORGANISM: Artificial Sequence
<220> FEATURE:
<223> OTHER INFORMATION: Synthetic peptide

<400> SEQUENCE: 207

Asn Gly Glu Ala Asn Leu Asp Phe Leu Asn Ile Pro Leu Thr Ile Pro
1               5                   10                  15

Glu Met Arg Leu
            20

<210> SEQ ID NO 208
<211> LENGTH: 20
<212> TYPE: PRT
<213> ORGANISM: Artificial Sequence
<220> FEATURE:
<223> OTHER INFORMATION: Synthetic peptide

<400> SEQUENCE: 208

Pro Glu Met Arg Leu Pro Tyr Thr Ile Ile Thr Thr Pro Pro Leu Lys
1               5                   10                  15

Asp Phe Ser Leu
            20

<210> SEQ ID NO 209
<211> LENGTH: 20
<212> TYPE: PRT
<213> ORGANISM: Artificial Sequence
<220> FEATURE:
<223> OTHER INFORMATION: Synthetic peptide

<400> SEQUENCE: 209

Lys Asp Phe Ser Leu Trp Glu Lys Thr Gly Leu Lys Glu Phe Leu Lys
1               5                   10                  15

Thr Thr Lys Gln
            20

<210> SEQ ID NO 210
<211> LENGTH: 20
<212> TYPE: PRT
<213> ORGANISM: Artificial Sequence
<220> FEATURE:
<223> OTHER INFORMATION: Synthetic peptide

<400> SEQUENCE: 210

Lys Thr Thr Lys Gln Ser Phe Asp Leu Ser Val Lys Ala Gln Tyr Lys
1               5                   10                  15

Lys Asn Lys His
            20

<210> SEQ ID NO 211
<211> LENGTH: 20
<212> TYPE: PRT
<213> ORGANISM: Artificial Sequence
<220> FEATURE:
<223> OTHER INFORMATION: Synthetic peptide

<400> SEQUENCE: 211

Lys Lys Asn Lys His Arg His Ser Ile Thr Asn Pro Leu Ala Val Leu
1               5                   10                  15

Cys Glu Phe Ile
            20

<210> SEQ ID NO 212
<211> LENGTH: 20

```
<212> TYPE: PRT
<213> ORGANISM: Artificial Sequence
<220> FEATURE:
<223> OTHER INFORMATION: Synthetic peptide

<400> SEQUENCE: 212

Leu Cys Glu Phe Ile Ser Gln Ser Ile Lys Ser Phe Asp Arg His Phe
1               5                   10                  15

Glu Lys Asn Arg
            20

<210> SEQ ID NO 213
<211> LENGTH: 20
<212> TYPE: PRT
<213> ORGANISM: Artificial Sequence
<220> FEATURE:
<223> OTHER INFORMATION: Synthetic peptide

<400> SEQUENCE: 213

Phe Glu Lys Asn Arg Asn Asn Ala Leu Asp Phe Val Thr Lys Ser Tyr
1               5                   10                  15

Asn Glu Thr Lys
            20

<210> SEQ ID NO 214
<211> LENGTH: 20
<212> TYPE: PRT
<213> ORGANISM: Artificial Sequence
<220> FEATURE:
<223> OTHER INFORMATION: Synthetic peptide

<400> SEQUENCE: 214

Tyr Asn Glu Thr Lys Ile Lys Phe Asp Lys Tyr Lys Ala Glu Lys Ser
1               5                   10                  15

His Asp Glu Leu
            20

<210> SEQ ID NO 215
<211> LENGTH: 20
<212> TYPE: PRT
<213> ORGANISM: Artificial Sequence
<220> FEATURE:
<223> OTHER INFORMATION: Synthetic peptide

<400> SEQUENCE: 215

Ser His Asp Glu Leu Pro Arg Thr Phe Gln Ile Pro Gly Tyr Thr Val
1               5                   10                  15

Pro Val Val Asn
            20

<210> SEQ ID NO 216
<211> LENGTH: 20
<212> TYPE: PRT
<213> ORGANISM: Artificial Sequence
<220> FEATURE:
<223> OTHER INFORMATION: Synthetic peptide

<400> SEQUENCE: 216

Val Pro Val Val Asn Val Glu Val Ser Pro Phe Thr Ile Glu Met Ser
1               5                   10                  15

Ala Phe Gly Tyr
            20

<210> SEQ ID NO 217
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 217

Ser Ala Phe Gly Tyr Val Phe Pro Lys Ala Val Ser Met Pro Ser Phe
1               5                   10                  15

Ser Ile Leu Gly
            20

<210> SEQ ID NO 218
<211> LENGTH: 20
<212> TYPE: PRT
<213> ORGANISM: Artificial Sequence
<220> FEATURE:
<223> OTHER INFORMATION: Synthetic peptide

<400> SEQUENCE: 218

Phe Ser Ile Leu Gly Ser Asp Val Arg Val Pro Ser Tyr Thr Leu Ile
1               5                   10                  15

Leu Pro Ser Leu
            20

<210> SEQ ID NO 219
<211> LENGTH: 20
<212> TYPE: PRT
<213> ORGANISM: Artificial Sequence
<220> FEATURE:
<223> OTHER INFORMATION: Synthetic peptide

<400> SEQUENCE: 219

Ile Leu Pro Ser Leu Glu Leu Pro Val Leu His Val Pro Arg Asn Leu
1               5                   10                  15

Lys Leu Ser Leu
            20

<210> SEQ ID NO 220
<211> LENGTH: 20
<212> TYPE: PRT
<213> ORGANISM: Artificial Sequence
<220> FEATURE:
<223> OTHER INFORMATION: Synthetic peptide

<400> SEQUENCE: 220

Leu Lys Leu Ser Leu Pro His Phe Lys Glu Leu Cys Thr Ile Ser His
1               5                   10                  15

Ile Phe Ile Pro
            20

<210> SEQ ID NO 221
<211> LENGTH: 20
<212> TYPE: PRT
<213> ORGANISM: Artificial Sequence
<220> FEATURE:
<223> OTHER INFORMATION: Synthetic peptide

<400> SEQUENCE: 221

His Ile Phe Ile Pro Ala Met Gly Asn Ile Thr Tyr Asp Phe Ser Phe
1               5                   10                  15

Lys Ser Ser Val
            20
```

<210> SEQ ID NO 222
<211> LENGTH: 20
<212> TYPE: PRT
<213> ORGANISM: Artificial Sequence
<220> FEATURE:
<223> OTHER INFORMATION: Synthetic peptide

<400> SEQUENCE: 222

Phe Lys Ser Ser Val Ile Thr Leu Asn Thr Asn Ala Glu Leu Phe Asn
1               5                   10                  15

Gln Ser Asp Ile
            20

<210> SEQ ID NO 223
<211> LENGTH: 20
<212> TYPE: PRT
<213> ORGANISM: Artificial Sequence
<220> FEATURE:
<223> OTHER INFORMATION: Synthetic peptide

<400> SEQUENCE: 223

Asn Gln Ser Asp Ile Val Ala His Leu Leu Ser Ser Ser Ser Val
1               5                   10                  15

Ile Asp Ala Leu
            20

<210> SEQ ID NO 224
<211> LENGTH: 20
<212> TYPE: PRT
<213> ORGANISM: Artificial Sequence
<220> FEATURE:
<223> OTHER INFORMATION: Synthetic peptide

<400> SEQUENCE: 224

Val Ile Asp Ala Leu Gln Tyr Lys Leu Glu Gly Thr Thr Arg Leu Thr
1               5                   10                  15

Arg Lys Arg Gly
            20

<210> SEQ ID NO 225
<211> LENGTH: 20
<212> TYPE: PRT
<213> ORGANISM: Artificial Sequence
<220> FEATURE:
<223> OTHER INFORMATION: Synthetic peptide

<400> SEQUENCE: 225

Thr Arg Lys Arg Gly Leu Lys Leu Ala Thr Ala Leu Ser Leu Ser Asn
1               5                   10                  15

Lys Phe Val Glu
            20

<210> SEQ ID NO 226
<211> LENGTH: 20
<212> TYPE: PRT
<213> ORGANISM: Artificial Sequence
<220> FEATURE:
<223> OTHER INFORMATION: Synthetic peptide

<400> SEQUENCE: 226

Asn Lys Phe Val Glu Gly Ser His Asn Ser Thr Val Ser Leu Thr Thr
1               5                   10                  15

Lys Asn Met Glu
            20

```
<210> SEQ ID NO 227
<211> LENGTH: 20
<212> TYPE: PRT
<213> ORGANISM: Artificial Sequence
<220> FEATURE:
<223> OTHER INFORMATION: Synthetic peptide

<400> SEQUENCE: 227

Thr Lys Asn Met Glu Val Ser Val Ala Lys Thr Thr Lys Ala Glu Ile
1               5                   10                  15

Pro Ile Leu Arg
            20

<210> SEQ ID NO 228
<211> LENGTH: 20
<212> TYPE: PRT
<213> ORGANISM: Artificial Sequence
<220> FEATURE:
<223> OTHER INFORMATION: Synthetic peptide

<400> SEQUENCE: 228

Ile Pro Ile Leu Arg Met Asn Phe Lys Gln Glu Leu Asn Gly Asn Thr
1               5                   10                  15

Lys Ser Lys Pro
            20

<210> SEQ ID NO 229
<211> LENGTH: 20
<212> TYPE: PRT
<213> ORGANISM: Artificial Sequence
<220> FEATURE:
<223> OTHER INFORMATION: Synthetic peptide

<400> SEQUENCE: 229

Thr Lys Ser Lys Pro Thr Val Ser Ser Met Glu Phe Lys Tyr Asp
1               5                   10                  15

Phe Asn Ser Ser
            20

<210> SEQ ID NO 230
<211> LENGTH: 20
<212> TYPE: PRT
<213> ORGANISM: Artificial Sequence
<220> FEATURE:
<223> OTHER INFORMATION: Synthetic peptide

<400> SEQUENCE: 230

Asp Phe Asn Ser Ser Met Leu Tyr Ser Thr Ala Lys Gly Ala Val Asp
1               5                   10                  15

His Lys Leu Ser
            20

<210> SEQ ID NO 231
<211> LENGTH: 20
<212> TYPE: PRT
<213> ORGANISM: Artificial Sequence
<220> FEATURE:
<223> OTHER INFORMATION: Synthetic peptide

<400> SEQUENCE: 231

Asp His Lys Leu Ser Leu Glu Ser Leu Thr Ser Tyr Phe Ser Ile Glu
1               5                   10                  15

Ser Ser Thr Lys
            20
```

<210> SEQ ID NO 232
<211> LENGTH: 20
<212> TYPE: PRT
<213> ORGANISM: Artificial Sequence
<220> FEATURE:
<223> OTHER INFORMATION: Synthetic peptide

<400> SEQUENCE: 232

Glu Ser Ser Thr Lys Gly Asp Val Lys Gly Ser Val Leu Ser Arg Glu
1               5                   10                  15

Tyr Ser Gly Thr
            20

<210> SEQ ID NO 233
<211> LENGTH: 20
<212> TYPE: PRT
<213> ORGANISM: Artificial Sequence
<220> FEATURE:
<223> OTHER INFORMATION: Synthetic peptide

<400> SEQUENCE: 233

Glu Tyr Ser Gly Thr Ile Ala Ser Glu Ala Asn Thr Tyr Leu Asn Ser
1               5                   10                  15

Lys Ser Thr Arg
            20

<210> SEQ ID NO 234
<211> LENGTH: 20
<212> TYPE: PRT
<213> ORGANISM: Artificial Sequence
<220> FEATURE:
<223> OTHER INFORMATION: Synthetic peptide

<400> SEQUENCE: 234

Ser Lys Ser Thr Arg Ser Ser Val Lys Leu Gln Gly Thr Ser Lys Ile
1               5                   10                  15

Asp Asp Ile Trp
            20

<210> SEQ ID NO 235
<211> LENGTH: 20
<212> TYPE: PRT
<213> ORGANISM: Artificial Sequence
<220> FEATURE:
<223> OTHER INFORMATION: Synthetic peptide

<400> SEQUENCE: 235

Ile Asp Asp Ile Trp Asn Leu Glu Val Lys Glu Asn Phe Ala Gly Glu
1               5                   10                  15

Ala Thr Leu Gln
            20

<210> SEQ ID NO 236
<211> LENGTH: 20
<212> TYPE: PRT
<213> ORGANISM: Artificial Sequence
<220> FEATURE:
<223> OTHER INFORMATION: Synthetic peptide

<400> SEQUENCE: 236

Glu Ala Thr Leu Gln Arg Ile Tyr Ser Leu Trp Glu His Ser Thr Lys
1               5                   10                  15

Asn His Leu Gln

20

<210> SEQ ID NO 237
<211> LENGTH: 20
<212> TYPE: PRT
<213> ORGANISM: Artificial Sequence
<220> FEATURE:
<223> OTHER INFORMATION: Synthetic peptide

<400> SEQUENCE: 237

Lys Asn His Leu Gln Leu Glu Gly Leu Phe Phe Thr Asn Gly Glu His
1               5                   10                  15

Thr Ser Lys Ala
            20

<210> SEQ ID NO 238
<211> LENGTH: 20
<212> TYPE: PRT
<213> ORGANISM: Artificial Sequence
<220> FEATURE:
<223> OTHER INFORMATION: Synthetic peptide

<400> SEQUENCE: 238

His Thr Ser Lys Ala Thr Leu Glu Leu Ser Pro Trp Gln Met Ser Ala
1               5                   10                  15

Leu Val Gln Val
            20

<210> SEQ ID NO 239
<211> LENGTH: 20
<212> TYPE: PRT
<213> ORGANISM: Artificial Sequence
<220> FEATURE:
<223> OTHER INFORMATION: Synthetic peptide

<400> SEQUENCE: 239

Ala Leu Val Gln Val His Ala Ser Gln Pro Ser Ser Phe His Asp Phe
1               5                   10                  15

Pro Asp Leu Gly
            20

<210> SEQ ID NO 240
<211> LENGTH: 20
<212> TYPE: PRT
<213> ORGANISM: Artificial Sequence
<220> FEATURE:
<223> OTHER INFORMATION: Synthetic peptide

<400> SEQUENCE: 240

Phe Pro Asp Leu Gly Gln Glu Val Ala Leu Asn Ala Asn Thr Lys Asn
1               5                   10                  15

Gln Lys Ile Arg
            20

<210> SEQ ID NO 241
<211> LENGTH: 20
<212> TYPE: PRT
<213> ORGANISM: Artificial Sequence
<220> FEATURE:
<223> OTHER INFORMATION: Synthetic peptide

<400> SEQUENCE: 241

Asn Gln Lys Ile Arg Trp Lys Asn Glu Val Arg Ile His Ser Gly Ser
1               5                   10                  15

Phe Gln Ser Gln
            20

<210> SEQ ID NO 242
<211> LENGTH: 20
<212> TYPE: PRT
<213> ORGANISM: Artificial Sequence
<220> FEATURE:
<223> OTHER INFORMATION: Synthetic peptide

<400> SEQUENCE: 242

Ser Phe Gln Ser Gln Val Glu Leu Ser Asn Asp Gln Glu Lys Ala His
1               5                   10                  15

Leu Asp Ile Ala
            20

<210> SEQ ID NO 243
<211> LENGTH: 20
<212> TYPE: PRT
<213> ORGANISM: Artificial Sequence
<220> FEATURE:
<223> OTHER INFORMATION: Synthetic peptide

<400> SEQUENCE: 243

His Leu Asp Ile Ala Gly Ser Leu Glu Gly His Leu Arg Phe Leu Lys
1               5                   10                  15

Asn Ile Ile Leu
            20

<210> SEQ ID NO 244
<211> LENGTH: 20
<212> TYPE: PRT
<213> ORGANISM: Artificial Sequence
<220> FEATURE:
<223> OTHER INFORMATION: Synthetic peptide

<400> SEQUENCE: 244

Lys Asn Ile Ile Leu Pro Val Tyr Asp Lys Ser Leu Trp Asp Phe Leu
1               5                   10                  15

Lys Leu Asp Val
            20

<210> SEQ ID NO 245
<211> LENGTH: 20
<212> TYPE: PRT
<213> ORGANISM: Artificial Sequence
<220> FEATURE:
<223> OTHER INFORMATION: Synthetic peptide

<400> SEQUENCE: 245

Leu Lys Leu Asp Val Thr Thr Ser Ile Gly Arg Arg Gln His Leu Arg
1               5                   10                  15

Val Ser Thr Ala
            20

<210> SEQ ID NO 246
<211> LENGTH: 20
<212> TYPE: PRT
<213> ORGANISM: Artificial Sequence
<220> FEATURE:
<223> OTHER INFORMATION: Synthetic peptide

<400> SEQUENCE: 246

Arg Val Ser Thr Ala Phe Val Tyr Thr Lys Asn Pro Asn Gly Tyr Ser
1               5                   10                  15

Phe Ser Ile Pro
            20

<210> SEQ ID NO 247
<211> LENGTH: 20
<212> TYPE: PRT
<213> ORGANISM: Artificial Sequence
<220> FEATURE:
<223> OTHER INFORMATION: Synthetic peptide

<400> SEQUENCE: 247

Ser Phe Ser Ile Pro Val Lys Val Leu Ala Asp Lys Phe Ile Thr Pro
1               5                   10                  15

Gly Leu Lys Leu
            20

<210> SEQ ID NO 248
<211> LENGTH: 20
<212> TYPE: PRT
<213> ORGANISM: Artificial Sequence
<220> FEATURE:
<223> OTHER INFORMATION: Synthetic peptide

<400> SEQUENCE: 248

Pro Gly Leu Lys Leu Asn Asp Leu Asn Ser Val Leu Val Met Pro Thr
1               5                   10                  15

Phe His Val Pro
            20

<210> SEQ ID NO 249
<211> LENGTH: 20
<212> TYPE: PRT
<213> ORGANISM: Artificial Sequence
<220> FEATURE:
<223> OTHER INFORMATION: Synthetic peptide

<400> SEQUENCE: 249

Thr Phe His Val Pro Phe Thr Asp Leu Gln Val Pro Ser Cys Lys Leu
1               5                   10                  15

Asp Phe Arg Glu
            20

<210> SEQ ID NO 250
<211> LENGTH: 20
<212> TYPE: PRT
<213> ORGANISM: Artificial Sequence
<220> FEATURE:
<223> OTHER INFORMATION: Synthetic peptide

<400> SEQUENCE: 250

Leu Asp Phe Arg Glu Ile Gln Ile Tyr Lys Lys Leu Arg Thr Ser Ser
1               5                   10                  15

Phe Ala Leu Asn
            20

<210> SEQ ID NO 251
<211> LENGTH: 20
<212> TYPE: PRT
<213> ORGANISM: Artificial Sequence
<220> FEATURE:
<223> OTHER INFORMATION: Synthetic peptide

<400> SEQUENCE: 251

Ser Phe Ala Leu Asn Leu Pro Thr Leu Pro Glu Val Lys Phe Pro Glu

```
1               5                   10                  15

Val Asp Val Leu
            20

<210> SEQ ID NO 252
<211> LENGTH: 20
<212> TYPE: PRT
<213> ORGANISM: Artificial Sequence
<220> FEATURE:
<223> OTHER INFORMATION: Synthetic peptide

<400> SEQUENCE: 252

Glu Val Asp Val Leu Thr Lys Tyr Ser Gln Pro Glu Asp Ser Leu Ile
1               5                   10                  15

Pro Phe Phe Glu
            20

<210> SEQ ID NO 253
<211> LENGTH: 20
<212> TYPE: PRT
<213> ORGANISM: Artificial Sequence
<220> FEATURE:
<223> OTHER INFORMATION: Synthetic peptide

<400> SEQUENCE: 253

Ile Pro Phe Phe Glu Ile Thr Val Pro Glu Ser Gln Leu Thr Val Ser
1               5                   10                  15

Gln Phe Thr Leu
            20

<210> SEQ ID NO 254
<211> LENGTH: 20
<212> TYPE: PRT
<213> ORGANISM: Artificial Sequence
<220> FEATURE:
<223> OTHER INFORMATION: Synthetic peptide

<400> SEQUENCE: 254

Ser Gln Phe Thr Leu Pro Lys Ser Val Ser Asp Gly Ile Ala Ala Leu
1               5                   10                  15

Asp Leu Asn Ala
            20

<210> SEQ ID NO 255
<211> LENGTH: 20
<212> TYPE: PRT
<213> ORGANISM: Artificial Sequence
<220> FEATURE:
<223> OTHER INFORMATION: Synthetic peptide

<400> SEQUENCE: 255

Leu Asp Leu Asn Ala Val Ala Asn Lys Ile Ala Asp Phe Glu Leu Pro
1               5                   10                  15

Thr Ile Ile Val
            20

<210> SEQ ID NO 256
<211> LENGTH: 20
<212> TYPE: PRT
<213> ORGANISM: Artificial Sequence
<220> FEATURE:
<223> OTHER INFORMATION: Synthetic peptide

<400> SEQUENCE: 256
```

```
Pro Thr Ile Ile Val Pro Glu Gln Thr Ile Glu Ile Pro Ser Ile Lys
1               5                   10                  15

Phe Ser Val Pro
            20
```

<210> SEQ ID NO 257
<211> LENGTH: 20
<212> TYPE: PRT
<213> ORGANISM: Artificial Sequence
<220> FEATURE:
<223> OTHER INFORMATION: Synthetic peptide

<400> SEQUENCE: 257

```
Lys Phe Ser Val Pro Ala Gly Ile Val Ile Pro Ser Phe Gln Ala Leu
1               5                   10                  15

Thr Ala Arg Phe
            20
```

<210> SEQ ID NO 258
<211> LENGTH: 20
<212> TYPE: PRT
<213> ORGANISM: Artificial Sequence
<220> FEATURE:
<223> OTHER INFORMATION: Synthetic peptide

<400> SEQUENCE: 258

```
Leu Thr Ala Arg Phe Glu Val Asp Ser Pro Val Tyr Asn Ala Thr Trp
1               5                   10                  15

Ser Ala Ser Leu
            20
```

<210> SEQ ID NO 259
<211> LENGTH: 20
<212> TYPE: PRT
<213> ORGANISM: Artificial Sequence
<220> FEATURE:
<223> OTHER INFORMATION: Synthetic peptide

<400> SEQUENCE: 259

```
Trp Ser Ala Ser Leu Lys Asn Lys Ala Asp Tyr Val Glu Thr Val Leu
1               5                   10                  15

Asp Ser Thr Cys
            20
```

<210> SEQ ID NO 260
<211> LENGTH: 20
<212> TYPE: PRT
<213> ORGANISM: Artificial Sequence
<220> FEATURE:
<223> OTHER INFORMATION: Synthetic peptide

<400> SEQUENCE: 260

```
Leu Asp Ser Thr Cys Ser Ser Thr Val Gln Phe Leu Glu Tyr Glu Leu
1               5                   10                  15

Asn Val Leu Gly
            20
```

<210> SEQ ID NO 261
<211> LENGTH: 20
<212> TYPE: PRT
<213> ORGANISM: Artificial Sequence
<220> FEATURE:
<223> OTHER INFORMATION: Synthetic peptide

<400> SEQUENCE: 261

```
Leu Asn Val Leu Gly Thr His Lys Ile Glu Asp Gly Thr Leu Ala Ser
1               5                   10                  15

Lys Thr Lys Gly
            20
```

<210> SEQ ID NO 262
<211> LENGTH: 20
<212> TYPE: PRT
<213> ORGANISM: Artificial Sequence
<220> FEATURE:
<223> OTHER INFORMATION: Synthetic peptide

<400> SEQUENCE: 262

```
Ser Lys Thr Lys Gly Thr Leu Ala His Arg Asp Phe Ser Ala Glu Tyr
1               5                   10                  15

Glu Glu Asp Gly
            20
```

<210> SEQ ID NO 263
<211> LENGTH: 20
<212> TYPE: PRT
<213> ORGANISM: Artificial Sequence
<220> FEATURE:
<223> OTHER INFORMATION: Synthetic peptide

<400> SEQUENCE: 263

```
Tyr Glu Glu Asp Gly Lys Phe Glu Gly Leu Gln Glu Trp Glu Gly Lys
1               5                   10                  15

Ala His Leu Asn
            20
```

<210> SEQ ID NO 264
<211> LENGTH: 20
<212> TYPE: PRT
<213> ORGANISM: Artificial Sequence
<220> FEATURE:
<223> OTHER INFORMATION: Synthetic peptide

<400> SEQUENCE: 264

```
Lys Ala His Leu Asn Ile Lys Ser Pro Ala Phe Thr Asp Leu His Leu
1               5                   10                  15

Arg Tyr Gln Lys
            20
```

<210> SEQ ID NO 265
<211> LENGTH: 20
<212> TYPE: PRT
<213> ORGANISM: Artificial Sequence
<220> FEATURE:
<223> OTHER INFORMATION: Synthetic peptide

<400> SEQUENCE: 265

```
Leu Arg Tyr Gln Lys Asp Lys Lys Gly Ile Ser Thr Ser Ala Ala Ser
1               5                   10                  15

Pro Ala Val Gly
            20
```

<210> SEQ ID NO 266
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 266

Ser Pro Ala Val Gly Thr Val Gly Met Asp Met Asp Glu Asp Asp
1               5                   10                  15

Phe Ser Lys Trp
            20

<210> SEQ ID NO 267
<211> LENGTH: 20
<212> TYPE: PRT
<213> ORGANISM: Artificial Sequence
<220> FEATURE:
<223> OTHER INFORMATION: Synthetic peptide

<400> SEQUENCE: 267

Asp Phe Ser Lys Trp Asn Phe Tyr Tyr Ser Pro Gln Ser Ser Pro Asp
1               5                   10                  15

Lys Lys Leu Thr
            20

<210> SEQ ID NO 268
<211> LENGTH: 20
<212> TYPE: PRT
<213> ORGANISM: Artificial Sequence
<220> FEATURE:
<223> OTHER INFORMATION: Synthetic peptide

<400> SEQUENCE: 268

Asp Lys Lys Leu Thr Ile Phe Lys Thr Glu Leu Arg Val Arg Glu Ser
1               5                   10                  15

Asp Glu Glu Thr
            20

<210> SEQ ID NO 269
<211> LENGTH: 20
<212> TYPE: PRT
<213> ORGANISM: Artificial Sequence
<220> FEATURE:
<223> OTHER INFORMATION: Synthetic peptide

<400> SEQUENCE: 269

Ser Asp Glu Glu Thr Gln Ile Lys Val Asn Trp Glu Glu Glu Ala Ala
1               5                   10                  15

Ser Gly Leu Leu
            20

<210> SEQ ID NO 270
<211> LENGTH: 20
<212> TYPE: PRT
<213> ORGANISM: Artificial Sequence
<220> FEATURE:
<223> OTHER INFORMATION: Synthetic peptide

<400> SEQUENCE: 270

Ala Ser Gly Leu Leu Thr Ser Leu Lys Asp Asn Val Pro Lys Ala Thr
1               5                   10                  15

Gly Val Leu Tyr
            20

<210> SEQ ID NO 271
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 271

Thr Gly Val Leu Tyr Asp Tyr Val Asn Lys Tyr His Trp Glu His Thr
1               5                   10                  15

Gly Leu Thr Leu
            20

<210> SEQ ID NO 272
<211> LENGTH: 20
<212> TYPE: PRT
<213> ORGANISM: Artificial Sequence
<220> FEATURE:
<223> OTHER INFORMATION: Synthetic peptide

<400> SEQUENCE: 272

Thr Gly Leu Thr Leu Arg Glu Val Ser Ser Lys Leu Arg Arg Asn Leu
1               5                   10                  15

Gln Asn Asn Ala
            20

<210> SEQ ID NO 273
<211> LENGTH: 20
<212> TYPE: PRT
<213> ORGANISM: Artificial Sequence
<220> FEATURE:
<223> OTHER INFORMATION: Synthetic peptide

<400> SEQUENCE: 273

Leu Gln Asn Asn Ala Glu Trp Val Tyr Gln Gly Ala Ile Arg Gln Ile
1               5                   10                  15

Asp Asp Ile Asp
            20

<210> SEQ ID NO 274
<211> LENGTH: 20
<212> TYPE: PRT
<213> ORGANISM: Artificial Sequence
<220> FEATURE:
<223> OTHER INFORMATION: Synthetic peptide

<400> SEQUENCE: 274

Ile Asp Asp Ile Asp Val Arg Phe Gln Lys Ala Ala Ser Gly Thr Thr
1               5                   10                  15

Gly Thr Tyr Gln
            20

<210> SEQ ID NO 275
<211> LENGTH: 20
<212> TYPE: PRT
<213> ORGANISM: Artificial Sequence
<220> FEATURE:
<223> OTHER INFORMATION: Synthetic peptide

<400> SEQUENCE: 275

Thr Gly Thr Tyr Gln Glu Trp Lys Asp Lys Ala Gln Asn Leu Tyr Gln
1               5                   10                  15

Glu Leu Leu Thr
            20

<210> SEQ ID NO 276
<211> LENGTH: 20
<212> TYPE: PRT
<213> ORGANISM: Artificial Sequence
<220> FEATURE:
```

<223> OTHER INFORMATION: Synthetic peptide

<400> SEQUENCE: 276

Gln Glu Leu Leu Thr Gln Glu Gly Gln Ala Ser Phe Gln Gly Leu Lys
1               5                   10                  15

Asp Asn Val Phe
            20

<210> SEQ ID NO 277
<211> LENGTH: 20
<212> TYPE: PRT
<213> ORGANISM: Artificial Sequence
<220> FEATURE:
<223> OTHER INFORMATION: Synthetic peptide

<400> SEQUENCE: 277

Lys Asp Asn Val Phe Asp Gly Leu Val Arg Val Thr Gln Lys Phe His
1               5                   10                  15

Met Lys Val Lys
            20

<210> SEQ ID NO 278
<211> LENGTH: 20
<212> TYPE: PRT
<213> ORGANISM: Artificial Sequence
<220> FEATURE:
<223> OTHER INFORMATION: Synthetic peptide

<400> SEQUENCE: 278

His Met Lys Val Lys His Leu Ile Asp Ser Leu Ile Asp Phe Leu Asn
1               5                   10                  15

Phe Pro Arg Phe
            20

<210> SEQ ID NO 279
<211> LENGTH: 20
<212> TYPE: PRT
<213> ORGANISM: Artificial Sequence
<220> FEATURE:
<223> OTHER INFORMATION: Synthetic peptide

<400> SEQUENCE: 279

Asn Phe Pro Arg Phe Gln Phe Pro Gly Lys Pro Gly Ile Tyr Thr Arg
1               5                   10                  15

Glu Glu Leu Cys
            20

<210> SEQ ID NO 280
<211> LENGTH: 20
<212> TYPE: PRT
<213> ORGANISM: Artificial Sequence
<220> FEATURE:
<223> OTHER INFORMATION: Synthetic peptide

<400> SEQUENCE: 280

Arg Glu Glu Leu Cys Thr Met Phe Ile Arg Glu Val Gly Thr Val Leu
1               5                   10                  15

Ser Gln Val Tyr
            20

<210> SEQ ID NO 281
<211> LENGTH: 20
<212> TYPE: PRT
<213> ORGANISM: Artificial Sequence
<220> FEATURE:
<223> OTHER INFORMATION: Synthetic peptide

<400> SEQUENCE: 281

Leu Ser Gln Val Tyr Ser Lys Val His Asn Gly Ser Glu Ile Leu Phe
1               5                   10                  15

Ser Tyr Phe Gln
            20

<210> SEQ ID NO 282
<211> LENGTH: 20
<212> TYPE: PRT
<213> ORGANISM: Artificial Sequence
<220> FEATURE:
<223> OTHER INFORMATION: Synthetic peptide

<400> SEQUENCE: 282

Phe Ser Tyr Phe Gln Asp Leu Val Ile Thr Leu Pro Phe Glu Leu Arg
1               5                   10                  15

Lys His Lys Leu
            20

<210> SEQ ID NO 283
<211> LENGTH: 20
<212> TYPE: PRT
<213> ORGANISM: Artificial Sequence
<220> FEATURE:
<223> OTHER INFORMATION: Synthetic peptide

<400> SEQUENCE: 283

Arg Lys His Lys Leu Ile Asp Val Ile Ser Met Tyr Arg Glu Leu Leu
1               5                   10                  15

Lys Asp Leu Ser
            20

<210> SEQ ID NO 284
<211> LENGTH: 20
<212> TYPE: PRT
<213> ORGANISM: Artificial Sequence
<220> FEATURE:
<223> OTHER INFORMATION: Synthetic peptide

<400> SEQUENCE: 284

Leu Lys Asp Leu Ser Lys Glu Ala Gln Glu Val Phe Lys Ala Ile Gln
1               5                   10                  15

Ser Leu Lys Thr
            20

<210> SEQ ID NO 285
<211> LENGTH: 20
<212> TYPE: PRT
<213> ORGANISM: Artificial Sequence
<220> FEATURE:
<223> OTHER INFORMATION: Synthetic peptide

<400> SEQUENCE: 285

Gln Ser Leu Lys Thr Thr Glu Val Leu Arg Asn Leu Gln Asp Leu Leu
1               5                   10                  15

Gln Phe Ile Phe
            20

<210> SEQ ID NO 286
<211> LENGTH: 20
<212> TYPE: PRT

<213> ORGANISM: Artificial Sequence
<220> FEATURE:
<223> OTHER INFORMATION: Synthetic peptide

<400> SEQUENCE: 286

Leu Gln Phe Ile Phe Gln Leu Ile Glu Asp Asn Ile Lys Gln Leu Lys
1               5                   10                  15

Glu Met Lys Phe
            20

<210> SEQ ID NO 287
<211> LENGTH: 20
<212> TYPE: PRT
<213> ORGANISM: Artificial Sequence
<220> FEATURE:
<223> OTHER INFORMATION: Synthetic peptide

<400> SEQUENCE: 287

Lys Glu Met Lys Phe Thr Tyr Leu Ile Asn Tyr Ile Gln Asp Glu Ile
1               5                   10                  15

Asn Thr Ile Phe
            20

<210> SEQ ID NO 288
<211> LENGTH: 20
<212> TYPE: PRT
<213> ORGANISM: Artificial Sequence
<220> FEATURE:
<223> OTHER INFORMATION: Synthetic peptide

<400> SEQUENCE: 288

Ile Asn Thr Ile Phe Asn Asp Tyr Ile Pro Tyr Val Phe Lys Leu Leu
1               5                   10                  15

Lys Glu Asn Leu
            20

<210> SEQ ID NO 289
<211> LENGTH: 20
<212> TYPE: PRT
<213> ORGANISM: Artificial Sequence
<220> FEATURE:
<223> OTHER INFORMATION: Synthetic peptide

<400> SEQUENCE: 289

Leu Lys Glu Asn Leu Cys Leu Asn Leu His Lys Phe Asn Glu Phe Ile
1               5                   10                  15

Gln Asn Glu Leu
            20

<210> SEQ ID NO 290
<211> LENGTH: 20
<212> TYPE: PRT
<213> ORGANISM: Artificial Sequence
<220> FEATURE:
<223> OTHER INFORMATION: Synthetic peptide

<400> SEQUENCE: 290

Ile Gln Asn Glu Leu Gln Glu Ala Ser Gln Glu Leu Gln Gln Ile His
1               5                   10                  15

Gln Tyr Ile Met
            20

<210> SEQ ID NO 291
<211> LENGTH: 20

-continued

```
<212> TYPE: PRT
<213> ORGANISM: Artificial Sequence
<220> FEATURE:
<223> OTHER INFORMATION: Synthetic peptide

<400> SEQUENCE: 291

His Gln Tyr Ile Met Ala Leu Arg Glu Glu Tyr Phe Asp Pro Ser Ile
1               5                   10                  15

Val Gly Trp Thr
            20

<210> SEQ ID NO 292
<211> LENGTH: 20
<212> TYPE: PRT
<213> ORGANISM: Artificial Sequence
<220> FEATURE:
<223> OTHER INFORMATION: Synthetic peptide

<400> SEQUENCE: 292

Ile Val Gly Trp Thr Val Lys Tyr Tyr Glu Leu Glu Glu Lys Ile Val
1               5                   10                  15

Ser Leu Ile Lys
            20

<210> SEQ ID NO 293
<211> LENGTH: 20
<212> TYPE: PRT
<213> ORGANISM: Artificial Sequence
<220> FEATURE:
<223> OTHER INFORMATION: Synthetic peptide

<400> SEQUENCE: 293

Val Ser Leu Ile Lys Asn Leu Leu Val Ala Leu Lys Asp Phe His Ser
1               5                   10                  15

Glu Tyr Ile Val
            20

<210> SEQ ID NO 294
<211> LENGTH: 20
<212> TYPE: PRT
<213> ORGANISM: Artificial Sequence
<220> FEATURE:
<223> OTHER INFORMATION: Synthetic peptide

<400> SEQUENCE: 294

Ser Glu Tyr Ile Val Ser Ala Ser Asn Phe Thr Ser Gln Leu Ser Ser
1               5                   10                  15

Gln Val Glu Gln
            20

<210> SEQ ID NO 295
<211> LENGTH: 20
<212> TYPE: PRT
<213> ORGANISM: Artificial Sequence
<220> FEATURE:
<223> OTHER INFORMATION: Synthetic peptide

<400> SEQUENCE: 295

Ser Gln Val Glu Gln Phe Leu His Arg Asn Ile Gln Glu Tyr Leu Ser
1               5                   10                  15

Ile Leu Thr Asp
            20

<210> SEQ ID NO 296
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 296

Ser Ile Leu Thr Asp Pro Asp Gly Lys Gly Lys Glu Lys Ile Ala Glu
1               5                   10                  15

Leu Ser Ala Thr
            20

<210> SEQ ID NO 297
<211> LENGTH: 20
<212> TYPE: PRT
<213> ORGANISM: Artificial Sequence
<220> FEATURE:
<223> OTHER INFORMATION: Synthetic peptide

<400> SEQUENCE: 297

Glu Leu Ser Ala Thr Ala Gln Glu Ile Ile Lys Ser Gln Ala Ile Ala
1               5                   10                  15

Thr Lys Lys Ile
            20

<210> SEQ ID NO 298
<211> LENGTH: 20
<212> TYPE: PRT
<213> ORGANISM: Artificial Sequence
<220> FEATURE:
<223> OTHER INFORMATION: Synthetic peptide

<400> SEQUENCE: 298

Thr Lys Lys Ile Ile Ser Asp Tyr His Gln Gln Phe Arg Tyr Lys Leu
1               5                   10                  15

Gln Asp Phe Ser
            20

<210> SEQ ID NO 299
<211> LENGTH: 20
<212> TYPE: PRT
<213> ORGANISM: Artificial Sequence
<220> FEATURE:
<223> OTHER INFORMATION: Synthetic peptide

<400> SEQUENCE: 299

Leu Gln Asp Phe Ser Asp Gln Leu Ser Asp Tyr Tyr Glu Lys Phe Ile
1               5                   10                  15

Ala Glu Ser Lys
            20

<210> SEQ ID NO 300
<211> LENGTH: 20
<212> TYPE: PRT
<213> ORGANISM: Artificial Sequence
<220> FEATURE:
<223> OTHER INFORMATION: Synthetic peptide

<400> SEQUENCE: 300

Ile Ala Glu Ser Lys Arg Leu Ile Asp Leu Ser Ile Gln Asn Tyr His
1               5                   10                  15

Thr Phe Leu Ile
            20
```

```
<210> SEQ ID NO 301
<211> LENGTH: 20
<212> TYPE: PRT
<213> ORGANISM: Artificial Sequence
<220> FEATURE:
<223> OTHER INFORMATION: Synthetic peptide

<400> SEQUENCE: 301

His Thr Phe Leu Ile Tyr Ile Thr Glu Leu Leu Lys Lys Leu Gln Ser
1               5                   10                  15

Thr Thr Val Met
            20

<210> SEQ ID NO 302
<211> LENGTH: 20
<212> TYPE: PRT
<213> ORGANISM: Artificial Sequence
<220> FEATURE:
<223> OTHER INFORMATION: Synthetic peptide

<400> SEQUENCE: 302

Ser Thr Thr Val Met Asn Pro Tyr Met Lys Leu Ala Pro Gly Glu Leu
1               5                   10                  15

Thr Ile Ile Leu
            20
```

IMMUNOMODULATORY METHODS AND SYSTEMS FOR TREATMENT AND/OR PREVENTION OF HYPERTENSION

CROSS REFERENCE TO RELATED APPLICATIONS

This application is the National Phase of International Application PCT/US2011/060482, filed Nov. 11, 2011, which designated the U.S. and that International Application was published under PCT Article 21(2) in English, which claims the priority benefit of the filing date of U.S. Provisional Application No. 61/413,375, filed Nov. 12, 2010, the disclosures of each of which are incorporated herein by reference in their entirety.

FIELD

The present disclosure relates to immunomodulatory methods, systems, compositions, and vaccines that are particularly suitable for the treatment or prevention of hypertension and/or of a condition associated thereto.

BACKGROUND

Hypertension and its complications affect an increasing percentage of the population.

Treatment of hypertension is typically performed through lifestyle modification and through administration of various medications. However, lifestyle modification and/or hypertension medications may not be enough to achieve satisfactory control of blood pressure. Many patients with hypertension require 2 to 3 different classes of anti-hypertensive medications enhance rendering patients less compliant to medications. Furthermore, some individuals have resistant hypertension that cannot be treated with current medications adequately.

Providing an effective treatment and/or prevention for hypertension is currently still challenging.

SUMMARY

Provided herein are methods and systems that allow in several embodiments treatment and/or prevention of hypertension in an individual, alone or in combination with other treatments, including various medications.

According to a first aspect, a method to treat and/or prevent hypertension and/or a condition associated thereto is described. The method comprises administering to an individual an immunogenic fragment of ApoB-100 or an immunogenically active portion thereof.

According to a second aspect, a method to treat and/or prevent hypertension and/or a condition associated thereto is described. The method comprises administering to an individual CD8(+) T specific for an immunogenic fragment of ApoB-100 or an immunogenically active portion thereof.

According to a third aspect, a system to treat and/or prevent hypertension and/or a condition associated thereto in an individual is described. The system comprises at least two of one or more of a CD8(+) T cell specific for an immunogenic fragment of ApoB-100 or an immunogenically active portion thereof and one or more enhancers the CD8(+) T cell. In particular, in several embodiments, the one or more of a CD8(+) T cell specific for an immunogenic fragment of ApoB-100 or an immunogenically active portion thereof and one or more enhancers of the CD8(+) T cell are included in the system for simultaneous, combined or sequential use in methods herein described.

According to a fourth aspect, a system to treat and/or prevent hypertension and/or a condition associated thereto in an individual is described. The system comprises one or more immunogenic fragments of ApoB-100 or an immunogenically active portion thereof and CD8(+) T cells, and one or more of a CD8(+) T cell specific for an immunogenic fragment of ApoB-100. In particular, in several embodiments, the one or more immunogenic fragments of ApoB-100 or an immunogenically active portion thereof and CD8(+) T cells, and one or more of a CD8(+) T cell are included in the system for simultaneous, combined or sequential use in methods herein described.

The fragments, cells, compositions, methods and systems herein described can be used in connection with applications wherein reduction hypertension and/or a therapeutic or preventive effect for hypertension in an individual are desired.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
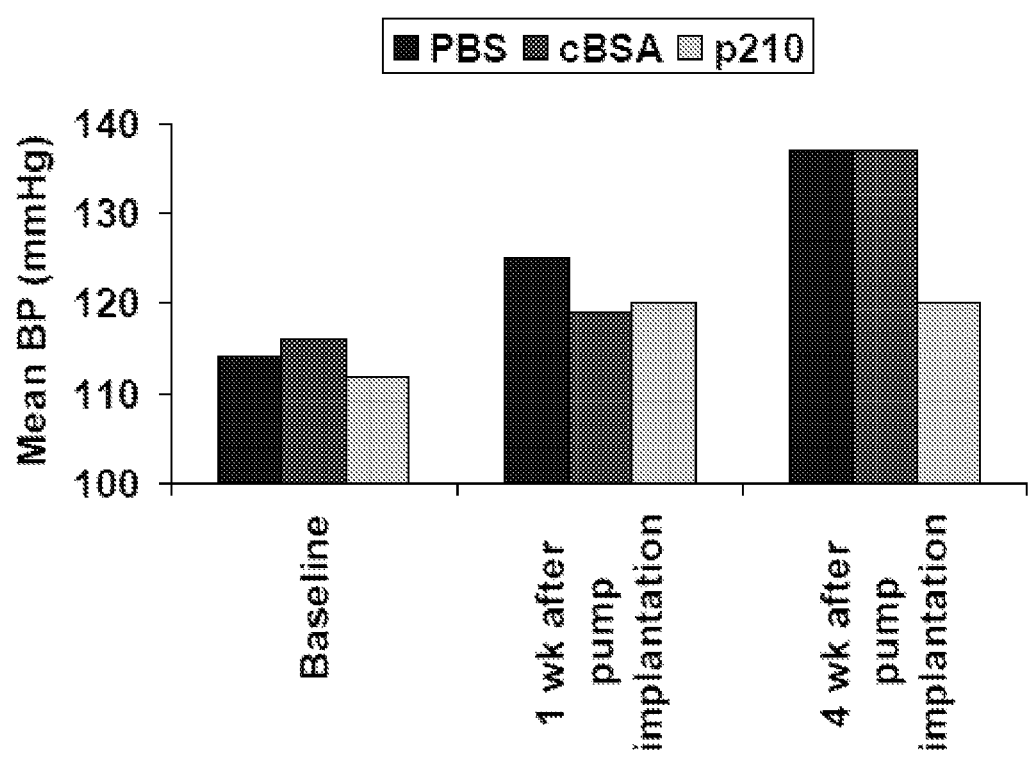
FIG. 1 shows the effect of p210 immunization on mean blood pressure in various groups of mice according to an embodiment herein described.

Methods and systems are herein described that allow in several embodiments, treatment and/or prevention of hypertension and/or of a condition associated thereto.

The term "hypertension" as used herein refers to high blood pressure. In particular, hypertension (HTN) or high blood pressure is a chronic medical condition in which the systemic arterial blood pressure is elevated. It is the opposite of hypotension. It is classified as either primary (essential) or secondary. About 90-95% of cases are termed "primary hypertension", which refers to high blood pressure for which no medical cause can be found. The remaining 5-10% of cases (Secondary hypertension) is caused by other conditions that affect the kidneys, arteries, heart, or endocrine system.

The term "treat," or "treating" or "treatment" as used herein indicates any activity that is part of a medical care for, or that deals with, a condition medically or surgically. The term "preventing" or "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates the physical status of the body of an individual (as a whole or of one or more of its parts) that does not conform to a physical status of the individual (as a whole or of one or more of its parts) that is associated with a state of complete physical, mental and possibly social well-being. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviours of the individual and atypical variations of structure and functions of the body of an individual or parts thereof.

The wording "associated to" or "associated hereto" as used herein with reference to two items indicates a relation between the two items such that the occurrence of a first item is accompanied by the occurrence of the second item, which includes but is not limited to a cause-effect relation and sign/symptoms-disease relation. Exemplary conditions associated with hypertension are high blood pressure, abnormal heart rates, aneurysms, atherosclerosis, stroke, myocardial infarction, and kidney failure. Additional, conditions associated to HTN comprise left ventricular hypertrophy, congestive heart failure associated with hypertension (e.g. left ventricular diastolic dysfunction). Many immune components have been identified that participate in conditions associated with hypertension, and suggest that immune-modulatory therapies targeting these components can reduce the likelihood of having hypertension.

In some embodiments, treatment and/or prevention of hypertension can be provided by administering to an individual an effective amount of one or more immunogenic fragments of ApoB-100 or an immunogenically active portion thereof.

The term "administer" or "administering" or "administration" as used herein means any method of providing an individual with a substance in any fashion including, but not limited to, those discussed herein.

The term "individual" or "individuals" as used herein indicates a single biological organism such as higher animals and in particular vertebrates such as mammals and more particularly human beings.

The term "immunogenic fragment" or "antigenic fragment" as used herein indicates a portion of a polypeptide of any length capable of generating an immune response, such as an antigen. An antigen is a molecule recognized by the immune system. An antigenic fragment of apoB 100 is accordingly a portion of apoB-100 that presents antigenic properties (e.g. a specific humoral or cellular response).

The term "fragment of ApoB100" in the sense of the present disclosure comprises not only fragments of any length from ApoB 100, but also peptides produced by genetic recombination or chemically synthesized comprising sequences from ApoB 100 The term "immunogenic fragments" in the sense of the present disclosure further comprise also derivative of any fragment, such as mutated fragments (including fragments with replaced, added or deleted residues) oxidative derivative and/or peptide treated with MDA or copper, which maintain a detectable antigenic property of the original fragment.

The term "derivative" as used herein with reference to a first peptide (e.g., an immunogenic fragment), indicates a second peptide that is structurally related to the first peptide and is derivable from the first peptide by a modification that introduces a feature that is not present in the first peptide while retaining functional properties of the first peptide. Accordingly, a derivative polypeptide of an immunogenic fragment, or of any portion thereof, e.g. an epitope thereof, usually differs from the original an immunogenic fragment or portion thereof by modification of the amino acidic sequence that might or might not be associated with an additional function not present in the original peptide or portion thereof. A derivative peptide of an immunogenic fragment or of any portion thereof retains however one or more of the immunogenic activities that are herein described in connection with an immunogenic fragment or portion thereof. The antigenic properties can be verified with methods and systems such as the ones already described for the immunogenic fragments and additional methods and systems identifiable to a skilled person. Typically, a derivative of an immunogenic fragment comprises at least one epitope of the immunogenic fragment.

The term "immunogenically active portion" in the sense of the present disclosure indicates any part of a reference antigen that can elicit specific immune response. Exemplary immunogenically active portions are the epitopes typically formed by 5 or more residues comprised within an immunogenic fragment. In some embodiments, epitopes within one or more fragments can overlap.

Immunogenic fragments can be expressed by recombinant technology, such as a fusion with an affinity or epitope tag, chemical synthesis of an oligopeptide, either free or conjugated to carrier proteins, or any other methods known in the art to express the ApoB-100 peptides.

Exemplary fragments of ApoB 100 are peptides each comprising one of the sequences listed in the Sequence Listing as SEQ ID NO: 1 to SEQ ID NO: 302 described in further detail in the Examples section. Methods and systems suitable to identify an immunogenic fragment in the sense of the present are described in WO 02/080954, hereby incorporated by reference. Additional methods are exemplified in the Examples section (see e.g. Example 1).

The term "protein" or "polypeptide" or "peptide" as used herein indicates an organic polymer composed of two or more amino acid monomers and/or analogs thereof. The term "polypeptide" includes amino acid polymers of any length including full length proteins or peptides, as well as analogs and fragments thereof. A peptide of three or more amino acids is also called an oligopeptide. As used herein the term "amino acid", "amino acidic monomer", or "amino acid residue" refers to any of the twenty amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

In an embodiment, the one or more immunogenic fragments of ApoB 100 suitable to treat hypertension are associated to atherosclerosis reduction.

Methods to identify a molecule associated with atherosclerosis reduction are identifiable by a skilled person and include the exemplary procedures described in WO 02/080954 herein incorporated by reference in its entirety. In particular, the ability of a molecule to reduce atherosclerosis can be tested in an animal model following administration of the molecule in a suitable amount using procedure identifiable by a skilled person. For example following subcutaneous administration of a molecule herein described the ability of the molecule to affect atherosclerosis can be tested in mice as illustrated in the Examples sections. A skilled person will be able to identify additional procedure, schedule of administration and dosages upon reading of the present disclosure.

Accordingly in an exemplary embodiment, immunogenic molecule associated with atherosclerosis reduction can be identified by identifying a candidate immunogenic molecule able to provide a cellular and/or humoral response in the individual of interest; and testing the candidate immunogenic molecule for an ability to reduce atherosclerosis, to select the candidate immunogenic molecule associated with atherosclerosis reduction.

In particular, in some embodiments, immunogenic fragments of ApoB 100 are immunogenic fragments producing an immune response associated to atherosclerosis reduction in the individual or in an animal model. In some of those embodiments, a percentage atherosclerosis reduction is at least about 20%, or at least about 30%, from about 40% to about 60% or about 50% to about 80%.

Reference is made to Examples section wherein embodiments of the present disclosure are exemplified with reference to immunogenic fragment p210 associated with a reduction of hypertension of about 11% (see Example 2). Additional fragments associated to atherosclerosis reduction are particularly expected to be effective in treatment and/or prevention of hypertension (see Examples section).

In some embodiments, the immunogenic fragment associated to atherosclerosis reduction and suitable to be used to treat and/or prevent hypertension comprises at least one of peptide, each comprising p1 (SEQ ID NO: 1), p2 (SEQ ID NO: 2), p11 (SEQ ID NO:11), p25 (SEQ ID NO:25), p45 (SEQ ID NO:45), p74 (SEQ ID NO:74), p99 (SEQ ID NO:99), p100 (SEQ ID NO:100), p102 (SEQ ID NO:102), p103 (SEQ ID NO: 103), p105 (SEQ ID NO:105), p129 (SEQ ID NO:129), p143 (SEQ ID NO:143), p148 (SEQ ID NO:148), p210 (SEQ ID NO:210), or p301 (SEQ ID NO:301).

In an embodiment, the one or more immunogenic fragments associated to atherosclerosis reduction and suitable to be used to treat and/or prevent hypertension comprises one or more peptides each comprising p2 (SEQ ID NO:2), p11 (SEQ ID NO:11), p45 (SEQ ID NO: 45), p74 (SEQ ID NO: 74), p102 (SEQ ID NO: 102), p148 (SEQ ID NO:148), or p210 (SEQ ID NO:210).

In an embodiment, the one or more immunogenic fragments associated to atherosclerosis reduction and suitable to be used to treat and/or prevent hypertension comprises two peptides each comprising p143 (SEQ ID NO: 143), or p210 (SEQ ID NO:210). In an embodiment, the one or more immunogenic fragments associated to atherosclerosis reduction comprises three peptides each comprising, one of p11 (SEQ ID NO:11), p25 (SEQ ID NO: 25), or p74 (SEQ ID NO:74). In an embodiment, the one or more immunogenic fragments associated to atherosclerosis reduction comprises five peptides each comprising one of p99 (SEQ ID NO: 99), p100 (SEQ ID NO: 100), p102 (SEQ ID NO: 102), p103 (SEQ ID NO: 103), and p105 (SEQ ID NO: 105).

In an embodiment, the one or more immunogenic fragments associated to atherosclerosis reduction and suitable to be used to treat and/or prevent hypertension comprises one or more peptides each comprising p2 (SEQ ID NO: 2), p45 (SEQ ID NO: 45), p74 (SEQ ID NO: 74), p102 (SEQ ID NO: 102), or p210 (SEQ ID NO:210).

In an embodiment, the one or more immunogenic fragments associated to atherosclerosis reduction and suitable to be used to treat and/or prevent hypertension comprise a peptide comprising amino acids 16-35 of human apoB-100 (p2; SEQ ID NO:2).

In an embodiment the one or more immunogenic fragments associated to atherosclerosis reduction and suitable to be used to treat and/or prevent hypertension comprise a peptide comprising amino acids 661-680 of human apoB-100 (p45; SEQ ID NO:45).

In an embodiment, the one or more immunogenic fragments associated to atherosclerosis reduction and suitable to be used to treat and/or prevent hypertension comprise a peptide comprising amino acids 3136-3155 of human apoB-100 (P210; SEQ ID NO: 210).

In an embodiment, the one or more immunogenic fragments associated to atherosclerosis reduction and suitable to be used to treat and/or prevent hypertension comprise a peptide comprising amino acids 4502-4521 of human apoB-100 (P301; SEQ ID NO: 301).

In an embodiment, the one or more immunogenic fragments associated to atherosclerosis reduction and suitable to be used to treat and/or prevent hypertension comprise a peptide comprising amino acids 1-20 of human apoB-100 (P1; SEQ ID NO: 1).

Exemplary data showing association of the above peptides to atherosclerosis reduction are shown in Example 3 of the present disclosure and in International application WO 02/080954, herein incorporated by reference in its entirety (see in particular Table 1, Table 2, Table A and Table B). In particular for some of those peptides or combination thereof a percentage reduction of 64.6% (p143 and p210), 59.6% (p11, p25 and p74), 56.8% (p129, p148, and p167), 67.7 (p2), 57.9% (p210), 55.2% (p301), 47.4% (p45), 31% (p1) has been detected (see WO/02080954 incorporated herein by reference in its entirety, and in particular Table B)

Immunogenic peptides comprising any of the sequences herein described or immunogenically active portions of those peptides are identifiable by a skilled person using in silico and/or in vitro approaches. For example, in silico methods can be used to identify any of said epitopes or immunogenic peptides based on any of the sequences herein described. Reference is made for example, to the papers [44] to [51] each of which is incorporated herein by reference in its entirety.

Such papers describe various algorithms such as Tepitope (Radrizzani et al 2000), Adept (Maksuytov et al 1993), antigenic index (Jameson et al 1988) and others which can be used to identify the immunogenic molecules comprising the sequences at issue or any relevant epitopes.

Additional tests and laboratory procedures in vitro and/or in vivo suitable to be used alone or in connection with the identification in silico (e.g. ELISA) are identifiable by a skilled person that can be used by a skilled person to verify the in silico data and/or identify immunologically active molecules comprising any of the sequences herein described or immunologically active portions of those sequences.

Accordingly, in an exemplary embodiments, immunogenic peptides, herein described, immunogenically active portions thereof as well as derivative thereof can be identified by identifying candidate peptides, candidate active portion and/or candidate derivative by in silico analysis of any one of the sequences herein described, and by identifying the immunogenic peptides, immunogenically active portions and/or derivative by in vitro and/or in vivo testing of the candidate peptides, candidate active portion and/or candidate derivative. In particular, the in silico analysis can be performed by analyzing the sequence of the candidate with algorithm suitable to identify immunogenicity of a molecule or portion thereof. Similarly, the in vitro and/or in vivo testing comprises methods directed to identify immunogenicity of the candidate peptide, candidate active portion and/or derivative as well as effects of those molecules on aneurysm, with particular reference to formation or regression. Suitable methods and techniques are identifiable by a skilled person upon reading of the present disclosure.

In several embodiments, the immunogenic peptides, active portions thereof and derivative thereof are expected to include a sequence of at least about 5 amino acids, consistently with the typical length of epitopes as indicated in WO 02/080954 herein incorporated by reference in its entirety.

In an embodiment, immunization with one or more of the immunogenic molecules herein described reduces the incidence of blood pressure (e.g. Example 2).

The expected reduction of blood pressure after immunization is at least about 10%, when compared to a control measurement and in particular from about 10% to an amount determined by a physician based on the condition and the individual to be immunized.

The term "effective amount" as used herein is meant to describe that amount of antigen, e.g. P210, which induces an antigen-specific immune response.

Effective amounts of an immunogenic fragment and of one or more of the immunogenic molecules herein described to treat and/or prevent hypertension will depend on the individual wherein the activation is performed and will be identifiable by a skilled person. For example in an embodiment the T cell activation can be performed with an effective amount of from about 100 μg to less than about 1000 μg immunogenic fragment or immunogenically active portion thereof. In an embodiment, treatment and/or prevention hypertension can be performed with an effective amount of from about 1 to about 100 mg immunogenic fragment or immunogenically active portion thereof. Additional effective amounts are identifiable by a skilled person in view of the individual where activation is performed and the desired activation.

In an embodiment, an effective amount for the treatment or prevention can be about 100 µg or more. In some embodiments, treatment and/or prevention can be performed with an amount that is 1 mg or more, e.g. up to 100 mg.

A greater concentration can be used in some embodiments depending on the desired effect as illustrated in the present disclosure. For example, in embodiments wherein treatment of severe hypertension is desired, treatment is expected to be performed with an effective amount be 250 µg or more and in particular with about 500 µg. In another example, wherein the hypertension is less severe an effective amount to treat hypertension is expected to be at a lower amount compared to an amount used for treatment (e.g. from 100 to 250 µg) even if in some cases, an amount falling within the range of 250 µg or 500 µg or higher is also expected to be effective also depending on other factors affecting the pharmacological activity of the molecule in an individual.

In particular the effective amount is also expected to vary depending on the number and combination of peptides utilized for each particular vaccine, and specific characteristic and conditions of the individual treated (e.g. immune system diet and general health and additional factors identifiable by a skilled person). More particular, lower or higher amounts within the defined range are expected to be effective in an individual depending on factors such as weight, age, gender of the individual as well as additional factors identifiable by a skilled person.

In some embodiments, the immunogenic peptides herein described or related immunogenically active portions can be administered in combination with an adjuvant or other carrier suitable to affect and in particular increase immunogenicity of the peptide o active portion thereof. In particular, in some embodiments, the immunogenic peptide or active portion thereof can be conjugated to the adjuvant or carrier according to procedures identifiable to a skilled person. Suitable carriers comprise BSA, and in particular, cationized BSA, aluminum salts such as aluminum phosphate and aluminum hydroxide and additional carriers identifiable by a skilled person.

In some embodiments, immunogenic molecules herein described can be administered in ratios of immunogenic molecule to carrier to aluminum of about: 1:2:35, 1:2:20.6, 1:2:7.7, 1:2:3.3, 1:1:13.8 weight to weight ratios. In particular, in some embodiments, ratios can be provided wherein the number of peptides conjugated to each carrier molecule while minimizing the amount of aluminum (adjuvant). In particular in one embodiment, ratio can be provided that result in a concentration up to 2.7 mg conjugate/mL.

In an embodiment, the administering is performed according to a schedule of administration to be determined in view of the desired effect. In particular, administration is expected to be performed in accordance with dosages and schedule which will be identified based on the condition of the individual to be treated and the desired effect. For example, administration can be performed by performing either a single administration, or a plurality of administrations (e.g. 3 administrations or more, in particular up to 6 administrations) of immunogenic fragments or immunogenically active portion thereof herein described in intervals to obtain a desired immunization based on the condition of the individual.

In some embodiments the immunogenic molecules herein described can be administered according to a schedule of administration devised in view of the amount of time required by the adaptive immune system of an individual to mount a response to the initial exposure to an immunogen. Typically, the response is expected to plateau at 2-3 weeks after exposure. Subsequent exposures often elicit a more rapid response. In various embodiments, the following schedules and manner of administration can be followed: (1) single administration, (2) two administrations 2-3 weeks apart, (3) three weekly administrations, (4) up to 6 administrations on a 1 every 3 week schedule. The vaccines have been administered by: (1) subcutaneous injection; (2) intraperitoneal injection; (3) nasal installation; (4) subcutaneous infusion.

The route of immunization can vary depending on the purposes of immunization described herein. Successful prevention and treatment of hypertension in mice occurred by subcutaneous osmotic pump injections (see Example 2). The type of immune response triggered is largely determined by the route of immunization. Various routes can be used comprising subcutaneous, parenteral, and systemic among the others. In particular, the mucosal linings of airways and intestines contain lymphatic tissue that, when exposed to antigen, elicits anti-inflammatory, immunosuppressive responses. Distinct immunological features of the respiratory and intestinal mucosa lead to partly different types of protective immunity upon antigen exposure by the nasal or oral route.

In an embodiment, administering one or more immunogenic fragment or an immunogenically active portion thereof can be performed intramuscularly, or mucosally (e.g. nasally, orally, and/or vaginally).

In some embodiments, methods are provided to prevent hypertension and/or a condition associated thereto in an individual, the method comprising administering to the individual an effective amount of CD8(+) T cells specific for an immunogenic fragment of ApoB-100.

In some embodiments, methods are provided to prevent hypertension and/or a condition associated thereto in an individual, the method comprising increasing in the individual an activated CD8(+) T cell specific for an immunogenic fragment of ApoB-100 or an immunogenically active portion thereof.

The term "T cells" as used herein indicates T lymphocytes belonging to a group of white blood cells known as lymphocytes, and participate in humoral or cell-mediated immunity. T cells can be distinguished from other lymphocyte types, such as B cells and natural killer cells (NK cells) by the presence of special markers on their cell surface such as T cell receptors (TCR). Additional markers identifying T cell include CD1a, CD3, CD4, CD8 and additional markers possibly associated to a T cell state and/or functionality as will be understood by a skilled person.

The term "CD8(+) T cells" indicates T cells expressing the CD8 glycoprotein at their surface, wherein the CD8 (cluster of differentiation 8) glycoprotein is a transmembrane glycoprotein that serves as a co-receptor for the T cell receptor (TCR). Similarly to the TCR, CD8 binds to a major histocompatibility complex (MHC) molecule, but is specific for the class I MHC protein. Exemplary CD8 T cells comprise cytotoxic memory CD8 T cells, regulatory CD8 T cells, cytotoxic effector CD8 T-cells and additional cells identifiable by a skilled person. There are two isoforms of the protein, alpha and beta, each encoded by a different gene. In humans, both genes are located on chromosome 2 in position 2p12.

The term "activated" and activation as used herein indicate the process by which a T cells interacts with an antigen presenting cell which presents a specific antigen for a time and under condition resulting in a T cell having a preassigned immunological role (e.g. cytotoxicity) within the immune system. The term "antigen-presenting cell" (APC) indicates a cell that displays antigen complex with major histocompatibility complex (MHC) on its surface. T-cells recognize this complex using their T-cell receptor (TCR). Exemplary APCs comprise dendritic cells (DCs) which are known to play an important role in linking innate and acquired immunity (3)(4) and both immune responses participate in atherogenesis (5), (6).

Detection of T cells and in particular, CD8(+) T cells, can be performed by detection of markers such as CD8, alone or in combination with TCRCD3 and additional markers identifiable by a skilled person. Detection of activated CD8(+) T cells can be performed by detection of T cells markers and in particular of markers such as CD25, CD44, CD62, and additional markers identifiable by a skilled person using process and techniques suitable for detecting surface markers.

The terms "detect" or "detection" as used herein indicates the determination of the existence, presence or fact of a molecule or cell in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

Exemplary techniques suitable for detecting T cell markers comprise use of suitable monoclonal or polyclonal antibodies or antigen-specific HLA or MHC pentamers or hexamers labeled with an appropriate molecule allowing detection as well as additional methods and techniques identifiable by a skilled person. In an exemplary approach T cell markers are identified by flow cytometric analysis as described in the Examples section. Exemplary techniques suitable for detecting T cell markers comprise use of suitable monoclonal or polyclonal antibodies or antigen-specific HLA or MHC pentamers or hexamers labeled with an appropriate molecule allowing detection as well as additional methods and techniques identifiable by a skilled person. In an exemplary approach T cell markers are identified by flow cytometric analysis as described in the Examples section. In some embodiments of the T cell, compositions methods and systems herein described CD8(+) T cells can be activated using one or more immunogenic fragments of ApoB 100 or an immunogenically active portion thereof.

In particular, activated CD8(+) T cells specific for an immunogenic fragment of ApoB100 are obtainable by contacting a CD8(+) T cells with one or more peptides selected from the group consisting of p1 (SEQ ID NO: 1), p2 (SEQ ID NO: 2), p11 (SEQ ID NO:11), p25 (SEQ ID NO:25), p45 (SEQ ID NO:45), p74 (SEQ ID NO:74), p99 (SEQ ID NO:99), p100 (SEQ ID NO:100), p102 (SEQ ID NO:102), p103 (SEQ ID NO: 103), p105 (SEQ ID NO:105), p129 (SEQ ID NO:129), p143 (SEQ ID NO:143), p148 (SEQ ID NO:148), p210 (SEQ ID NO:210), or p301 (SEQ ID NO:301) or an immunogenically active portion thereof for a time and under condition to activate the CD8(+) T cell, the activated CD8(+) T cell specific for the one or more peptides or the immunogenically active portion thereof.

Activated CD8(+) T cells according to the present disclosure are activated with one or more immunogenic fragment of ApoB 100 or an immunogenically active portion thereof and are typically specific for the immunogenic fragment or the immunogenically active portion used for the activation.

The wording "specific" "specifically" or "specificity" as used herein with reference to the immunogenic response refers to the ability of an immunological agent to direct the immunological activity towards an antigen, together with substantially less to no immunological activity towards other antigen that may be present. As consequence, CD8 (+) T cells herein are specifically activated towards the immunogenic fragment or active portion used to activate them and not for other antigens.

Exemplary antigenic properties that can be used to identify CD8 T cell specific for the immunogenic fragments comprise humoral and/or cellular responses detectable using methods and techniques such as the ones exemplified in the Examples section as well as other methods and techniques identifiable by a skilled person. Exemplary methods and systems for detecting antigenic properties in the sense of the present disclosure comprise ELISA and in particular serum ELISA and additional methods exemplified in the Examples section. Exemplary techniques suitable for detecting T cell markers comprise use of suitable monoclonal or polyclonal antibodies or antigen-specific HLA or MHC pentamers or hexamers labeled with an appropriate molecule allowing detection as well as additional methods and techniques identifiable by a skilled person. In an exemplary approach T cell markers are identified by flow cytometric analysis as described in the Examples section.

In an embodiment, activated the CD8(+) T cells are specific for one or more of any of the peptides between SEQ ID NO:1 and SEQ ID NO:302 or an immunogenically active portion thereof that are associated with treatment or prevention of atherosclerosis. In some embodiments the immunogenic fragment comprises one or more of the peptides SEQ ID NO:2, SEQ ID NO:11, SEQ ID NO: 45, SEQ ID NO: 74, SEQ ID NO: 102, SEQ ID NO:148, SEQ ID NO:210 or an immunogenically active portion thereof. In some embodiments the immunogenic fragment comprises one or more of the peptides SEQ ID NO:2, SEQ ID NO: 45, SEQ ID NO: 74, SEQ ID NO: 102, SEQ ID NO:210 or an immunogenically active portion thereof. Even more particularly, in some embodiments the immunogenic fragment comprises amino acids 3136-3155 of human apoB-100 (P210; SEQ ID NO: 210) or an immunogenically active portion thereof. In general, the same combination of immunogenic fragments proven or expected to be associated with treatment and/or prevention of hypertension in an individual are also expected to be able to activate CD8(+)T cells to be used in treatment and/or prevention of hypertension in the individual. In particular, T cell activation can be performed using any of the molecules herein described administered in vivo in an amount suitable to treat or prevent aneurysms, (see e.g. Example section). Activation of T cell can also be performed in vitro using methods and procedures such as the ones described in ref [52] as well as additional procedures identifiable by a skilled person.

In an embodiment, an increasing of CD8(+)T cell to treat and/or prevent hypertension in the individual can be performed by administering to the individual an effective amount of an activated CD8(+) T cell.

In an embodiment the effective amount is expected to be comprised between about 500,000 to about 2,000,000 cells. In embodiment the effective amount is expected to be comprised between about 750,000 to about 1,500,000 cells. In an embodiment, the effective amount is expected to be about 1,000,000 cells.

In particular, in an embodiment administration of about 1,000,000 cells is expected to result in both treatment and prevention of atherosclerosis and is therefore expected to also be effective in treatment and prevention of hypertension. Administration is expected to be performed in accordance with dosages and schedule which will be identified based on the condition of the individual to be treated and the desired effect. For example in administration directed to prevention, administering an effective amount of activated CD8(+) T cell can performed by performing either a single administration, or a plurality of administrations (e.g. 3 administrations or more, in particular up to 6 administrations) of activated CD8 (+) T cell herein described in intervals to obtain a desired immunization based on the condition of the individual. In particular, a plurality of administrations can be performed whenever a prolonged immunizing effect is desired.

In some embodiments, activated CD8+ T cells herein described are expected to be effective according to a schedule of administration wherein those cells are administered daily (for up to 21 days) and on an every 10 day schedule (days 0, 10, 20). Additional schedules expected to be effective can be identified by a skilled person based on cell treatments of other condition such as HIV and/or cancer.

Administration of CD8(+) T cell herein described can be performed according to methods to immunize an individual identifiable to a skilled person. In an embodiment, the administering can be performed by parenteral administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion. In particular, in an embodiment the administering can be performed by intravenous administration.

In an embodiment, administration can be performed by administering activated CD8(+) T cell one time, typically via intravenous route, one time or multiple times, depending on the desired duration of the immunization effect.

In some embodiments wherein methods are provided to treat and/or prevent hypertension and/or a condition associated thereto in an individual an effective amount of CD8(+) T cells specific for an immunogenic fragment of ApoB 100 can be administered alone or in combination with an effective amount of one or more immunogenic fragments herein described or immunogenically active portion thereof. In particular, the one or more immunogenic fragments or immunogenically active portion thereof can be administered with CD8(+)T cells in the same or less the concentration required as an effective amount of immunogenic fragment used to treat and/or prevent hypertension.

In some embodiments wherein methods are provided to treat and/or prevent hypertension and/or a condition associated thereto in an individual, the effective amount of activated CD8(+) T cells and/or immunogenic fragment of ApoB 100 or immunogenically active portion thereof vary, and so is the route of immunization which can vary depending on the purposes of immunization described herein. Various routes can be used comprising subcutaneous, parenteral, and systemic among the others. In particular, the mucosal linings of airways and intestines contain lymphatic tissue that, when exposed to cells, elicits anti-inflammatory, immunosuppressive responses.

In some embodiments, administering of an immunogenic fragment and/or a CD8(+) T cell can be performed in combination with an enhancer of CD8(+) T cell activation.

The terms "enhancer" and "enhance" as it pertains to a molecule in connection with CD8 T cell refers to the ability of a molecule to modify the immune response by promoting the activation of cells of the immune system. The choice of appropriate enhancer can allow control of activation of the immune response. Exemplary enhancers include cytokines such as IL 10, IL-2, IL 12, IL-4 IL-16. The term "cytokine" as used herein refers cell signaling molecules that act as has immunomodulating agents, and comprise proteins such as interleukins and interferons as would be identifiable to a skilled person. Selection of a suitable cytokine can result under appropriate conditions in the preferential induction of a humoral or cellular immune response.

In an embodiment, the enhancer can be Interleukin 2 (IL2), interleukin 10 (IL10), Interleukin 15 (IL-15), TGF-beta (TGF-β), IL2-antiIL-2 antibody complex and/or additional enhancer identifiable by a skilled person upon reading of the present disclosure. Reference is made to the references Mitchell et al 2010 (38), Perret et al 2008 (39) and Kamimura et al 2007 (40), each incorporated by reference in their entirety, which describe exemplary use of enhancer in connection with T cell activation.

In particular in some embodiments, the enhancing is performed by reducing CD86 expression and/or IL12 secretion by dendritic cells in the individual.

In some embodiments, an immunogenic fragment of ApoB-100 is further administered with the methods that are provided to treat and/or prevent hypertension and/or a condition associated thereto in an individual together with an effective amount of CD8(+) T cells specific for an immunogenic fragment of ApoB 100 and possibly an enhancer.

As disclosed herein, the immunogenic fragments or immunogenically active portion thereof, CD8 (+) Tcell, and enhancers herein described can be provided as a part of systems to treat and/or prevent hypertension or of a condition associated thereto.

In an embodiment, the system comprises at least two of one or more of an activates CD8(+) T cell and one or more cytokine able to enhance the activated CD8(+) T cell.

In an embodiment, the system comprises at least two of one or more immunogenic fragments of ApoB-100 or immunogenically active portion thereof and one or more of an activated CD8(+) T cell specific for an immunogenic fragment of ApoB-100.

In an embodiment, the system comprises at least two of one or more immunogenic fragments of apoB-100 or immunogenically active portion thereof an activated CD8(+) T cell herein described and further comprising one or more enhancers of the CD8(+) T cell.

The systems can be provided in the form of kits of parts. In a kit of parts, the immunogenic fragments, CD8(+) T cell herein described and other reagents to perform the method herein described can be comprised in the kit independently. The CD8(+) T cell herein described can be included in one or more compositions, and each CD8(+) T cell herein described can be in a composition together with a suitable vehicle.

Additional components can include enhancers molecules able to detect CD8(+) Tcell herein described, such as labeled molecules and in particular, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of a CD8(+) Tcell or immunogenic fragments herein described can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

In some embodiments, the immunogenic fragments, active portions thereof, CD8(+) Tcell and/or enhancers herein described can be included in compositions together with a suitable vehicle.

The term "vehicle" as used herein indicates any of various media acting usually as solvents, carriers, binders or diluents for T cell comprised in the composition as an active ingredient.

In some embodiments, where the composition is to be administered to an individual the composition can be a pharmaceutical anti-inflammatory composition, and comprises T cell and a pharmaceutically acceptable vehicle In particular, in some embodiments, disclosed are pharmaceutical compositions which contain at least one the immunogenic fragments, active portions thereof, CD8(+) Tcell and/or enhancers herein described as herein described, in combination with one or more compatible and pharmaceutically acceptable vehicles, and in particular with pharmaceutically acceptable diluents or excipients. In those pharmaceutical compositions the immunogenic fragments, active portions thereof, CD8(+) Tcell and/or enhancers herein described can be administered as an active ingredient for treatment or prevention of a condition in an individual.

The term "excipient" as used herein indicates an inactive substance used as a carrier for the active ingredients of a medication. Suitable excipients for the pharmaceutical compositions herein disclosed include any substance that enhances the ability of the body of an individual to absorb a immunogenic fragments, active portions thereof, CD8(+) Tcell and/or enhancers herein described. Suitable excipients also include any substance that can be used to bulk up formulations with the immunogenic fragments, active portions thereof, CD8(+) Tcell and/or enhancers herein described to allow for convenient and accurate dosage. In addition to their use in the single-dosage quantity, excipients can be used in the manufacturing process to aid in the handling of the immunogenic fragments, active portions thereof, CD8(+) Tcell and/or enhancers herein described. Depending on the route of administration, and form of medication, different excipients can be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In an embodiment, compositions herein described can further include an adjuvant. The term "adjuvant" as used herein indicates an agent that can stimulate the immune system and increase the response to a vaccine, without having any specific antigenic effect in itself. The word "adjuvant" comes from the Latin word adjuvare, meaning to help or aid. Typically, an immunologic adjuvant is defined as any substance that acts to accelerate, prolong, or enhance antigen-specific immune responses when used in combination with specific vaccine antigens.

In some embodiments, pharmaceutical composition can include (1) a peptide or other immunogenic molecule herein described administered alone, (2) a peptide or other immunogenic molecule herein described+carrier(s); (3) a peptide or other immunogenic molecule herein described+adjuvant; (4) a peptide or other immunogenic molecule herein described+carrier+adjuvant. In particular, the carriers for each of the exemplary composition (1) to (4) can comprise: (1) cBSA, (2) rHSA, (3) KLH, (4) cholera toxin subunit B, respectively, each of which can be mineral salt-based. Other carriers, known to those skilled in the art, are expected to be suitable as well as will be identified by a skilled person. Examples of those adjuvants comprise adjuvants having Th2 effects, carriers having adjuvant properties, e.g., diphtheria toxoid, and adjuvants able to function as carriers, e.g., oil-water emulsions. In some embodiments, a necessary, and under certain conditions sufficient, component for the pharmaceutical composition is the immunogenic peptides. Additional components of the composition can be selected to modulate the immunological impact of the peptides or other immunogenic molecule herein described as will be understood by a skilled person.

Further advantages and characteristics of the present disclosure will become more apparent hereinafter from the following detailed disclosure by way of illustration only with reference to an experimental section.

EXAMPLES

The methods system herein described are further illustrated in the following examples, which are provided by way of illustration and are not intended to be limiting. A person skilled in the art will appreciate the applicability of the features described in detail.

In particular, the following examples illustrate exemplary immunogenic fragments, and methods for immunizing individuals to treat or prevent hypertension and in particular methods using fragment p210.

A person skilled in the art will appreciate the applicability and the necessary modifications to adapt the features described in detail in the present section, to additional immunogenic fragments, administered subcutaneously or using other routes of administration in vivo or in vitro according to embodiments of the present disclosure.

Unless otherwise indicated the following material and methods were followed in the Examples reported below.

Selection of peptides and their preparation for immunization The establishment and screening of human apoB-100 peptides has been reported (8). Based on Applicants pilot experiments and prior reports, (9),(10) Applicants selected peptide 210 (p210, KTTKQ SFDLS VKAQY KKNKH—SEQ ID NO: 210) as a candidate immunogen. Native p210 peptide (Euro-Diagnostica AB, Sweden) was conjugated to cationic bovine serum albumin (cBSA) as carrier using a method described previously. (3),(4) Alum was used as adjuvant and mixed with peptide/cBSA conjugate with 1:1 ratio in volume. Peptide conjugation and mixing with alum were prepared fresh prior to each immunization.

Immunization protocols Male apoE (−/−) mice (Jackson Laboratories) were housed in an animal facility accredited by the American Association of Accreditation of Laboratory Animal Care and kept on a 12-hour day/night cycle with unrestricted access to water and food. The Institutional Animal Care and Use Committee of Cedars-Sinai Medical Center approved the experimental protocols. In a pilot experiment, p210 immunization using 100 µg dose conferred optimum athero-reduction compared to 25 or 50 µg dose. Hence 100 µg dose was used for all subsequent experiments. Mice, maintained on normal chow diet, received subcutaneous primary immunization in the dorsal area between scapulas at 6-7 weeks of age, followed by a booster at 9 and 12 weeks of age. One week after last booster, diet was switched to high cholesterol chow (TD 88137, Harlan-Teklad) and continued until euthanasia at the age of 25 weeks. Separate groups of mice receiving PBS or cBSA/alum at the same immunization timepoints served as control. Some mice were sacrificed at 8 or 13 weeks of age to assess immune response against p210.

Tissue harvesting and preparation At euthanasia the hearts were harvested and embedded in OCT compound (Tissue-Tek) for cryo-section. Whole aortas were cleaned, processed and stained with Oil Red O to assess the extent of atherosclerosis en face with computer-assisted histomorphometry. (3), (4).

Immunohistochemistry and histomorphometry The sections from aortic sinus were stained with MOMA-2 (Serotec), or CD11c (eBioscience) antibody to identify macrophages or dendritic cells immunohistochemically using standard protocol. Oil-Red-O stain for plaque size was done using standard protocol. Computer-assisted morphometric analysis was performed to assess histomorphometry as described previously. (3),(4)

Serum ELISA Flat-bottomed 96-well polystyrene plates (MaxiSorp, Germany) were pre-coated with 100 ul (20 µg/ml) p210, KLH, TNP-KLH (Biosearch Technologies T-5060) or BSA (2 µg/ml for IgG or 10 µg/ml for IgM) respectively by incubation overnight at 4° C. to assess antibodies levels using standard protocol. The coating concentration was optimized in pilot experiments. Goat anti-mouse HRP-IgG (Pierce 31437) or IgM (Southern Biotech) were used as detecting antibodies and the bound antibodies were detected by developing in ABTS (Southern Biotech) as substrate and optical density values were recorded at 405 nm.

Flow cytometric analysis Flow cytometric analysis was performed using standard protocols with antibodies listed in Table 1 below and a FACScan (Becton Dickinson) or a CyAn ADP analyzer (Beckman Coulter). For intracellular cytokine staining, Brefeldin A (3 µg/ml) was added to the cultured cells for 2 hours before cells subject to staining procedure. Cell membranes were permeabilized for staining intracellular molecules.

TABLE 1

| Antigen | Clone | Type | Supplier |
|---|---|---|---|
| CD4 | GK1.5 | FITC-Rat IgG2b, κ | BD Pharmingen |
| CD8b.2 | 53-5.8 | FITC-Rat IgG1, κ | BD Pharmingen |
| CD25 | PC61.5 | PE-Rat IgG1, λ | eBioscience |
| IL-10 | JES5-16E3 | Percp-Cy5.5-Rat IgG2a, κ | eBioscience |
| IL-12 | Clone C17.8 | Percp-Cy5.5-Rat IgG2b, κ | eBioscience |
| CD11c | HL3 | FITC-Hamster IgG1, λ | BD Pharmingen |
| CD86 | GL1 | PE-Rat IgG2a, κ | BD Pharmingen |
| TGF-Beta | 1D11 | APC-Mouse IgG1 | R&D system |
| Granzyme B | 16G6 | Alexa-Fluo 647 Rat IgG2b, κ | eBioscience |
| Perforin | eBioOMAK-D | FITC-Rat IgG2a, κ | eBioscience |

Adoptive transfer experiment Male apoE (−/−) mice on regular chow received subcutaneous immunization as described in previous paragraph and were sacrificed at 13 weeks of age as donors. Splenocytes from the same treatment group were pooled before cell isolation. Donor CD8(+) T-cells, CD4(+)CD25(+) T-cells or B-cells were isolated using Dynabeads FlowComp (Invitrogen) according to the manufacturer's protocols. CD4(+) T-cells were negatively selected from the splenocytes followed by positive selection of CD4(+)CD25(+) cells. B cells were negatively isolated whereas CD8(+) T-cells were positively isolated first and released from beads. The purity of pooled CD8(+) T-cells, CD4(+)CD25(+) T-cells and B-cells was 90%, 80% and 70%, respectively. The isolated CD8(+) T-cells ($1 \times 10^6$ cells/mouse), CD4(+)CD25(+) T-cells ($1 \times 10^5$ or $3 \times 10^5$ cells/mouse) or B-cells ($2 \times 10^7$ cells/mouse) were then adoptively transferred to naïve male apoE (−/−) recipient mice at 6-7 weeks of age via tail vein injection. In the published literatures of vascular biology, the number of adoptively transferred lymphocytes varied greatly. For B-cells transfer, the number of $2 \times 10^7$ cells/mouse was chosen based on two prior reports. (11),(12) For CD4(+)CD25(+) T-cells transfer, the number of cells transferred ranged from $5 \times 10^4$ cells/mouse to $1 \times 10^6$ cells/mouse in the published literature. (13),(14),(15) Hence we chose 2 intermediate doses for our experiment. As to CD8(+) T-cells, $1 \times 10^6$ cells was chosen based on a report from the field of autoimmune disease. (16) We did not adoptively transferred CD4(+) T-cells because naïve or antigen-primed CD4(+) T-cells are known to be pro-atherogenic. (17), (18) Recipient mice were fed normal chow until 13 weeks of age when chow was switched to high cholesterol diet until euthanasia at 25 weeks of age. Aortas were harvested to assess the extent of atherosclerosis.

KLH or Trinitrophenyl-lipopolysaccharide (TNP-LPS) Immunization Applicants also tested if p210 immunization affected the efficacy of subsequent immunization with other antigens. KLH was chosen as a prototypical T-cell dependent and TNP as a T-cell independent antigen. Male C57/BL6 mice on regular chow received subcutaneous immunization with p210 conjugate or adjuvant control as described in previous paragraphs for apoE (−/−) mice. At 13 and 15 weeks of age mice were subcutaneously immunized with 100 µg KLH (with alum as adjuvant) at injection sites away from p210 sites or injected intraperitoneally with 100 µg TNP-LPS (Sigma). KLH or TNP immunization was done in separate groups of mice. Blood was collected via retro-orbital puncture at euthanasia (16 weeks of age).

In Vitro Generation of BM-Derived dendritic cells (BM-DCs) The method for generating BMDC with GM-CSF was adapted from previous publication with modification. (19) Briefly, bone marrow cells from femurs and tibiae of male apoE−/− mice were plated into 10 cm culture plates (Falcon) with 20 ml complete RPMI-1640 containing 10 ng/ml GM-CSF (R&D Systems) and 10 ng/ml IL-4 (Invitrogen). Cells were washed and fed on day 3 and day 5 by removing the old medium followed by replenishing with fresh culture medium with GM-CSF and IL-4. On day 8, the immature DC appeared as non-adherent cells under the microscope and harvested by vigorous pipetting and subcultured into new culture plates with 2×10⁵ DCs in 1.5 ml medium.

In vitro CD8(+) T-cerlls isolation and co-culture with dendritic cells Donor mice [male apoE (−/−) mice] for CD8(+) T-cells were immunized with PBS, cBSA/Alum, or cBSA/Alum/P210 according to the schedule described in earlier paragraphs and splenocytes were harvested at 13 weeks of age. CD8(+) T-cells were negatively isolated using a CD8 selection Dynabeads kit (Invitrogen) per manufacturer's protocol. The selected CD8(+) T-cells were then co-culture with DCs in a CD8:DC ratio of 3:1. A series of pilot studies has been performed to determine the optimal CD8:DC ratio for this assay. After co-culture for 4 hours, cells were collected and processed for flow cytometric determination of CD11c and 7-AAD by LSR II flow cytometer (BD Biosciences) and data was analyzed with Summit V4.3 software. Dendritic cell death without CD8(+) T-cells in the co-culture was used as baseline and percentage of specific lysis of cells was calculated using a method described previously. (20)

StatisticsData are presented as mean±Std. Number of animals in each group is listed in text or description of the figures. Data were analyzed by ANOVA followed by Newman-Keuls multiple group comparison, or by t-test when appropriate. $P<0.05$ was considered as statistically significant and horizontal bars in each figure indicated statistically significant difference between groups.

Example 1

Immunogenic Fragments of ApoB-100

Specific immunogenic epitopes by focusing on the single protein found in LDL, apolipoprotein B-100 (apo B) were characterized. A peptide library comprised of 302 peptides, 20 amino acid residues in length, covering the complete 4563 amino acid sequence of human ApoB-100 was produced. The peptides were produced with a 5 amino acid overlap to cover all sequences at break points. Peptides were numbered 1-302 starting at the N-terminal of apo B as indicated in Table 2 below.

TABLE 2

| Peptide | Sequence | Apolipoprotein B aa | SEQ ID NO |
|---|---|---|---|
| P1: | EEEML ENVSL VCPKD ATRFK | aa 1-20 | SEQ ID NO: 1 |
| P2: | ATRFK HLRKY TYNYE AESSS | aa 16-35 | SEQ ID NO: 2 |
| P3: | AESSS GVPGT ADSRS ATRIN | aa 31-50 | SEQ ID NO: 3 |
| P4: | ATRIN CKVEL EVPQL CSFIL | aa 46-65 | SEQ ID NO: 4 |
| P5: | CSFIL KTSQC TLKEV YGFNP | aa 61-80 | SEQ ID NO: 5 |
| P6: | YGFNP EGKAL LKKTK NSEEF | aa 76-95 | SEQ ID NO: 6 |
| P7: | NSEEF AAAMS RYELK LAIPE | aa 91-110 | SEQ ID NO: 7 |
| P8: | LAIPE GKQVF LYPEK DEPTY | aa 106-125 | SEQ ID NO: 8 |
| P9: | DEPTY ILNIK RGIIS ALLVP | aa 121-140 | SEQ ID NO: 9 |
| P10: | ALLVP PETEE AKQVL FLDTV | aa 136-155 | SEQ ID NO: 10 |
| P11: | FLDTV YGNCS THFTV KTRKG | aa 151-170 | SEQ ID NO: 11 |
| P12: | KTRKG NVATE ISTER DLGQC | aa 166-185 | SEQ ID NO: 12 |
| P13: | DLGQC DRFKP IRTGI SPLAL | aa 181-200 | SEQ ID NO: 13 |
| P14: | SPLAL IKGMT RPLST LISSS | aa 196-215 | SEQ ID NO: 14 |
| P15: | LISSS QSCQY TLDAK RKHVA | aa 211-230 | SEQ ID NO: 15 |
| P16: | RKHVA EAICK EQHLF LPFSY | aa 226-245 | SEQ ID NO: 16 |
| P17: | LPFSY NNKYG MVAQV TQTLK | aa 241-260 | SEQ ID NO: 17 |
| P18: | TQTLK LEDTP KINSR FFGEG | aa 256-275 | SEQ ID NO: 18 |
| P19: | FFGEG TKKMG LAFES TKSTS | aa 271-290 | SEQ ID NO: 19 |
| P20: | TKSTS PPKQA EAVLK TLQEL | aa 286-305 | SEQ ID NO: 20 |
| P21: | TLQEL KKLTI SEQNI QRANL | aa 301-320 | SEQ ID NO: 21 |
| P22: | QRANL FNKLV TELRG LSDEA | aa 316-335 | SEQ ID NO: 22 |
| P23: | LSDEA VTSLL PQLIE VSSPI | aa 331-350 | SEQ ID NO: 23 |
| P24: | VSSPI TLQAL VQCGQ PQCST | aa 346-365 | SEQ ID NO: 24 |
| P25: | PQCST HILQW LKRVH ANPLL | aa 361-380 | SEQ ID NO: 25 |

TABLE 2-continued

| Peptide | Sequence | Apolipoprotein B aa | SEQ ID NO |
|---|---|---|---|
| P26: | ANPLL IDVVT YLVAL IPEPS | aa 376-395 | SEQ ID NO: 26 |
| P27: | IPEPS AQQLR EIFNM ARDQR | aa 391-410 | SEQ ID NO: 27 |
| P28: | ARDQR SRATL YALSH AVNNY | aa 406-425 | SEQ ID NO: 28 |
| P29: | AVNNY HKTNP TGTQE LLDIA | aa 421-440 | SEQ ID NO: 29 |
| P30: | LLDIA NYLME QIQDD CTGDE | aa 436-455 | SEQ ID NO: 30 |
| P31: | CTGDE DYTYL ILRVI GNMGQ | aa 451-470 | SEQ ID NO: 31 |
| P32: | GNMGQ TMEQL TPELK SSILK | aa 466-485 | SEQ ID NO: 32 |
| P33: | SSILK CVQST KPSLM IQKAA | aa 481-500 | SEQ ID NO: 33 |
| P34: | IQKAA IQALR KMEPK DKDQE | aa 496-515 | SEQ ID NO: 34 |
| P35: | DKDQE VLLQT FLDDA SPGDK | aa 511-530 | SEQ ID NO: 35 |
| P36: | SPGDK RLAAY LMLMR SPSQA | aa 526-545 | SEQ ID NO: 36 |
| P37: | SPSQA DINKI VQILP WEQNE | aa 541-560 | SEQ ID NO: 37 |
| P38: | WEQNE QVKNF VASHI ANILN | aa 556-575 | SEQ ID NO: 38 |
| P39: | ANILN SEELD IQDLK KLVKE | aa 571-590 | SEQ ID NO: 39 |
| P40: | KLVKE ALKES QLPTV MDFRK | aa 586-605 | SEQ ID NO: 40 |
| P41: | MDFRK FSRNY QLYKS VSLPS | aa 601-620 | SEQ ID NO: 41 |
| P42: | VSLPS LDPAS AKIEG NLIFD | aa 616-635 | SEQ ID NO: 42 |
| P43: | NLIFD PNNYL PKESM LKTTL | aa 631-650 | SEQ ID NO: 43 |
| P44: | LKTTL TAFGF ASADL IEIGL | aa 646-665 | SEQ ID NO: 44 |
| P45: | IEIGL EGKGF EPTLE ALFGK | aa 661-680 | SEQ ID NO: 45 |
| P46: | ALFGK QGFFP DSVNK ALYWV | aa 676-695 | SEQ ID NO: 46 |
| P47: | ALYWV NGQVP DGVSK VLVDH | aa 691-710 | SEQ ID NO: 47 |
| P48: | VLVDH FGYTK DDKHE QDMVN | aa 706-725 | SEQ ID NO: 48 |
| P49: | QDMVN GIMLS VEKLI KDLKS | aa 721-740 | SEQ ID NO: 49 |
| P50: | KDLKS KEVPE ARAYL RILGE | aa 736-755 | SEQ ID NO: 50 |
| P51: | RILGE ELGFA SLHDL QLLGK | aa 751-770 | SEQ ID NO: 51 |
| P52: | QLLGK LLLMG ARTLQ GIPQM | aa 766-785 | SEQ ID NO: 52 |
| P53: | GIPQM IGEVI RKGSK NDFFL | aa 781-800 | SEQ ID NO: 53 |
| P54: | NDFFL HYIFM ENAFE LPTGA | aa 796-815 | SEQ ID NO: 54 |
| P55: | LPTGA GLQLQ ISSSG VIAPG | aa 811-830 | SEQ ID NO: 55 |
| P56: | VIAPG AKAGV KLEVA NMQAE | aa 826-845 | SEQ ID NO: 56 |
| P57: | NMQAE LVAKP SVSVE FVTNM | aa 841-860 | SEQ ID NO: 57 |
| P58: | FVTNM GIIIP DFARS GVQMN | aa 856-875 | SEQ ID NO: 58 |
| P59: | GVQMN TNFFH ESGLE AHVAL | aa 871-890 | SEQ ID NO: 59 |
| P60: | AHVAL KAGKL KFIIP SPKRP | aa 886-905 | SEQ ID NO: 60 |
| P61: | SPKRP VKLLS GGNTL HLVST | aa 901-920 | SEQ ID NO: 61 |
| P62: | HLVST TKTEV IPPLI ENRQS | aa 916-935 | SEQ ID NO: 62 |
| P63: | ENRQS WSVCK QVFPG LNYCT | aa 931-950 | SEQ ID NO: 63 |
| P64: | LNYCT SGAYS NASST DSASY | aa 946-965 | SEQ ID NO: 64 |

TABLE 2-continued

| Peptide | Sequence | Apolipoprotein B aa | SEQ ID NO |
|---|---|---|---|
| P65: | DSASY YPLTG DTRLE LELRP | aa 961-980 | SEQ ID NO: 65 |
| P66: | LELRP TGEIE QYSVS ATYEL | aa 976-995 | SEQ ID NO: 66 |
| P67: | ATYEL QREDR ALVDT LKFVT | aa 991-1010 | SEQ ID NO: 67 |
| P68: | LKFVT QAEGA KQTEA TMTFK | aa 1006-1025 | SEQ ID NO: 68 |
| P69: | TMTFK YNRQS MTLSS EVQIP | aa 1021-1040 | SEQ ID NO: 69 |
| P70: | EVQIP DFDVD LGTIL RVNDE | aa 1036-1055 | SEQ ID NO: 70 |
| P71: | RVNDE STEGK TSYRL TLDIQ | aa 1051-1070 | SEQ ID NO: 71 |
| P72: | TLDIQ NKKIT EVALM GHLSC | aa 1066-1085 | SEQ ID NO: 72 |
| P73: | GHLSC DTKEE RKIKG VISIP | aa 1081-1100 | SEQ ID NO: 73 |
| P74: | VISIP RLQAE ARSEI LAHWS | aa 1096-1115 | SEQ ID NO: 74 |
| P75: | LAHWS PAKLL LQMDS SATAY | aa 1111-1130 | SEQ ID NO: 75 |
| P76: | SATAY GSTVS KRVAW HYDEE | aa 1126-1145 | SEQ ID NO: 76 |
| P77: | HYDEE KIEFE WNTGT NVDTK | aa 1141-1160 | SEQ ID NO: 77 |
| P78: | NVDTK KMTSN FPVDL SDYPK | aa 1156-1175 | SEQ ID NO: 78 |
| P79: | SDYPK SLHMY ANRLL DHRVP | aa 1171-1190 | SEQ ID NO: 79 |
| P80: | DHRVP ETDMT FRHVG SKLIV | aa 1186-1205 | SEQ ID NO: 80 |
| P81: | SKLIV AMSSW LQKAS GSLPY | aa 1201-1220 | SEQ ID NO: 81 |
| P82: | GSLPY TQTLQ DHLNS LKEFN | aa 1216-1235 | SEQ ID NO: 82 |
| P83: | LKEFN LQNMG LPDFH IPENL | aa 1231-1250 | SEQ ID NO: 83 |
| P84: | IPENL FLKSD GRVKY TLNKN | aa 1246-1260 | SEQ ID NO: 84 |
| P85: | TLNKN SLKIE IPLPF GGKSS | aa 1261-1280 | SEQ ID NO: 85 |
| P86: | GGKSS RDLKM LETVR TPALH | aa 1276-1295 | SEQ ID NO: 86 |
| P87: | TPALH FKSVG FHLPS REFQV | aa 1291-1310 | SEQ ID NO: 87 |
| P88: | REFQV PTFTI PKLYQ LQVPL | aa 1306-1325 | SEQ ID NO: 88 |
| P89: | LQVPL LGVLD LSTNV YSNLY | aa 1321-1340 | SEQ ID NO: 89 |
| P90: | YSNLY NWSAS YSGGN TSTDH | aa 1336-1355 | SEQ ID NO: 90 |
| P91: | TSTDH FSLRA RYHMK ADSVV | aa 1351-1370 | SEQ ID NO: 91 |
| P92: | ADSVV DLLSY NVQGS GETTY | aa 1366-1385 | SEQ ID NO: 92 |
| P93: | GETTY DHKNT FTLSC DGSLR | aa 1381-1400 | SEQ ID NO: 93 |
| P94: | DGSLR HKFLD SNIKF SHVEK | aa 1396-1415 | SEQ ID NO: 94 |
| P95: | SHVEK LGNNP VSKGL LIFDA | aa 1411-1430 | SEQ ID NO: 95 |
| P96: | LIFDA SSSWG PQMSA SVHLD | aa 1426-1445 | SEQ ID NO: 96 |
| P97: | SVHLD SKKKQ HLFVK EVKID | aa 1441-1460 | SEQ ID NO: 97 |
| P98: | EVKID GQFRV SSFYA KGTYG | aa 1456-1475 | SEQ ID NO: 98 |
| P99: | KGTYG LSCQR DPNTG RLNGE | aa 1471-1490 | SEQ ID NO: 99 |
| P100: | RLNGE SNLRF NSSYL QGTNQ | aa 1486-1505 | SEQ ID NO: 100 |
| P101: | QGTNQ ITGRY EDGTL SLTST | aa 1501-1520 | SEQ ID NO: 101 |
| P102: | SLTST SDLQS GIIKN TASLK | aa 1516-1535 | SEQ ID NO: 102 |
| P103: | TASLK YENYE LTLKS DTNGK | aa 1531-1550 | SEQ ID NO: 103 |

TABLE 2-continued

| Peptide | Sequence | Apolipoprotein B aa | SEQ ID NO |
|---|---|---|---|
| P104: | DTNGK YKNFA TSNKM DMTFS | aa 1546-1565 | SEQ ID NO: 104 |
| P105: | DMTFS KQNAL LRSEY QADYE | aa 1561-1580 | SEQ ID NO: 105 |
| P106: | QADYE SLRFF SLLSG SLNSH | aa 1576-1595 | SEQ ID NO: 106 |
| P107: | SLNSH GLELN ADILG TDKIN | aa 1591-1610 | SEQ ID NO: 107 |
| P108: | TDKIN SGAHK ATLRI GQDGI | aa 1606-1625 | SEQ ID NO: 108 |
| P109: | GQDGI STSAT TNLKC SLLVL | aa 1621-1640 | SEQ ID NO: 109 |
| P110: | SLLVL ENELN AELGL SGASM | aa 1636-1655 | SEQ ID NO: 110 |
| P111: | SGASM KLTTN GRFRE HNAKF | aa 1651-1670 | SEQ ID NO: 111 |
| P112: | HNAKF SLDGK AALTE LSLGS | aa 1666-1685 | SEQ ID NO: 112 |
| P113: | LSLGS AYQAM ILGVD SKNIF | aa 1681-1700 | SEQ ID NO: 113 |
| P114: | SKNIF NFKVS QEGLK LSNDM | aa 1696-1715 | SEQ ID NO: 114 |
| P115: | LSNDM MGSYA EMKFD HTNSL | aa 1711-1730 | SEQ ID NO: 115 |
| P116: | HTNSL NIAGL SLDFS SKLDN | aa 1726-1745 | SEQ ID NO: 116 |
| P117: | SKLDN IYSSD KFYKQ TVNLQ | aa 1741-1760 | SEQ ID NO: 117 |
| P118: | TVNLQ LQPYS LVTTL NSDLK | aa 1756-1775 | SEQ ID NO: 118 |
| P119: | NSDLK YNALD LTNNG KLRLE | aa 1771-1790 | SEQ ID NO: 119 |
| P120: | KLRLE PLKLH VAGNL KGAYQ | aa 1786-1805 | SEQ ID NO: 120 |
| P121: | KGAYQ NNEIK HIYAI SSAAL | aa 1801-1820 | SEQ ID NO: 121 |
| P122: | SSAAL SASYK ADTVA KVQGV | aa 1816-1835 | SEQ ID NO: 122 |
| P123: | KVQGV EFSHR LNTDI AGLAS | aa 1831-1850 | SEQ ID NO: 123 |
| P124: | AGLAS AIDMS TNYNS DSLHF | aa 1846-1865 | SEQ ID NO: 124 |
| P125: | DSLHF SNVFR SVMAP FTMTI | aa 1861-1880 | SEQ ID NO: 125 |
| P126: | FTMTI DAHTN GNGKL ALWGE | aa 1876-1895 | SEQ ID NO: 126 |
| P127: | ALWGE HTGQL YSKFL LKAEP | aa 1891-1910 | SEQ ID NO: 127 |
| P128: | LKAEP LAFTF SHDYK GSTSH | aa 1906-1925 | SEQ ID NO: 128 |
| P129: | GSTSH HLVSR KSISA ALEHK | aa 1921-1940 | SEQ ID NO: 129 |
| P130: | ALEHK VSALL TPAEQ TGTWK | aa 1936-1955 | SEQ ID NO: 130 |
| P131: | TGTWK LKTQF NNNEY SQDLD | aa 1951-1970 | SEQ ID NO: 131 |
| P132: | SQDLD AYNTK DKIGV ELTGR | aa 1966-1985 | SEQ ID NO: 132 |
| P133: | ELTGR TLADL TLLDS PIKVP | aa 1981-2000 | SEQ ID NO: 133 |
| P134: | PIKVP LLLSE PINII DALEM | aa 1996-2015 | SEQ ID NO: 134 |
| P135: | DALEM RDAVE KPQEF TIVAF | aa 2011-2030 | SEQ ID NO: 135 |
| P136: | TIVAF VKYDK NQDVH SINLP | aa 2026-2045 | SEQ ID NO: 136 |
| P137: | SINLP FFETL QEYFE RNRQT | aa 2041-2060 | SEQ ID NO: 137 |
| P138: | RNRQT IIVVV ENVQR NLKHI | aa 2056-2075 | SEQ ID NO: 138 |
| P139: | NLKHI NIDQF VRKYR AALGK | aa 2071-2090 | SEQ ID NO: 139 |
| P140: | AALGK LPQQA NDYLN SFNWE | aa 2086-2105 | SEQ ID NO: 140 |
| P141: | SFNWE RQVSH AKEKL TALTK | aa 2101-2120 | SEQ ID NO: 141 |
| P142: | TALTK KYRIT ENDIQ IALDD | aa 2116-2135 | SEQ ID NO: 142 |

TABLE 2-continued

| Peptide | Sequence | Apolipoprotein B aa | SEQ ID NO |
|---|---|---|---|
| P143: | IALDD AKINF NEKLS QLQTY | aa 2131-2150 | SEQ ID NO: 143 |
| P144: | QLQTY MIQFD QYIKD SYDLH | aa 2146-2165 | SEQ ID NO: 144 |
| P145: | SYDLH DLKIA IANII DEIIE | aa 2161-2180 | SEQ ID NO: 145 |
| P146: | DEIIE KLKSL DEHYH IRVNL | aa 2176-2195 | SEQ ID NO: 146 |
| P147: | IRVNL VKTIH DLHLF IENID | aa 2191-2210 | SEQ ID NO: 147 |
| P148: | IENID FNKSG SSTAS WIQNV | aa 2206-2225 | SEQ ID NO: 148 |
| P149: | WIQNV DTKYQ IRIQI QEKLQ | aa 2221-2240 | SEQ ID NO: 149 |
| P150: | QEKLQ QLKRH IQNID IQHLA | aa 2236-2255 | SEQ ID NO: 150 |
| P151: | IQHLA GKLKQ HIEAI DVRVL | aa 2251-2270 | SEQ ID NO: 151 |
| P152: | DVRVL LDQLG TTISF ERIND | aa 2266-2285 | SEQ ID NO: 152 |
| P153: | ERIND VLEHV KHFVI NLIGD | aa 2281-2300 | SEQ ID NO: 153 |
| P154: | NLIGD FEVAE KINAF RAKVH | aa 2296-2315 | SEQ ID NO: 154 |
| P155: | RAKVH ELIER YEVDQ QIQVL | aa 2311-2330 | SEQ ID NO: 155 |
| P156: | QIQVL MDKLV ELTHQ YKLKE | aa 2326-2345 | SEQ ID NO: 156 |
| P157: | YKLKE TIQKL SNVLQ QVKIK | aa 2341-2360 | SEQ ID NO: 157 |
| P158: | QVKIK DYFEK LVGFI DDAVK | aa 2356-2375 | SEQ ID NO: 158 |
| P159: | DDAVK KLNEL SFKTF IEDVN | aa 2371-2390 | SEQ ID NO: 159 |
| P160: | IEDVN KFLDM LIKKL KSFDY | aa 2386-2405 | SEQ ID NO: 160 |
| P161: | KSFDY HQFVD ETNDK IREVT | aa 2401-2420 | SEQ ID NO: 161 |
| P162: | IREVT QRLNG EIQAL ELPQK | aa 2416-2435 | SEQ ID NO: 162 |
| P163: | ELPQK AEALK LFLEE TKATV | aa 2431-2450 | SEQ ID NO: 163 |
| P164: | TKATV AVYLE SLQDT KITLI | aa 2446-2465 | SEQ ID NO: 164 |
| P165: | KITLI INWLQ EALSS ASLAH | aa 2461-2480 | SEQ ID NO: 165 |
| P166: | ASLAH MKAKF RETLE DTRDR | aa 2476-2495 | SEQ ID NO: 166 |
| P167: | DTRDR MYQMD IQQEL QRYLS | aa 2491-2510 | SEQ ID NO: 167 |
| P168: | QRYLS LVGQV YSTLV TYISD | aa 2506-2515 | SEQ ID NO: 168 |
| P169: | TYISD WWTLA AKNLT DFAEQ | aa 2521-2540 | SEQ ID NO: 169 |
| P170: | DFAEQ YSIQD WAKRM KALVE | aa 2536-2555 | SEQ ID NO: 170 |
| P171: | KALVE QGFTV PEIKT ILGTM | aa 2551-2570 | SEQ ID NO: 171 |
| P172: | ILGTM PAFEV SLQAL QKATF | aa 2566-2585 | SEQ ID NO: 172 |
| P173: | QKATF QTPDF IVPLT DLRIP | aa 2581-2600 | SEQ ID NO: 173 |
| P174: | DLRIP SVQIN FKDLK NIKIP | aa 2596-2615 | SEQ ID NO: 174 |
| P175: | NIKIP SRFST PEFTI LNTFH | aa 2611-2630 | SEQ ID NO: 175 |
| P176: | LNTFH IPSFT IDFVE MKVKI | aa 2626-2645 | SEQ ID NO: 176 |
| P177: | MKVKI IRTID QMQNS ELQWP | aa 2641-2660 | SEQ ID NO: 177 |
| P178: | ELQWP VPDIY LRDLK VEDIP | aa 2656-2675 | SEQ ID NO: 178 |
| P179: | VEDIP LARIT LPDFR LPEIA | aa 2671-2690 | SEQ ID NO: 179 |
| P180: | LPEIA IPEFI IPTLN LNDFQ | aa 2686-2705 | SEQ ID NO: 180 |
| P181: | LNDFQ VPDLH IPEFQ LPHIS | aa 2701-2720 | SEQ ID NO: 181 |

TABLE 2-continued

| Peptide | Sequence | Apolipoprotein B aa | SEQ ID NO |
|---|---|---|---|
| P182: | LPHIS HTIEV PTFGK LYSIL | aa 2716-2735 | SEQ ID NO: 182 |
| P183: | LYSIL KIQSP LFTLD ANADI | aa 2731-2750 | SEQ ID NO: 183 |
| P184: | ANADI GNGTT SANEA GIAAS | aa 2746-2765 | SEQ ID NO: 184 |
| P185: | GIAAS ITAKG ESKLE VLNFD | aa 2761-2780 | SEQ ID NO: 185 |
| P186: | VLNFD FQANA QLSNP KINPL | aa 2776-2795 | SEQ ID NO: 186 |
| P187: | KINPL ALKES VKFSS KYLRT | aa 2791-2810 | SEQ ID NO: 187 |
| P188: | KYLRT EHGSE MLFFG NAIEG | aa 2806-2825 | SEQ ID NO: 188 |
| P189: | NAIEG KSNTV ASLHT EKNTL | aa 2821-2840 | SEQ ID NO: 189 |
| P190: | EKNTL ELSNG VIVKI NNQLT | aa 2836-2855 | SEQ ID NO: 190 |
| P191: | NNQLT LDSNT KYFHK LNIPK | aa 2851-2870 | SEQ ID NO: 191 |
| P192: | LNIPK LDFSS QADLR NEIKT | aa 2866-2885 | SEQ ID NO: 192 |
| P193: | NEIKT LLKAG HIAWT SSGKG | aa 2881-2900 | SEQ ID NO: 193 |
| P194: | SSGKG SWKWA CPRFS DEGTH | aa 2896-2915 | SEQ ID NO: 194 |
| P195: | DEGTH ESQIS FTIEG PLTSF | aa 2911-2930 | SEQ ID NO: 195 |
| P196: | PLTSF GLSNK INSKH LRVNQ | aa 2926-2945 | SEQ ID NO: 196 |
| P197: | LRVNQ NLVYE SGSLN FSKLE | aa 2941-2960 | SEQ ID NO: 197 |
| P198: | FSKLE IQSQV DSQHV GHSVL | aa 2956-2975 | SEQ ID NO: 198 |
| P199: | GHSVL TAKGM ALFGE GKAEF | aa 2971-2990 | SEQ ID NO: 199 |
| P200: | GKAEF TGRHD AHLNG KVIGT | aa 2986-3005 | SEQ ID NO: 200 |
| P201: | KVIGT LKNSL FFSAQ PFEIT | aa 3001-3020 | SEQ ID NO: 201 |
| P202: | PFEIT ASTNN EGNLK VRFPL | aa 3016-3035 | SEQ ID NO: 202 |
| P203: | VRFPL RLTGK IDFLN NYALF | aa 3031-3050 | SEQ ID NO: 203 |
| P204: | NYALF LSPSA QQASW QVSAR | aa 3046-3065 | SEQ ID NO: 204 |
| P205: | QVSAR FNQYK YNQNF SAGNN | aa 3061-3080 | SEQ ID NO: 205 |
| P206: | SAGNN ENIME AHVGI NGEAN | aa 3076-3095 | SEQ ID NO: 206 |
| P207: | NGEAN LDFLN IPLTI PEMRL | aa 3091-3110 | SEQ ID NO: 207 |
| P208: | PEMRL PYTII TTPPL KDFSL | aa 3106-3125 | SEQ ID NO: 208 |
| P209: | KDFSL WEKTG LKEFL KTTKQ | aa 3121-3140 | SEQ ID NO: 209 |
| P210: | KTTKQ SFDLS VKAQY KKNKH | aa 3136-3155 | SEQ ID NO: 210 |
| P211: | KKNKH RHSIT NPLAV LCEFI | aa 3151-3170 | SEQ ID NO: 211 |
| P212: | LCEFI SQSIK SFDRH FEKNR | aa 3166-3185 | SEQ ID NO: 212 |
| P213: | FEKNR NNALD FVTKS YNETK | aa 3181-3200 | SEQ ID NO: 213 |
| P214: | YNETK IKFDK YKAEK SHDEL | aa 3196-3215 | SEQ ID NO: 214 |
| P215: | SHDEL PRTFQ IPGYT VPVVN | aa 3211-3230 | SEQ ID NO: 215 |
| P216: | VPVVN VEVSP FTIEM SAFGY | aa 3226-3245 | SEQ ID NO: 216 |
| P217: | SAFGY VFPKA VSMPS FSILG | aa 3241-3260 | SEQ ID NO: 217 |
| P218: | FSILG SDVRV PSYTL ILPSL | aa 3256-3275 | SEQ ID NO: 218 |
| P219: | ILPSL ELPVL HVPRN LKLSL | aa 3271-3290 | SEQ ID NO: 219 |
| P220: | LKLSL PHFKE LCTIS HIFIP | aa 3286-3305 | SEQ ID NO: 220 |

TABLE 2-continued

| Peptide | Sequence | Apolipoprotein B aa | SEQ ID NO |
|---|---|---|---|
| P221: | HIFIP AMGNI TYDFS FKSSV | aa 3301-3320 | SEQ ID NO: 221 |
| P222: | FKSSV ITLNT NAELF NQSDI | aa 3316-3335 | SEQ ID NO: 222 |
| P223: | NQSDI VAHLL SSSSS VIDAL | aa 3331-3350 | SEQ ID NO: 223 |
| P224: | VIDAL QYKLE GTTRL TRKRG | aa 3346-3365 | SEQ ID NO: 224 |
| P225: | TRKRG LKLAT ALSLS NKFVE | aa 3361-3380 | SEQ ID NO: 225 |
| P226: | NKFVE GSHNS TVSLT TKNME | aa 3376-3395 | SEQ ID NO: 226 |
| P227: | TKNME VSVAK TTKAE IPILR | aa 3391-3410 | SEQ ID NO: 227 |
| P228: | IPILR MNFKQ ELNGN TKSKP | aa 3406-3425 | SEQ ID NO: 228 |
| P229: | TKSKP TVSSS MEFKY DFNSS | aa 3421-3440 | SEQ ID NO: 229 |
| P230: | DFNSS MLYST AKGAV DHKLS | aa 3436-3455 | SEQ ID NO: 230 |
| P231: | DHKLS LESLT SYFSI ESSTK | aa 3451-3470 | SEQ ID NO: 231 |
| P232: | ESSTK GDVKG SVLSR EYSGT | aa 3466-3485 | SEQ ID NO: 232 |
| P233: | EYSGT IASEA NTYLN SKSTR | aa 3481-3500 | SEQ ID NO: 233 |
| P234: | SKSTR SSVKL QGTSK IDDIW | aa 3496-3515 | SEQ ID NO: 234 |
| P235: | IDDIW NLEVK ENFAG EATLQ | aa 3511-3530 | SEQ ID NO: 235 |
| P236: | EATLQ RIYSL WEHST KNHLQ | aa 3526-3545 | SEQ ID NO: 236 |
| P237: | KNHLQ LEGLF TNGE HTSKA | aa 3541-3560 | SEQ ID NO: 237 |
| P238: | HTSKA TLELS PWQMS ALVQV | aa 3556-3575 | SEQ ID NO: 238 |
| P239: | ALVQV HASQP SSFHD FPDLG | aa 3571-3590 | SEQ ID NO: 239 |
| P240: | FPDLG QEVAL NANTK NQKIR | aa 3586-3605 | SEQ ID NO: 240 |
| P241: | NQKIR WKNEV RIHSG SFQSQ | aa 3601-3620 | SEQ ID NO: 241 |
| P242: | SFQSQ VELSN DQEKA HLDIA | aa 3616-3635 | SEQ ID NO: 242 |
| P243: | HLDIA GSLEG HLRFL KNIIL | aa 3631-3650 | SEQ ID NO: 243 |
| P244: | KNIIL PVYDK SLWDF LKLDV | aa 3646-3665 | SEQ ID NO: 244 |
| P245: | LKLDV TTSIG RRQHL RVSTA | aa 3661-3680 | SEQ ID NO: 245 |
| P246: | RVSTA FVYTK NPNGY SFSIP | aa 3676-3695 | SEQ ID NO: 246 |
| P247: | SFSIP VKVLA DKFIT PGLKL | aa 3691-3710 | SEQ ID NO: 247 |
| P248: | PGLKL NDLNS VLVMP TFHVP | aa 3706-3725 | SEQ ID NO: 248 |
| P249: | TFHVP FTDLQ VPSCK LDFRE | aa 3721-3740 | SEQ ID NO: 249 |
| P250: | LDFRE IQIYK KLRTS SFALN | aa 3736-3755 | SEQ ID NO: 250 |
| P251: | SFALN LPTLP EVKFP EVDVL | aa 3751-3770 | SEQ ID NO: 251 |
| P252: | EVDVL TKYSQ PEDSL IPFFE | aa 3766-3785 | SEQ ID NO: 252 |
| P253: | IPFFE ITVPE SQLTV SQFTL | aa 3781-3800 | SEQ ID NO: 253 |
| P254: | SQFTL PKSVS DGIAA LDLNA | aa 3796-3815 | SEQ ID NO: 254 |
| P255: | LDLNA VANKI ADFEL PTIIV | aa 3811-3830 | SEQ ID NO: 255 |
| P256: | PTIIV PEQTI EIPSI KFSVP | aa 3826-3845 | SEQ ID NO: 256 |
| P257: | KFSVP AGIVI PSFQA LTARF | aa 3841-3860 | SEQ ID NO: 257 |
| P258: | LTARF EVDSP VYNAT WSASL | aa 3856-3875 | SEQ ID NO: 258 |
| P259: | WSASL KNKAD YVETV LDSTC | aa 3871-3890 | SEQ ID NO: 259 |

TABLE 2-continued

| Peptide | Sequence | Apolipoprotein B aa | SEQ ID NO |
|---|---|---|---|
| P260: | LDSTC SSTVQ FLEYE LNVLG | aa 3886-3905 | SEQ ID NO: 260 |
| P261: | LNVLG THKIE DGTLA SKTKG | aa 3901-3920 | SEQ ID NO: 261 |
| P262: | SKTKG TLAHR DFSAE YEEDG | aa 3916-3935 | SEQ ID NO: 262 |
| P263: | YEEDG KFEGL QEWEG KAHLN | aa 3931-3950 | SEQ ID NO: 263 |
| P264: | KAHLN IKSPA FTDLH LRYQK | aa 3946-3965 | SEQ ID NO: 264 |
| P265: | LRYQK DKKGI STSAA SPAVG | aa 3961-3980 | SEQ ID NO: 265 |
| P266: | SPAVG TVGMD MDEDD DFSKW | aa 3976-3995 | SEQ ID NO: 266 |
| P267: | DFSKW NFYYS PQSSP DKKLT | aa 3991-4010 | SEQ ID NO: 267 |
| P268: | DKKLT IFKTE LRVRE SDEET | aa 4006-4025 | SEQ ID NO: 268 |
| P269: | SDEET QIKVN WEEEA ASGLL | aa 4021-4040 | SEQ ID NO: 269 |
| P270: | ASGLL TSLKD NVPKA TGVLY | aa 4036-4055 | SEQ ID NO: 270 |
| P271: | TGVLY DYVNK YHWEH TGLTL | aa 4051-4070 | SEQ ID NO: 271 |
| P272: | TGLTL REVSS KLRRN LQNNA | aa 4066-4085 | SEQ ID NO: 272 |
| P273: | LQNNA EWVYQ GAIRQ IDDID | aa 4081-4100 | SEQ ID NO: 273 |
| P274: | IDDID VRFQK AASGT TGTYQ | aa 4096-4115 | SEQ ID NO: 274 |
| P275: | TGTYQ EWKDK AQNLY QELLT | aa 4111-4130 | SEQ ID NO: 275 |
| P276: | QELLT QEGQA SFQGL KDNVF | aa 4126-4145 | SEQ ID NO: 276 |
| P277: | KDNVF DGLVR VTQKF HMKVK | aa 4141-4160 | SEQ ID NO: 277 |
| P278: | HMKVK HLIDS LIDFL NFPRF | aa 4156-4175 | SEQ ID NO: 278 |
| P279: | NFPRF QFPGK PGIYT REELC | aa 4171-4190 | SEQ ID NO: 279 |
| P280: | REELC TMFIR EVGTV LSQVY | aa 4186-4205 | SEQ ID NO: 280 |
| P281: | LSQVY SKVHN GSEIL FSYFQ | aa 4201-4220 | SEQ ID NO: 281 |
| P282: | FSYFQ DLVIT LPFEL RKHKL | aa 4216-4235 | SEQ ID NO: 282 |
| P283: | RKHKL IDVIS MYREL LKDLS | aa 4231-4250 | SEQ ID NO: 283 |
| P284: | LKDLS KEAQE VFKAI QSLKT | aa 4246-4265 | SEQ ID NO: 284 |
| P285: | QSLKT TEVLR NLQDL LQFIF | aa 4261-4280 | SEQ ID NO: 285 |
| P286: | LQFIF QLIED NIKQL KEMKF | aa 4276-4295 | SEQ ID NO: 286 |
| P287: | KEMKF TYLIN YIQDE INTIF | aa 4291-4310 | SEQ ID NO: 287 |
| P288: | INTIF NDYIP YVFKL LKENL | aa 4306-4325 | SEQ ID NO: 288 |
| P289: | LKENL CLNLH KFNEF IQNEL | aa 4321-4340 | SEQ ID NO: 289 |
| P290: | IQNEL QEASQ ELQQI HQYIM | aa 4336-4355 | SEQ ID NO: 290 |
| P291: | HQYIM ALREE YFDPS IVGWT | aa 4351-4370 | SEQ ID NO: 291 |
| P292: | IVGWT VKYYE LEEKI VSLIK | aa 4366-4385 | SEQ ID NO: 292 |
| P293: | VSLIK NLLVA LKDFH SEYIV | aa 4381-4400 | SEQ ID NO: 293 |
| P294: | SEYIV SASNF TSQLS SQVEQ | aa 4396-4415 | SEQ ID NO: 294 |
| P295: | SQVEQ FLHRN IQEYL SILTD | aa 4411-4430 | SEQ ID NO: 295 |
| P296: | SILTD PDGKG KEKIA ELSAT | aa 4426-4445 | SEQ ID NO: 296 |
| P297: | ELSAT AQEII KSQAI ATKKI | aa 4441-4460 | SEQ ID NO: 297 |
| P298: | TKKII SDYHQ QFRYK LQDFS | aa 4457-4476 | SEQ ID NO: 298 |

TABLE 2-continued

| Peptide | Sequence | Apolipoprotein B aa | SEQ ID NO |
|---|---|---|---|
| P299: | LQDFS DQLSD YYEKF IAESK | aa 4472-4491 | SEQ ID NO: 299 |
| P300: | IAESK RLIDL SIQNY HTFLI | aa 4487-4506 | SEQ ID NO: 300 |
| P301: | HTFLI YITEL LKKLQ STTVM | aa 4502-4521 | SEQ ID NO: 301 |
| P302: | STTVM NPYMK LAPGE LTIIL | aa 4517-4536 | SEQ ID NO: 302 |

The full length sequence of ApoB 100 can be found in various publications such as reference (43) (see in particular FIG. 1) herein incorporated by reference in its entirety.

Example 2

ApoB-100 Related Peptide P210 Immunization Reduces Blood Pressure Induced by Angiotensin Male apoE KO mice were subcutaneously immunized at 7, 10, and 12 weeks of age with 100 μg of either Group 1: P210/cBSA conjugate using alum as adjuvant (P210); Group 2: control-100 μg of cBSA/alum (cBSA); Group 3: control PBS (PBS). 14 P210, 17 cBSA, 16 PBS, and 8 Saline injected mice were examined.

AngII (1000 ng/Kg/min) was delivered by a subcutaneous osmotic pump implanted at 10 weeks of age for 4 weeks to cause an increase in blood pressure in all three groups. Saline was delivered to the control group. Mice were sacrificed at 14 weeks of age of age. The mice were fed normal chow for the duration of the experiment.

Figure 2A:
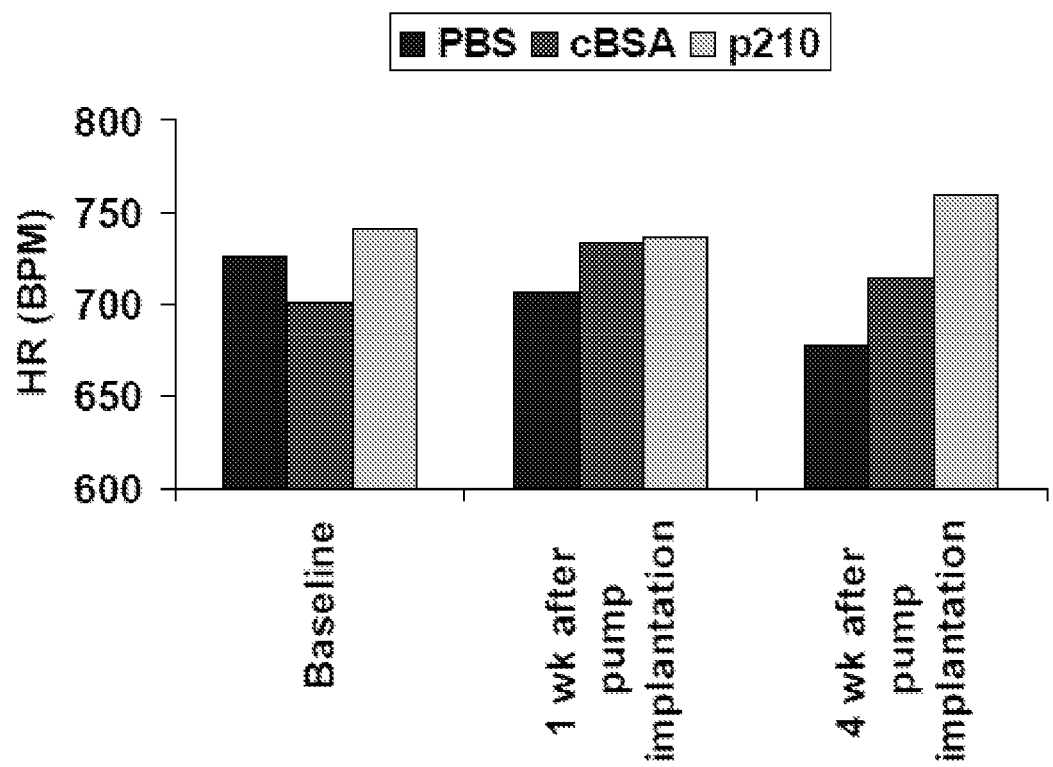
FIGS. 2A and 2B show the effect of p210 immunization on heart rate in various groups of mice according to embodiments herein described.
Figure 2B:
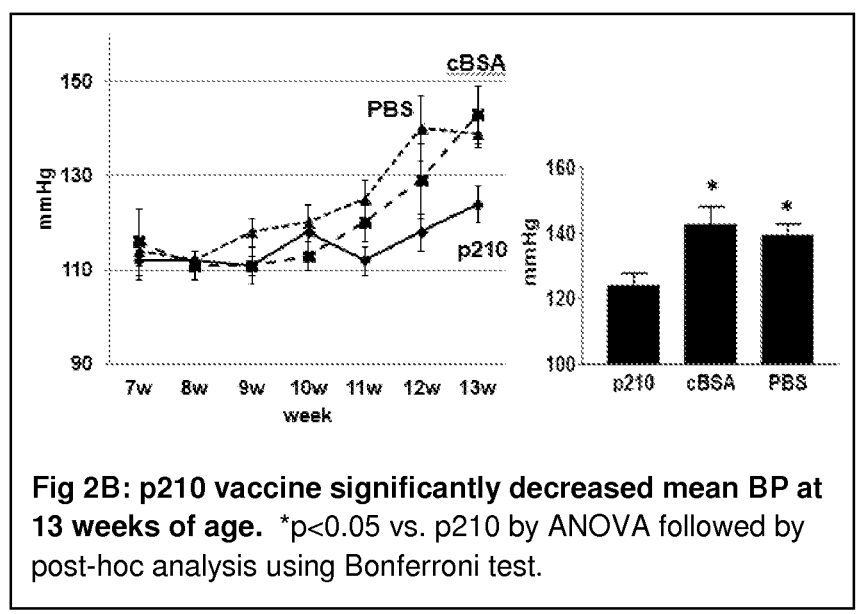

FIG. 1 shows an approximate 11% reduction in blood pressure in P210 vaccinated mice 4 weeks after pump implantation with a concomitant approximate 7% change in hearth rate in P210 vaccinated mice 4 weeks after pump implantation (FIG. 2A). FIG. 2B shows the time course of mean blood pressure change throughout the duration of experiments. Mice received treatment (PBS, cBSA/alum or p210/cBSA/ alum) at 7, 10 and 12 weeks of age. Angiotensin II infusion via implanted osmotic pump was started at 10 weeks of age. Mice were euthanized at 14 weeks of age. Blood pressure was measured throughout the duration of experiment. Mean blood pressure gradually increased after angiotensin II infusion was started. At 13 weeks of age, mice immunized with p210/ cBSA/alum had a significantly lower mean blood pressure when compared to that in the other 2 groups.

According to the above data it is expected that a p210 vaccine can prevent HTN.

A possible mechanism of action provided herein for guidance purposes only and not intended to be limiting is that p210 immunization reduces BP; and that the effect of p210 immunization is mediated by CD8 to a same or comparable extent detected for reduction of atherosclerosis illustrated in the following examples. Accordingly, ability to elicit a T cell response is specific for p210 (antigen specificity) and other apoB-100 peptides are expected to show similar antigen-specific CD8 effect.

A further possible mechanism of action provided herein for guidance purposes only and not intended to be limiting is that p210 action is performed also through modulation of angiotensin expression. Based on published anti-HTN vaccine literature, an anti-angiotensin vaccine can treat HTN. As a consequence, based on anti-angiotensin vaccine, multiple administration can be desired in certain condition and for certain types of individuals.

Example 3

Athero-Protective Effects of p210 Immunization

The vaccine preparation consisted of the p210 peptide (Euro-Diagnostica AB, Sweden) conjugated to cationic bovine serum albumin (cBSA) as carrier using a method described previously[3;4]. Alum was used as adjuvant and mixed with peptide/cBSA conjugated with 1:1 ratio in volume. Peptide conjugation was performed on the day of immunization and freshly mixed with alum just prior to each immunization. Mice fed normal chow diet received subcutaneous primary immunization in the dorsal area between scapulas at 6-7 weeks of age, followed by a booster at 10 and 12 weeks of age. One week after the last booster, diet was switched to high cholesterol chow (TD 88137, Harlan-Teklad) and continued until euthanasia at the age of 25 weeks.

Figure 3:
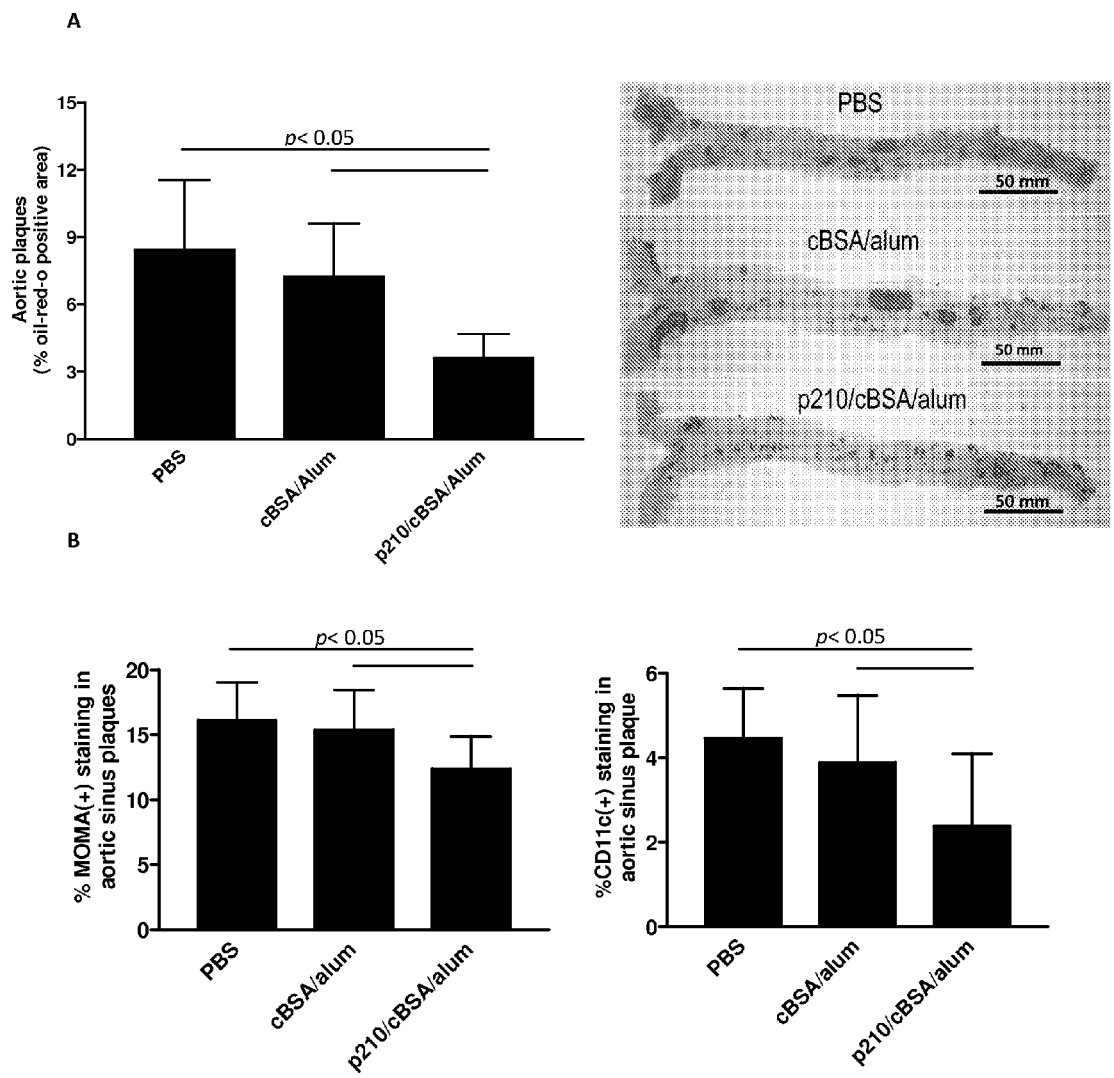
FIG. 3 shows p210 immunization confers athero-protective effect. (A) Immunization with native p210 resulted in a significant reduction in aortic atherosclerosis when compared to PBS and cBSA/Alum group (n=9-10 each group, representative picture from each group shown). (B) P210 immunization significantly reduced macrophage infiltration and DC presence assessed by MOMA-2 (n=9-10 each group) and CD11c (n=7-12 each group) immuno-reactivity, respectively in aortic sinus plaques.

Immunization with p210 reduced aortic atherosclerosis by 57% and 50% compared to PBS and cBSA/Alum group, respectively (FIG. 3A) without affecting circulating cholesterol levels or body weight (Table 3).

TABLE 3

Circulating level of cholesterol and body weight of mice from PBS, cBSA/alum and p210/cBSA/alum group

|  | PBS (n = 10) | cBSA/alum (n = 10) | P210/cBSA/alum (n = 10) | P value (ANOVA) |
|---|---|---|---|---|
| Cholesterol (mg/dl) | 1503 ± 485 | 1395 ± 420 | 1135 ± 382 | 0.17 |
| Body weight (gm) | 37.9 ± 5.4 | 34.8 ± 5.4 | 34.3 ± 6.5 | 0.33 |

The aortic sinus plaques from p210/cBSA/alum group contained significantly reduced macrophage and DC immuno-reactivity assessed by MOMA-2 and CD11c immuno-staining, respectively (FIG. 3B) with no difference in the atherosclerotic lesions (PBS group 0.40±0.13 mm$^2$, n=10; cBSA/alum group 0.42±0.09 mm$^2$, n=10; p210/cBSA/alum group 0.40±0.08 mm$^2$, n=9).

Example 4

Characterization of p210-Immunization Elicited Immune Responses

Since DCs are the major cell type upstream to both cellular and humoral immune responses, Applicants determined if these cells were affected by the immunization strategy. Cells from the subcutaneous immunization sites were isolated for flow cytometric analysis one week after primary immunization. The PBS group could not be included in this analysis because mice receiving PBS injection did not develop swelling or cell accumulation at the injection site.

Figure 4:
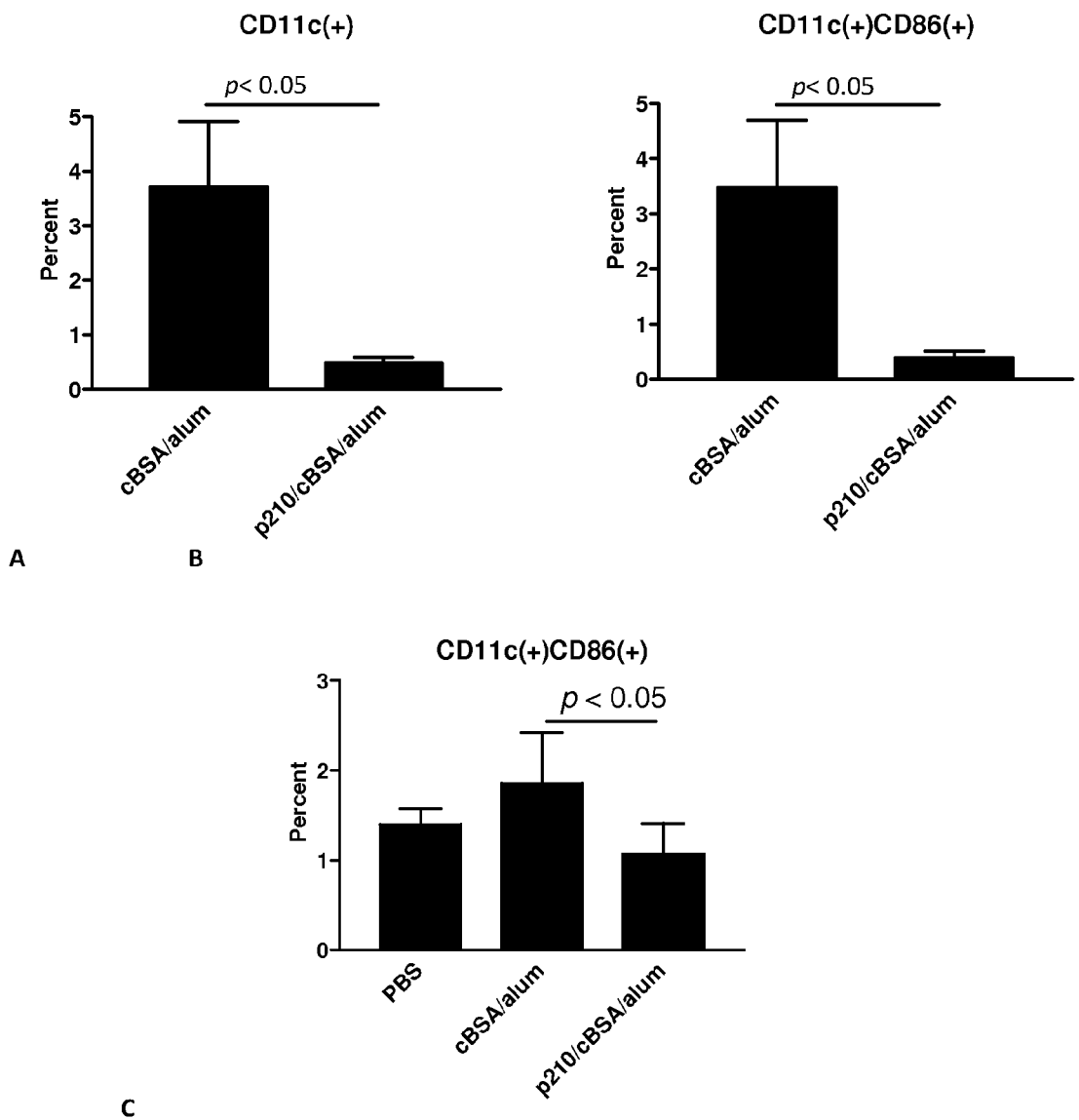
FIG. 4 Effect of p210 immunization on DCs. One week after primary immunization, (A) CD11c(+) or (B) CD11c(+) CD86(+) cells at the immunization sites was significantly reduced in p210/cBSA/alum group when compared to cBSA/alum group. N=10 each group. (C) One week after third immunization, p210 immunized mice had reduced CD11c(+) CD86(+) cells in lymph nodes compared to cBSA/alum group (n=5 in each group; ANOVA followed by multiple group comparison).

There were significantly fewer CD11c(+) and CD11c(+) CD86(+) cells in p210/cBSA/alum group compared to cBSA/alum group at the immunization site (FIGS. 4A and 4B). When flow cytometry was performed on LN cells 1 week after the third immunization, CD11c(+)CD86(+) cells were also significantly reduced compared with cBSA/alum group (FIG. 4C).

Figure 5:
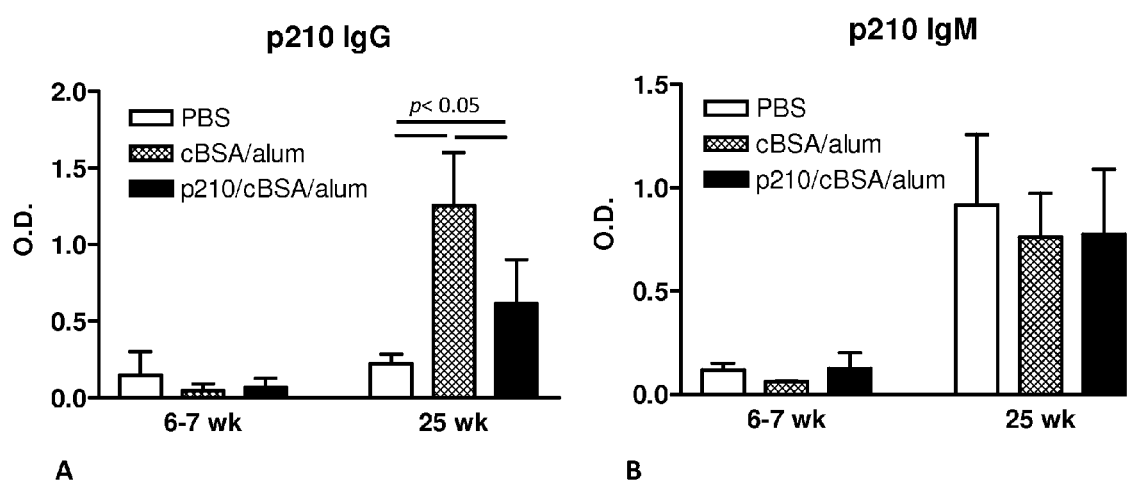
FIG. 5 shows IgM or IgG titer against p210 before and after p210 immunization. (A) The p210 IgG titers were low before immunization and remained low in the PBS group at euthanasia but significantly increased in cBSA/alum and p210/cBSA/alum groups, with the highest titer in the cBSA/alum group. (B) The p210 IgM titers were low before immunization and significantly increased at euthanasia with no difference among 3 groups of mice. N=5 for 6-7 week time-point and n=9 for 25 week time-point.

Applicants next assessed antibody response to define the humoral immune response against p210. Before immunization all 3 groups of mice had low levels of IgG titers against p210. At euthanasia, the IgG titer against p210 remained low in the PBS group but was significantly increased in cBSA/alum group. Immunization with p210/cBSA/alum resulted in increased p210 IgG titer compared with PBS group but was significantly reduced compared with cBSA/alum group (FIG. 5A). In contrast to p210 IgG response, there was a significant increase in p210 IgM titer in all groups (FIG. 5B), suggesting an endogenous immune response against p210.

The IL-2Rα (CD25) is a well-defined lymphocyte activation marker. Applicants therefore analyzed the expression of CD25 on CD4(+) or CD8(+) T-cells from superficial cervical and axillary lymph nodes (LN) from mice one week after primary immunization to assess the T-cell immune response. CD8(+)CD25(+) T-cell population in the lymph nodes was significantly higher in p210/cBSA/alum group when compared to that of PBS or cBSA/alum groups (FIG. 6A) whereas CD4(+)CD25(+) T-cells in the lymph nodes (FIG. 6B) did not differ among 3 groups.

Figure 6:
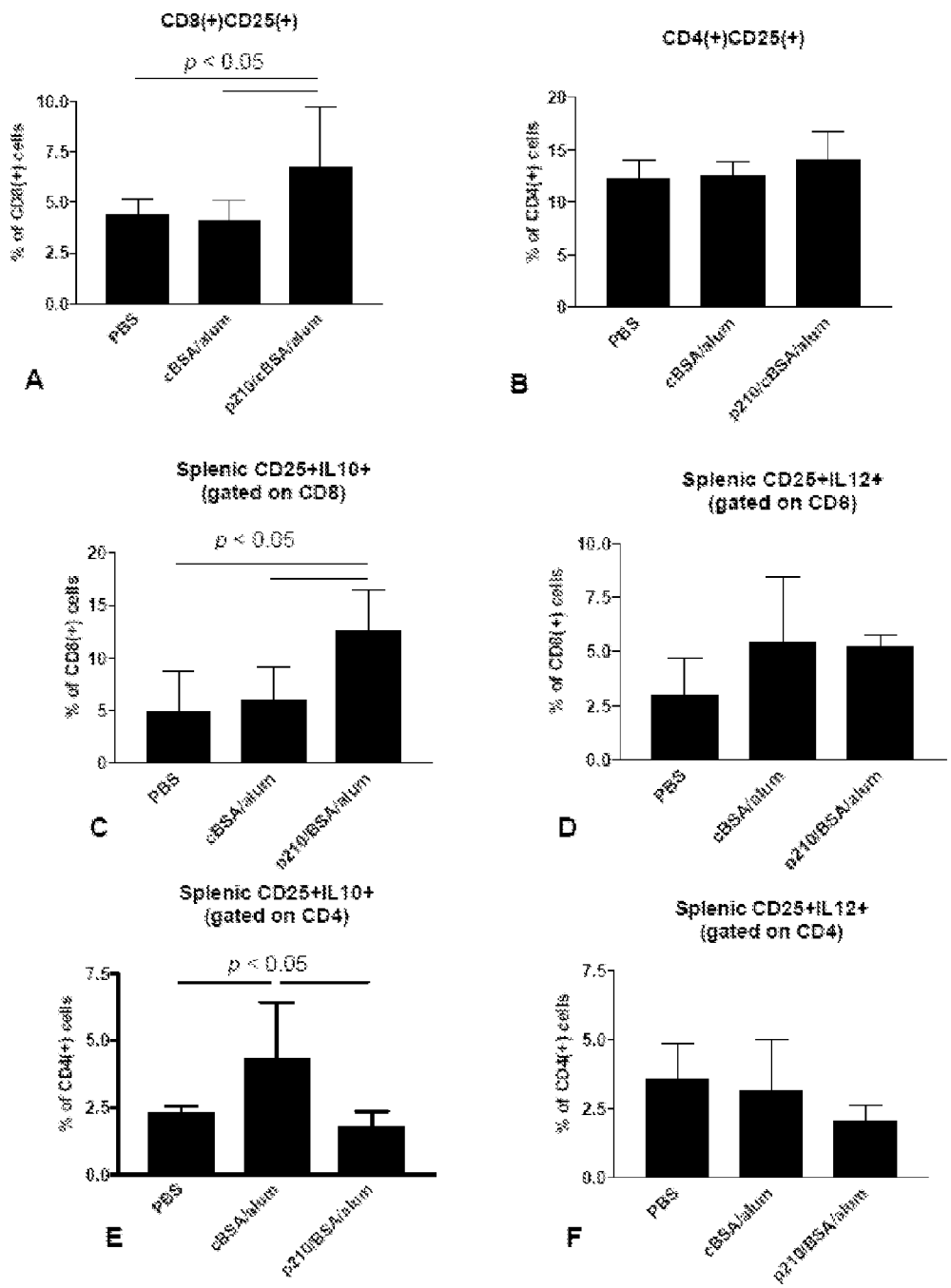
FIG. 6 shows activated lymphocyte population after immunization in vivo. (A) CD8(+)CD25(+) T-cell population in the lymph nodes was significantly higher in p210/cBSA/alum group when compared to that of PBS or cBSA/alum groups; (B) CD4(+)CD25(+) T-cells in the lymph nodes did not differ among the three groups. There was a significantly larger population of splenic CD8(+)CD25(+)IL-10(+) T-cells in p210/cBSA/alum group among 3 groups (C) without difference in splenic CD8(+)CD25(+)IL12(+) T-cells among 3 groups (D). Splenic CD4(+)CD25(+)IL-10(+) T-cell population significantly increased in the cBSA/alum group, but was significantly attenuated by the p210/cBSA/alum immunization (E) and (F) splenic CD4(+)CD25(+)IL12(+) T-cells did not differ among 3 groups. N=9-10 in each group for (A) and (B); n=5 in each group for (C), (D), (E) and (F).

There was a significantly larger population of splenic CD8 (+)CD25(+)IL-10(+) T-cells in p210/cBSA/alum group when compared to PBS or cBSA/alum groups (FIG. 6C) without difference in splenic CD8(+)CD25(+)IL12(+) T-cells among 3 groups (FIG. 6D). Splenic CD4(+)CD25(+)IL-10(+) T-cell population significantly increased in the cBSA/alum group. However, this increased response was significantly attenuated by the p210/cBSA/alum immunization (FIG. 6E); whereas splenic CD4(+)CD25(+)IL12(+) T-cells did not differ among the three groups (FIG. 6F).

Example 5

Adoptive Transfer of CD8(+) T-Cells from p210 Immunized Mice to Naive Recipients Recapitulates the Athero-Protective Effect of p210 Immunization Donor apoE(−/−) mice were subjected to the same immunization protocol with the same groupings, namely: PBS, cBSA/alum, or p210/cBSA/alum. Recipient naïve male apoE (−/−) mice were injected with donor cells at 6-7 weeks of age and were fed normal chow until 13 weeks of age when chow was switched to high cholesterol diet until euthanasia at 25 weeks of age.

Figure 7:
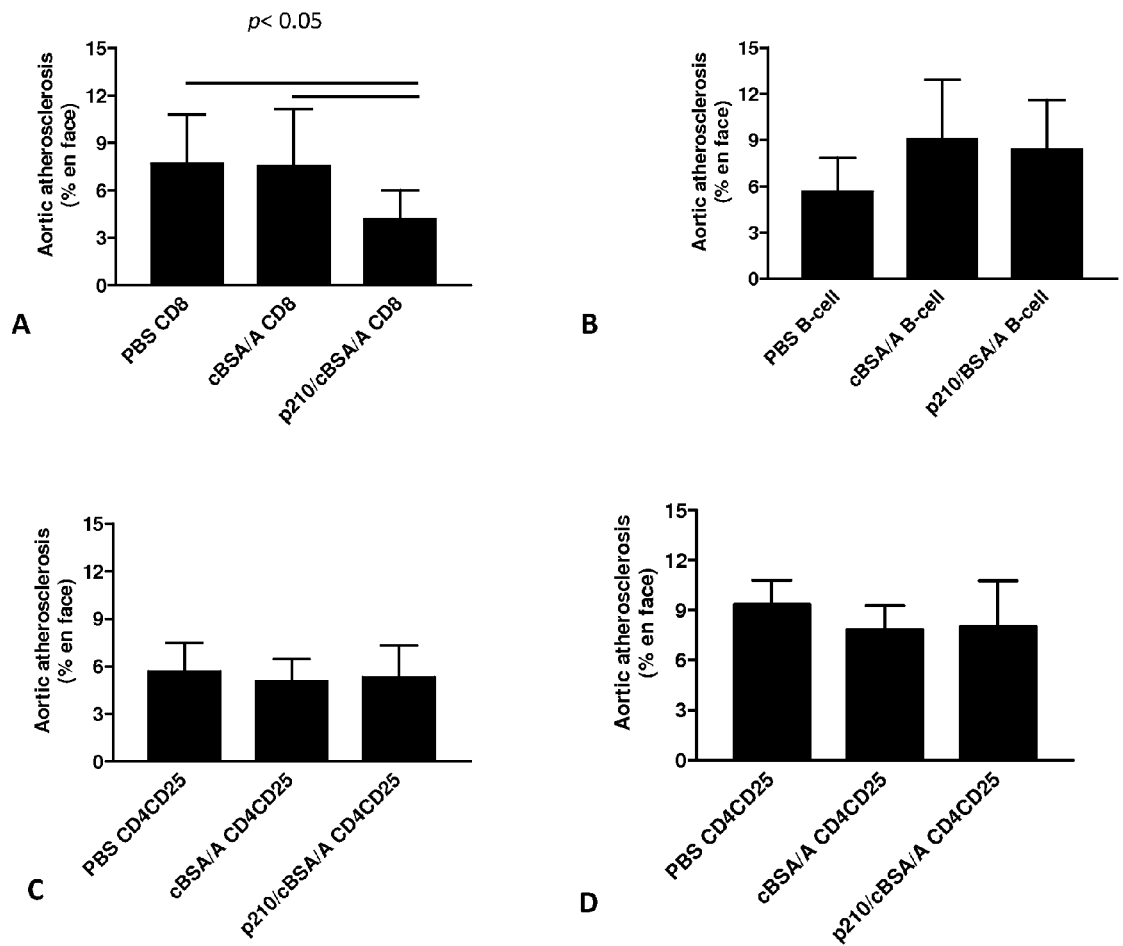
FIG. 7 shows adoptive transfer of CD8(+) T-cells from p210 immunized donors recapitulated the athero-protective effect of p210 immunization but not by transfer of B-cells or CD4(+)CD25(+) T-cells. (A) The recipient mice of CD8(+) T-cells from p210/cBSA/alum immunized donors developed significantly smaller atherosclerotic lesions compared to the recipient mice of CD8(+) T-cells from other 2 groups (n=9-10 each group). (B) Adoptive transfer of B-cells from p210/cBSA/alum donors did not reduce atherosclerosis when compared to the recipient mice of B-cells from PBS or cBSA/alum groups (n=9 each group). Recipient mice of CD4(+)CD25(+) T-cells (n=9-13 each group) with 2 different doses (C. 1×10$^5$ cells/mouse or D. 3×10$^5$ cells/mouse) did not reproduce the athero-reducing effect of p210 immunization.

At euthanasia, the recipient mice injected with CD8(+) T-cells from p210/cBSA/alum group developed significantly less atherosclerotic lesions in aorta compared to the recipient mice injected with CD8(+) T-cells from PBS or cBSA/alum groups, strongly suggesting that the effector T cell induced by the vaccine are CD8$^+$ and is mechanistically involved (FIG. 7A).

This reduction of aortic lesions was coupled with decreased splenic CD11c(+) DCs (PBS group: 4.3±1.7%; cBSA/alum group: 3.4±0.3%; p210/cBSA/alum group: 1.5±0.3%; n=5 each group, p<0.05 p210/cBSA/alum group vs. PBS or cBSA/alum group by ANOVA) with no difference in circulating levels of total cholesterol among 3 groups (PBS group: 1083±296 mg/dl; cBSA/alum group: 975±401 mg/dl; p210/cBSA/alum group: 1098±379 mg/dl).

Adoptive transfer of B cells isolated from the spleens of p210 immunized donor mice did not affect atherosclerosis in recipient mice compared to mice receiving B cells from other donors (FIG. 7B) These observations ruled out B cells as mediators of athero-protective effect of p210 immunization.

To rule out CD4(+)CD25(+) T-cells as possible athero-protective mediators induced by sub-cutaneous p210 immunization, Applicants adoptively transferred CD4(+)CD25(+) T-cells at a dose of 1×10$^5$ cells/mouse into naïve recipient apoE−/− mice. There was no difference in lesion size among the 3 groups of CD4(+)CD25(+)T-cell recipients Depletion of CD25$^+$ cells from the pool of CD8$^+$ T cells abrogated the reduction in atherosclerosis observed in the p210/cBSA/alum recipient mice, further supporting the notion that CD8$^+$CD25$^+$ T cells are mechanistically involved in the protective effects of the vaccine against atherosclerosis (FIG. 7C). Transfer of a higher number of CD4(+)CD25(+) T-cells at 3×10$^5$ cells/mouse did not reduce lesion sizes in all 3 recipient groups (FIG. 7D).

Example 6

Increased Cytolytic Activity of CD8(+) T Cells from p210 Immunized Mice Against Dendritic Cells In Vitro Given the observation that p210 immunization reduced DCs in the immunization sites and atherosclerotic plaques and adoptive transfer of CD8(+) T-cells from p210 immunized donors rendered a decrease of splenic DCs in the recipients, Applicants hypothesized that DCs could be a potential target of CD8(+) T-cells.

Figure 8:
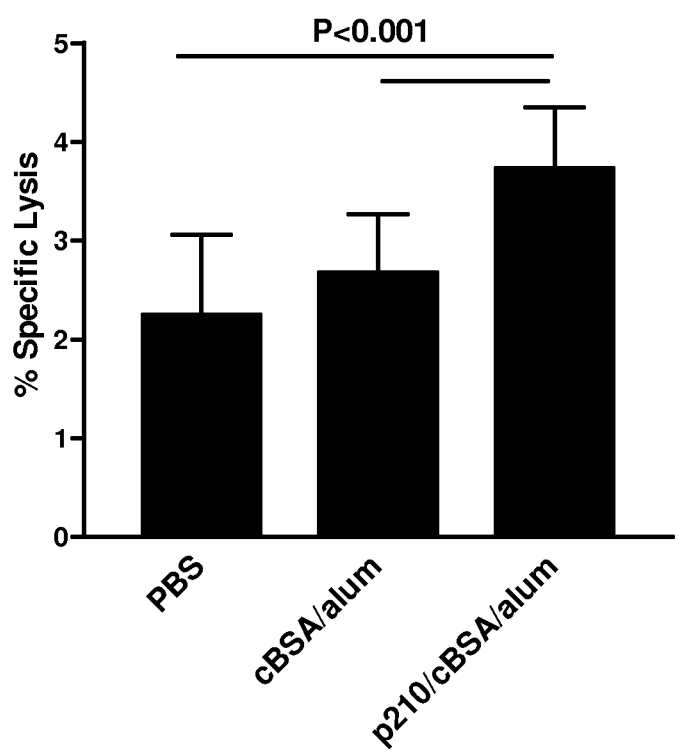
FIG. 8 shows increased cytolytic activity of CD8(+) T cells from p210 immunized mice against dendritic cells in vitro. CD8(+) T-cells from p210 immunized mice significantly had a higher cytolytic activity against dendritic cells when compared to those from PBS or BSA/alum groups. Experiments were repeated 4 times with CD8(+) T-cells pooled from 5 mice in each group each time. Duplicate or triplicate was done each time with total of 11 data-points in each group altogether.
Figure 9:
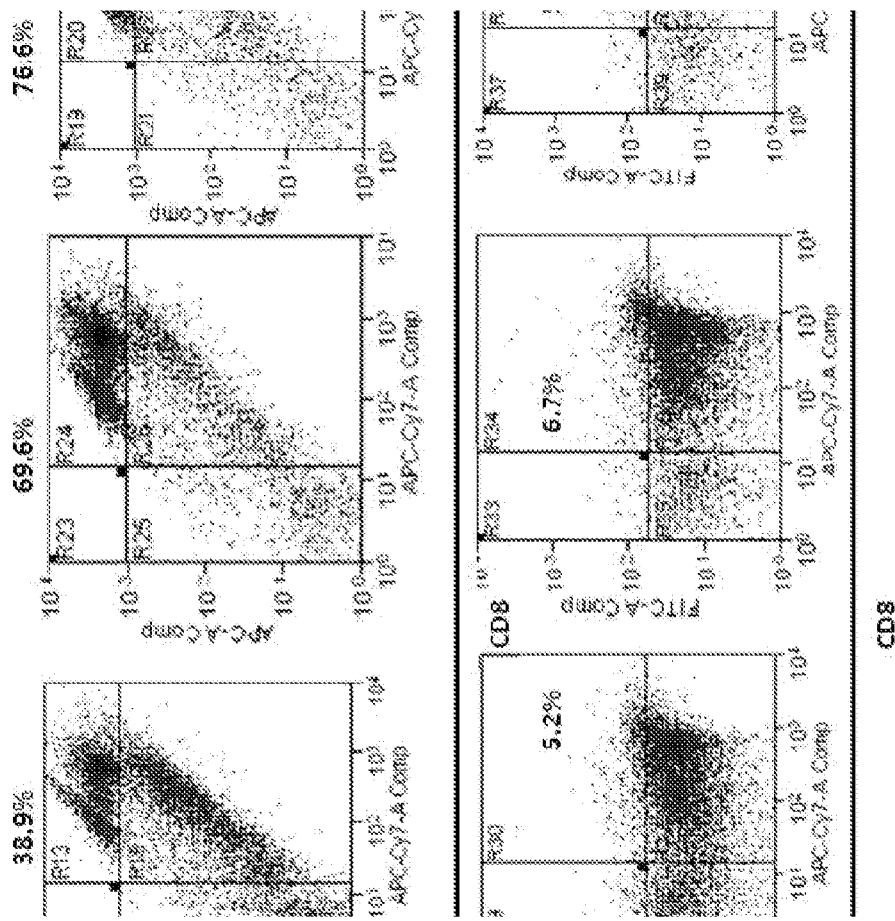
FIG. 9 shows CD8(+) T-cells from p210 immunized mice containing higher level of Granzyme B when compared to those from PBS or cBSA/alum group; whereas there is no difference in perforin level

To test this, Applicants co-cultured bone marrow derived DCs with CD8(+) T-cells from various immunized groups. CD8(+) T-cells from p210 immunized mice significantly increased the percentage of DC death when compared to those from PBS or BSA/alum groups (FIG. 8). This increased cytolytic function of CD8(+) T-cells was associated with increased granzyme B expression but not perforin (FIG. 9).

Example 7

Immunization with p210 does not Affect the Adaptive Immune Response to Other T-Cell Dependent or Independent Antigens Given the observations that p210 immunization decreased CD11c(+) DCs and reduced adaptive IgG response to p210, Applicants next tested if such modulation of DCs by p210 immunization would alter the host immune response to other antigens.

Figure 10:
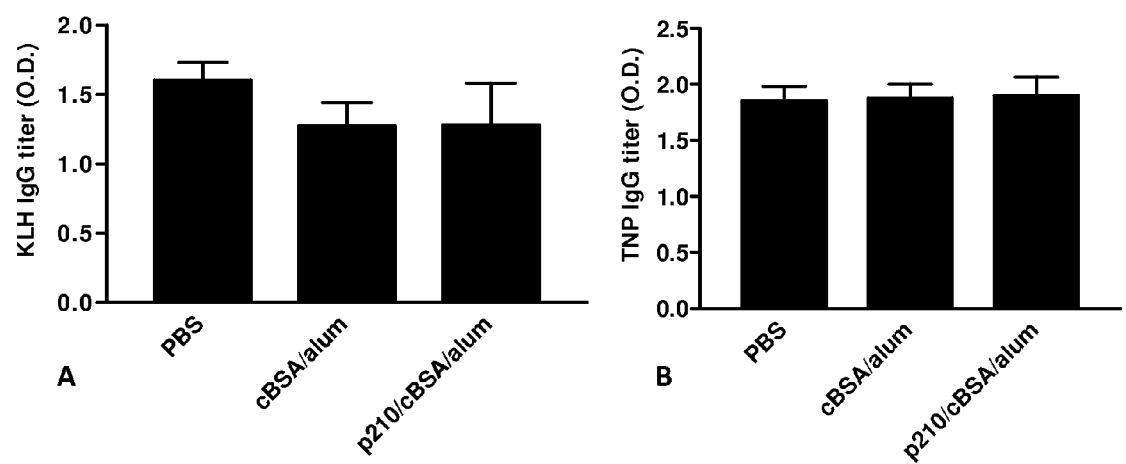
FIG. 10 shows IgG titers against KLH or TNP after p210 immunization. (A) Prior immunization with p210 did not affect the efficacy of subsequent T-cell dependent (KLH, n=3-6 each group) or (B) T-cell independent (TNP, n=4-5 each group) immunization as assessed by the IgG antibody titers when compared to mice received PBS or cBSA/alum.

Applicants first immunized mice with p210 as described in previous sections followed by two separate subcutaneous KLH immunizations or intra-peritoneal injection of TNP-LPS. Using the KLH- or TNP-IgG titer as a surrogate for the efficacy of individual immunization, Applicants found that there was no difference in KLH- or TNP-IgG titers between p210 immunized mice and the titers from mice of PBS or cBSA/alum groups (FIG. 10).

Example 8

Figure 11:
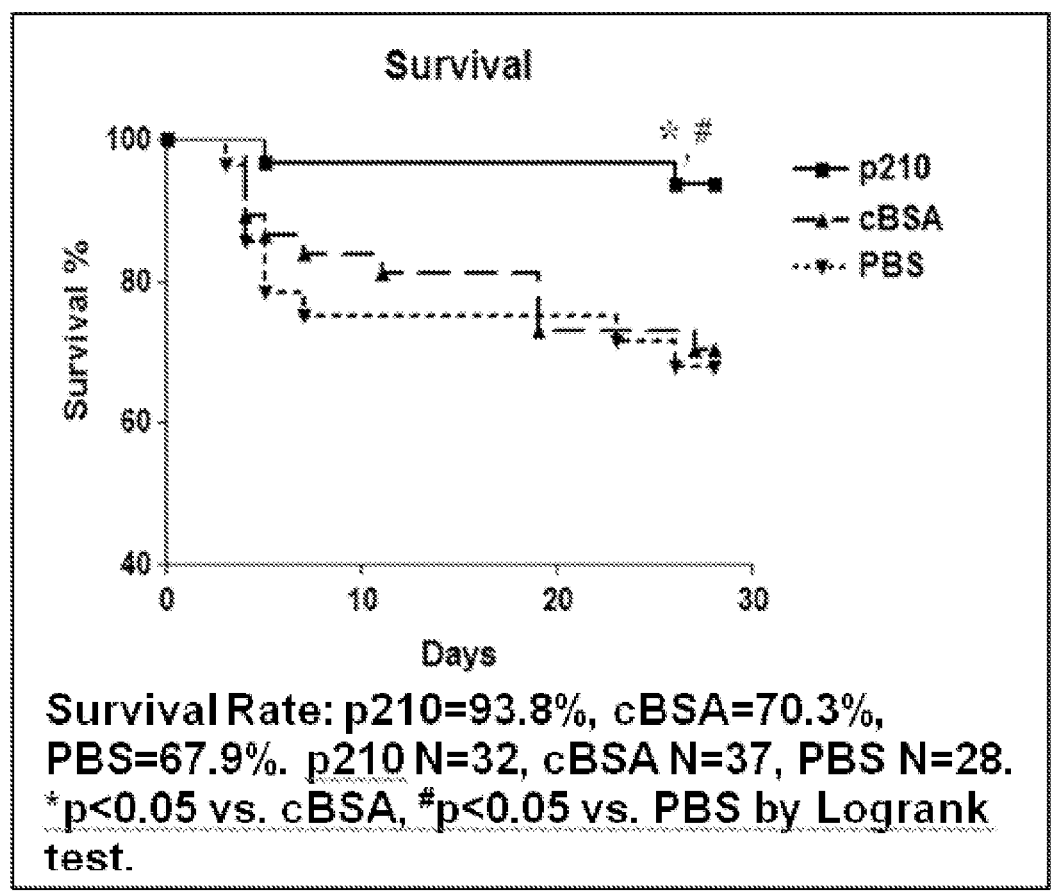
FIG. 11 shows a Kaplan Meier survival curve for mice immunized with or without p210 according to one embodiment herein described.

Immunization with an apoB-100 Immunogenic Fragments Reduces Hypertension and Mortality in Angiotensin II-Induced Aortic Aneurysm ApoE (−/−) mice were immunized with p210/cBSA/Alum (p210; 100 μg) at 7, 10, and 12 weeks of age. Mice receiving PBS or cBSA/Alum (cBSA) served as controls. At 10 weeks of age, mice were subcutaneously implanted with an osmotic pump which released AngII (1 mg/Kg/min), and were euthanized 4 weeks later. The aorta, spleen, and lymph nodes (LN) were harvested. The p210 vaccine significantly reduced mortality due to AA rupture compared to controls (see FIG. 11).

Flow cytometric analysis of dendritic cells (DCs) in LNs and spleen showed intracellular IFN-γ expression was up regulated in the p210 group. Aortic superoxide production measured by in situ dihydroethidine method and aortic AT1 receptor (AT1R) expression measured by Western blot were significantly decreased in p210 group. The p210 vaccine significantly decreased mean arterial BP at 13 weeks of age (see Table 4).

Mortality from AngII induced AA rupture was significantly reduced by thep210 vaccine. This protective effect was associated with up regulation of IFN-γ expression in DCs and decreased arterial BP, AT1R expression, and superoxide production in aorta. The vaccine may be a promising new non-invasive treatment for AA.

TABLE 4

Flow cytometric analysis of intracellular IFN-γ expression of dendritic cells (DCs)

|  | p210 | cBSA | PBS |
|---|---|---|---|
| Spleen CD11c$^+$CD86$^+$IFN-γ$^+$ DCs (N = 8 each) | 19.5 ± 1.6* | 13.9 ± 1.4 | 15.3 ± 0.7 |
| LN CD11c$^+$CD86$^+$IFN-γ$^+$ DCs (N = 6 each) | 26.7 ± 1.6* | 17.7 ± 2.3 | 18.1 ± 2.4 |
| Aortic AT1R (N = 6 each) | 1.0 ± 0.2* | 3.1 ± 0.6 | 3.2 ± 0.5 |
| Aortic superoxide production (N = 9 each) | 1.1 ± 0.1* | 1.9 ± 0.2 | 1.6 ± 0.1 |
| Mean Arterial Blood Pressure (BP) | 124 ± 4* | 143 ± 6 | 139 ± 3 |

Spleen and LN DC values are percentage ± SEM of CD11c-gated cells.
AT1R values are arbitrary densitometric unit ± SEM.
Superoxide values are arbitrary fluorescent intensity unit ± SEM.
Mean BP values are mmHg ± SEM at 13 weeks of age; number of mice: p210 N = 9; cBSA N = 7; PBS N = 10.
*$p < 0.05$ vs cBSA and PBS control; ANOVA, followed by post-hoc test.

Example 9

Increased Cytolytic Activity of CD8(+) T Cells from apoB-100 Immunogenic Fragments Immunized Mice is Specific to Lipid-Associated Antigens Applicants have shown that immunization with apoB-100 related-peptide p210 significantly reduces atherosclerosis and decreases intra-plaque CD11c$^+$ dendritic cells (DCs) in apoE-/- mice. Adoptive transfer experiments showed that athero-protection was mediated by CD8$^+$ T cells. Because apoB-100 is found on the LDL fraction of serum lipids, Applicants assessed the CD8$^+$ T cell cytolytic activity of p210 immunized mice specific to lipid-associated antigens presented by DCs.

ApoE-/- mice were immunized at 7, 9, and 12 weeks of age with p210/cBSA/alum, cBSA/alum, or PBS. One week after the third immunization, mice were euthanized to collect spleen CD8$^+$ T cells. Bone-marrow derived DCs were differentiated from naïve apoE-/- mice and used as target cells. A four-hour lytic assay was performed using a CD8-to-DC ratio of 3:1 in culture medium with 10% FBS. The cells were then collected and stained for CD11c to identify DCs and 7-AAD to assess cell lysis using flow cytometry. There was significantly more lytic activity by CD8$^+$ T cells from p210/cBSA/alum immunized mice compared to cBSA/alum and PBS (Table). When the assay was performed in media with delipidated FBS, the lytic activity specific to CD8$^+$ T cells from p210/cBSA/alum immunized mice was abrogated (Table 5), suggesting that the lipid fraction of FBS in the culture media provided a source of antigen. Loading of DCs with FITC-labeled p210 24 hours prior to the lytic assay demonstrated antigen uptake and specificity of the lytic activity of CD8$^+$ T cells from p210/cBSA/alum immunized mice (see Table 5).

These results show that the cytolytic function of CD8$^+$ T cells targeting DCs are specific to lipid-associated antigens, specifically the p210 fragment of apoB-100, and this may underlie the protective effects of p210 immunization.

TABLE 5

Flow cytometric analysis of cytolytic activity of CD8 (+) T cells.

|  | p210/cBSA/alum | cBSA/alum | PBS |
|---|---|---|---|
| Normal medium (N = 11 each) | 3.7 ± 0.6* | 2.7 ± 0.6 | 2.3 ± 0.8 |
| Delipidated medium (N = 5 each) | 2.3 ± 0.4 | 2.4 ± 0.8 | 2.5 ± 0.5 |
| FITC-p210 loaded (N = 3 each) | 10.4 ± 0.1† | 7.3 ± 0.4 | 7.8 ± 1.2 |

All flow cytometric analysis performed on CD11c-gated cells.
CD11c-gated FITC$^+$ cells only were assessed in FITC-p210 loaded assay.
Values are percent lysis relative to basal lysis.
*$P < 0.001$;
†$P < 0.01$ by ANOVA.

Example 10

Antibody Response to the p210 Vaccine

Figure 12:
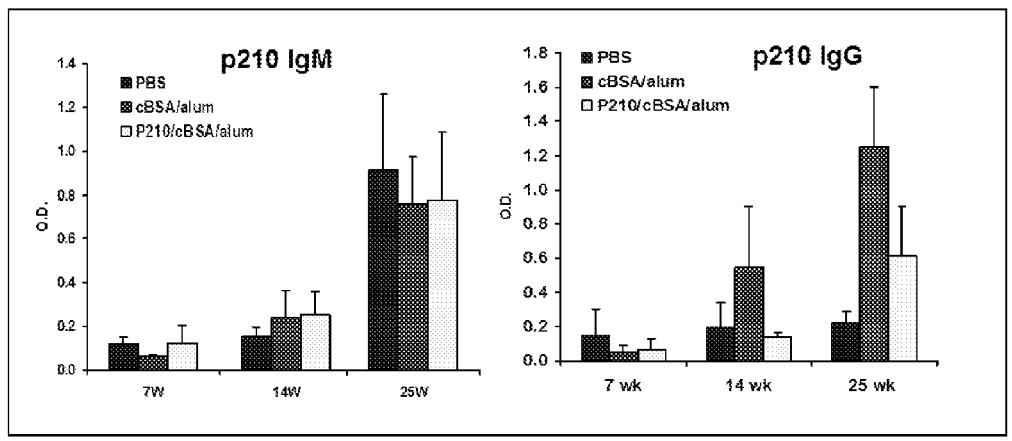
FIG. 12 shows Antibody response to p210 in apoE−/− mice according one embodiment herein described.

Antibody titers to p210 was low prior to immunization. At euthanasia at 25 weeks of age, there was a significant increase in p210 IgM titer in all groups (FIG. 12), suggesting an endogenous immune response against self-peptide p210. There was a significant increase in p210 IgG titers in both cBSA/alum group and p210/cBSA/alum compared with the PBS group, but titers in the cBSA/alum was surprisingly the higher between the 2 responding groups. The presence of alum as adjuvant in the cBSA/alum group and p210/cBSA/alum groups likely resulted in class switching of the IgM response to IgG, which did not occur in the PBS group.

Example 11

CD4 (+) T Cell and CD8 (+) T Cell Response to the p210 Vaccine

T cells from superficial cervical and axillary lymph nodes (LN) from mice one week after primary immunization were collected to assess the T cell immune response. CD4$^+$CD25$^+$ T cells in the lymph nodes (Table 1) did not differ among 3 groups. Splenic CD4$^+$CD25$^+$IL-10$^+$ T cell population significantly increased in the cBSA/alum group. However, this increased response was significantly attenuated by the p210/cBSA/alum immunization (Table 6). Interestingly, splenic CD4$^+$CD62L$^+$ T cell (Table 1) population was lower in cBSA/alum group.

One week after primary immunization, the CD8$^+$CD25$^+$ T cell population in the lymph nodes was significantly higher in p210/cBSA/alum group when compared to that of PBS or cBSA/alum groups (Table 2). There was a significantly larger population of splenic CD8$^+$CD25$^+$IL-10$^+$ T cells in p210/cBSA/alum group when compared to PBS or cBSA/alum groups (Table 2). The splenic CD8$^+$CD62L$^+$ T cell population was significantly higher in p210/cBSA/alum group when compared to that of PBS or cBSA/alum groups (Table 6). The T cell profile at other time points were not significantly different between groups.

TABLE 6

CD4 (+) and CD8 (+) T cell response to the p210 vaccine

|  | PBS | cBSA/alum | p210/cBSA/alum |
|---|---|---|---|
| CD4+ T cell response to p210 vaccine. | | | |
| LN CD4+CD25+ | 12.9 ± 1.9 | 12.5 ± 1.4 | 14.0 ± 2.8 |
| Spl CD4+CD25+IL-10+ | 2.3 ± 0.3 | 4.3 ± 2.1* | 1.7 ± 0.6 |
| Spl CD4+CD62L+ | 26.7 ± 1.7 | 21.4 ± 2.7* | 29.9 ± 4.8 |
| CD8+ T cell response to p210 vaccine. | | | |
| LN CD8+CD25+ | 4.4 ± 0.8 | 4.1 ± 1.0 | 6.8 ± 3.0* |
| Spl CD8+CD25+IL-10+ | 4.9 ± 3.9 | 6.0 ± 3.2 | 12.6 ± 3.9* |
| Spl CD8+CD62L+ | 18.4 ± 3.4 | 19.0 ± 5.5 | 27.6 ± 5.1* |

P < 0.05 vs. other groups

Example 12

Effector Role of CD8+CD25+ T Cells Involves Cytotoxic Function

The vaccine reduced DC presence in the plaques (FIG. 3), and in the spleens of p210/cBSA/alum recipient mice, suggesting that the effector role of CD8+ T cells after immunization was manifested in decreasing DCs in the plaque. Applicants therefore assessed the effect of the vaccine on cytotoxic activity of CD8+ T cells against syngeneic bone marrow-derived DCs. CD8+ T cells from the immunized groups were negatively isolated using a CD8 selection Dynabeads kit (Invitrogen) followed by co-culture with DCs in a CD8:DC ratio of 3:1 in RPMI supplemented with 10% FBS. Cells were collected and processed for flow cytometric determination of CD11c+ and 7-AAD 4 hours later.[20] Dendritic cell death without CD8+ T cells in the co-culture was used as baseline and percentage of specific lysis of cells was calculated using a method described previously.[20]

Figure 13:
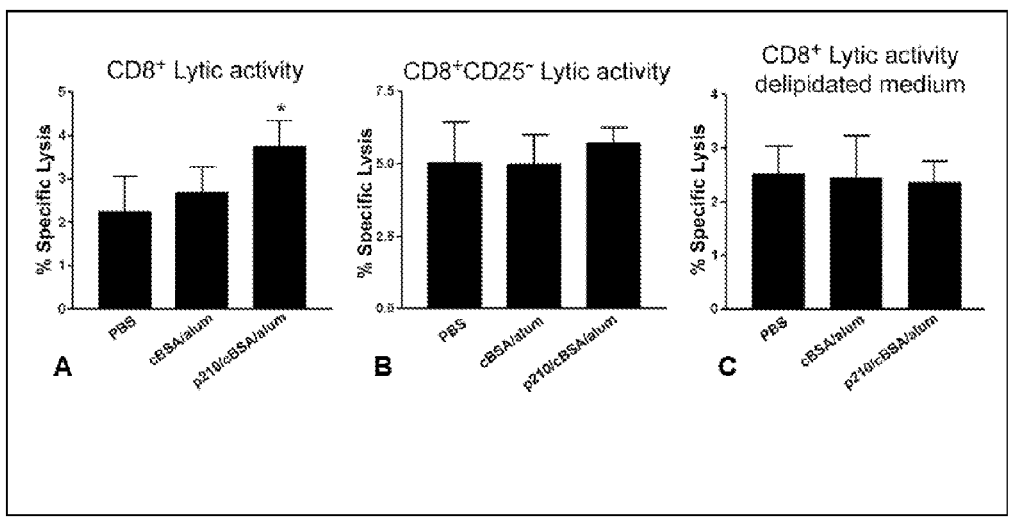
FIG. 13 shows that cytolytic activity of p210-immune CD8$^+$ T cells is abrogated by depletion of CD25$^+$ cells. Lytic activity specific to p210 is also abrogated by absence of serum lipids in the assay medium. (A) CD8$^+$ T cells from p210 immunized mice significantly increased the percentage of DC lysis when com s ared to those from PBS or cBSA/alum groups. B Depletion of CD25$^+$ cells abrogated the increased cytolytic activity specific to the CD8$^+$ T cells from p210 immunized mice. (C) The increased cytolytic function specific to CD8$^+$ T cells from p210 immunized mice was also lost with the use of delipidated serum supplemented medium.

CD8+ T cells from p210 immunized mice significantly increased the percentage of DC lysis when compared to those from PBS or cBSA/alum groups (FIG. 13, panel A). This increased cytolytic function of CD8+ T cells was associated with increased granzyme B expression but not perforin. Depletion of CD25+ cells abrogated the increased cytolytic activity specific to the CD8+ T cells from p210 immunized mice (FIG. 13, panel B) indicating that CD8+CD25+ T cells were the effector population. The increased cytolytic function specific to CD8+ T cells from p210 immunized mice was also lost with the use of delipidated serum supplemented medium (FIG. 13, panel C), indicating that the antigen on the target DCs recognized by the CTLs was derived from serum LDL containing apoB-100 in the medium.

Example 13 p210 Peptide is Endocytosed by DCs In Vitro

Figure 14:
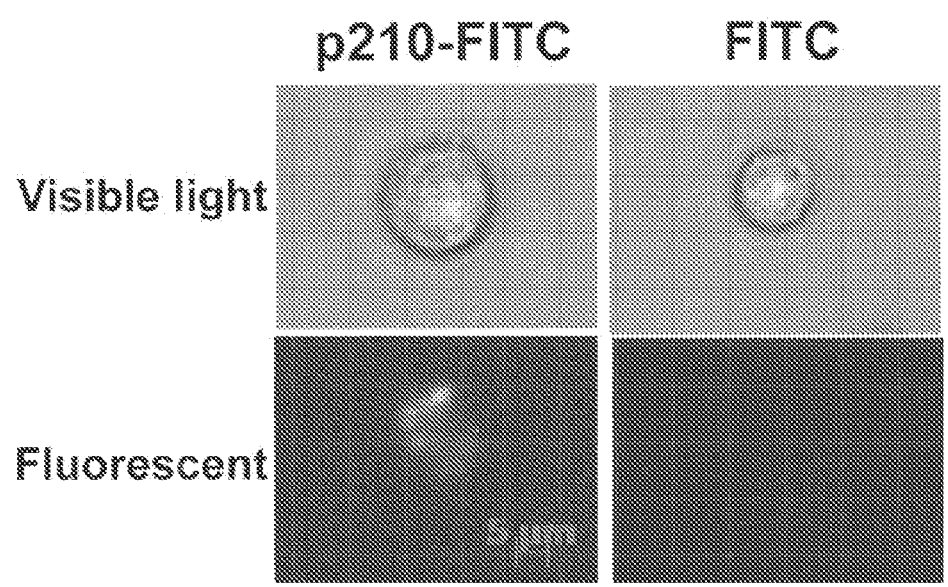
FIG. 14 shows endocytosis of FITC-labeled p210 by DCs according one embodiment herein described.

Peptide loading on BMDCs was defined using p210 labeled with FITC (FITC conjugating kit from Pierce). The presence of FITC fluorescence in the dendritic cells indicated uptake of p210 by dendritic cells. Reference is made in particular to FIG. 14 which shows the FITC-labeled p210 is endocytosed by DCs, indicating antigen uptake.

Example 14 p210 Peptide is Presented by DCs to CD8+ T Cells

Figure 15:
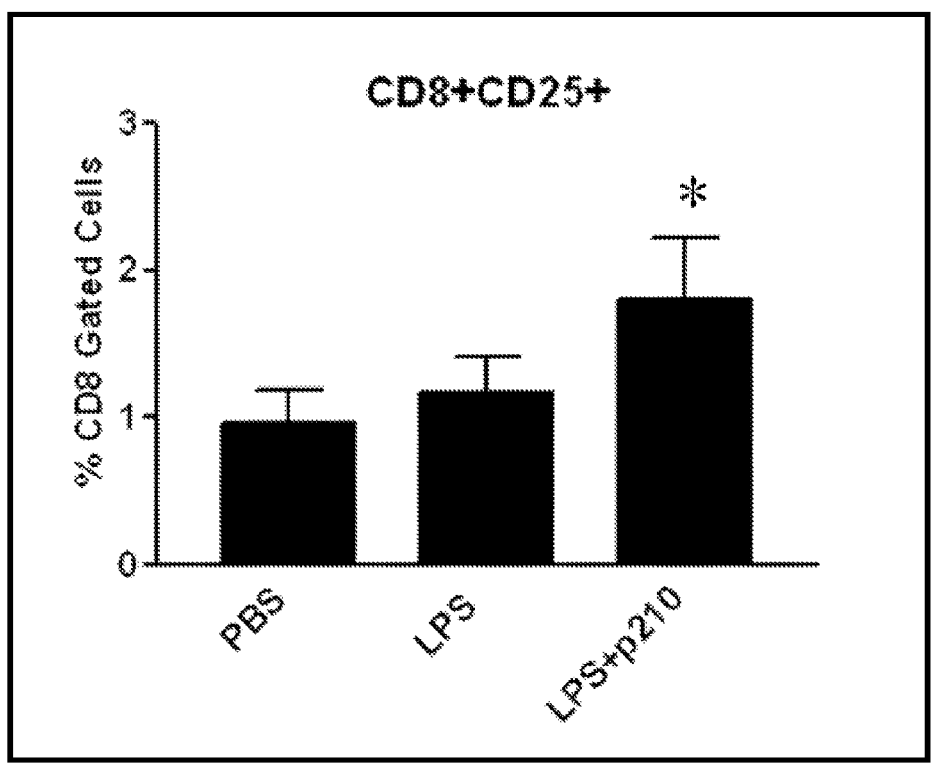
FIG. 15 shows presentation of the peptide p210 by DCs to CD8$^+$CD25$^−$ T cells in vitro as shown by increased activated CD25+ cells according one embodiment herein described.

The p210 peptide contains the proteoglycan binding site of the apoB-100 molecule. This peptide is a cell-penetrating peptide capable of efficiently delivering antigens for cross-presentation to cytotoxic CD8+ T cells.[53] Applicants therefore assessed activation of CD8+CD25− T cells co-cultured with DCs loaded with p210 and matured with LPS. There was significantly increased CD8+CD25+ T cells 48 hours after co-culture with p210-loaded DCs treated with LPS compared to untreated, or LPS only treated co-cultures (FIG. 15). The results suggest that the p210 antigen is presented by DCs to CD8+ T cells.

Example 15 p210-Loaded DCs are Specifically Targeted by Immune CD8+ T Cells

Figure 16:
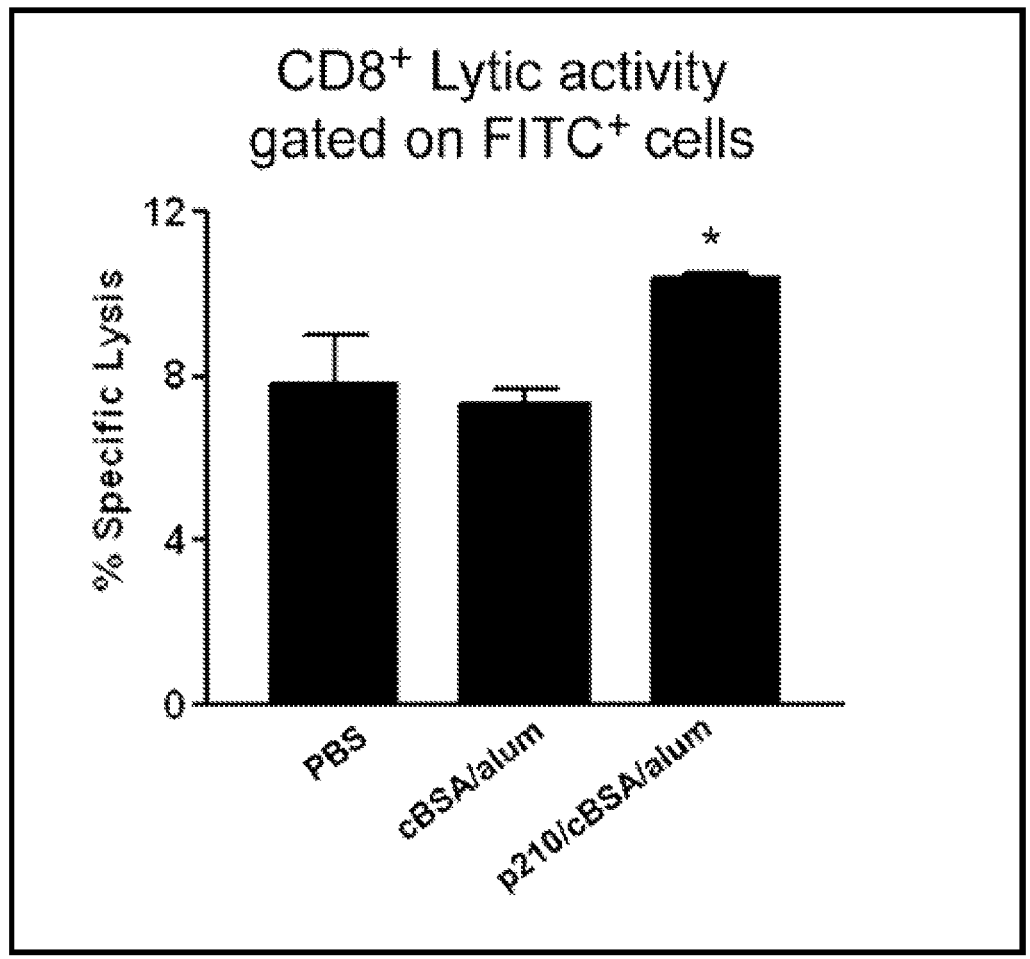
FIG. 16 shows CD8$^+$ lytic activity gated on FITC cells according an embodiment herein described. p210-specific lytic activity by CD8$^+$ T cells from p210-vaccinated mice using DCs loaded with FITC-labeled p210.

The results shown above in Example 14 support the notion that p210 is presented by DCs to CD8+ T cells. It remained unclear if the lytic activity against DCs was specific to the p210 antigen. Applicants therefore repeated the lytic assay using FITC-labeled p210 loaded BMDC as targets. Lytic activity against FITC DCs was significantly increased in CD8+ T cells from the p210/cBSA/alum mice (FIG. 16), indicating antigen specific lytic activity.

In summary, in several embodiments, described herein are immunomodulatory agents, T cell, compositions, methods and systems for treating and/or preventing hypertension and/or a condition associated thereto in an individual The examples set forth above are provided to give those of ordinary skill in the art a complete disclosure and description of how to make and use the embodiments of the molecules, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the sequence listing submitted herewith in the txt file "P694-PCT-2011-11-11-Sequence Listing_ST25" created on Nov. 11, 2011, forms an integral part of the present application and is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Shah, P. K., K. Y. Chyu, G. N. Fredrikson, and J. Nilsson. 2005. Immunomodulation of atherosclerosis with a vaccine. *Nat. Clin. Pract. Cardiovasc. Med.* 2:639-646
2. Hansson, G. K., P. Libby, U. Schonbeck, and Z. Q. Yan. 2002. Innate and adaptive immunity in the pathogenesis of atherosclerosis. *Circ. Res.* 91:281-291
3. Chyu, K. Y., X. Zhao, 0. S. Reyes, S. M. Babbidge, P. C. Dimayuga, J. Yano, B. Cercek, G. N. Fredrikson, J. Nilsson, and P. K. Shah. 2005. Immunization using an Apo B-100 related epitope reduces atherosclerosis and plaque inflammation in hypercholesterolemic apo E (−/−) mice. *Biochem. Biophys. Res. Commun.* 338:1982-1989
4. Fredrikson, G. N., I. Soderberg, M. Lindholm, P. Dimayuga, K. Y. Chyu, P. K. Shah, and J. Nilsson. 2003. Inhibition of Atherosclerosis in ApoE-Null Mice by Immunization with ApoB-100 Peptide Sequences. *Arterioscler. Thromb. Vasc. Biol.* 23:879-884
5. Fredrikson, G. N., L. Andersson, I. Soderberg, P. Dimayuga, K. Y. Chyu, P. K. Shah, and J. Nilsson. 2005. Atheroprotective immunization with MDA-modified apo B-100 peptide sequences is associated with activation of Th2 specific antibody expression. *Autoimmunity* 38:171-179
6. Fredrikson, G. N., H. Bjorkbacka, I. Soderberg, I. Ljungcrantz, and J. Nilsson. 2008. Treatment with apo B peptide vaccines inhibits atherosclerosis in human apo B-100 transgenic mice without inducing an increase in peptide-specific antibodies. *J. Intern. Med.* 1-8
7. Klingenberg, R., M. Lebens, A. Hermansson, G. N. Fredrikson, D. Strodthoff, M. Rudling, D. F. Ketelhuth, N. Gerdes, J. Holmgren, J. Nilsson, and G. K. Hansson. 2010. Intranasal Immunization With an Apolipoprotein B-100 Fusion Protein Induces Antigen-Specific Regulatory T Cells and Reduces Atherosclerosis. *Arterioscler. Thromb. Vasc. Biol.* 30:946-952
8. Fredrikson, G. N., B. Hedblad, G. Berglund, R. Alm, M. Ares, B. Cercek, K. Y. Chyu, P. K. Shah, and J. Nilsson. 2003. Identification of Immune Responses Against Aldehyde-Modified Peptide Sequences in ApoB Associated With Cardiovascular Disease. *Arterioscler. Thromb. Vasc. Biol.* 23:872-878
9. Schiopu, A., J. Bengtsson, I. Soderberg, S. Janciauskiene, S. Lindgren, M. P. Ares, P. K. Shah, R. Carlsson, J. Nilsson, and G. N. Fredrikson. 2004. Recombinant Human Antibodies Against Aldehyde-Modified Apolipoprotein B-100 Peptide Sequences Inhibit Atherosclerosis. *Circulation* 2004. 110:2047-2052
10. Sjogren, P., G. N. Fredrikson, A. Samnegard, C. G. Ericsson, J. Ohrvik, R. M. Fisher, J. Nilsson, and A. Hamsten. 2008. High plasma concentrations of autoantibodies against native peptide 210 of apoB-100 are related to less coronary atherosclerosis and lower risk of myocardial infarction. *Eur. Heart J.* 29:2218-2226
11. Dimayuga, P., B. Cercek, S. Oguchi, G. N. Fredrikson, J. Yano, P. K. Shah, S. Jovinge, and J. Nilsson. 2002. Inhibitory effect on arterial injury-induced neointimal formation by adoptive B-cell transfer in Rag-1 knockout mice. *Arterioscler. Thromb. Vasc. Biol.* 22:644-649
12. Caligiuri, G., A. Nicoletti, B. Poirier, and G. K. Hansson. 2002. Protective immunity against atherosclerosis carried by B cells of hypercholesterolemic mice. *J. Clin. Invest.* 109:745-753
13. Yang, K., D. Li, M. Luo, and Y. Hu. 2006. Generation of HSP60-specific regulatory T cell and effect on atherosclerosis. *Cell Immunol.* 243:90-95
14. Mor, A., D. Planer, G. Luboshits, A. Afek, S. Metzger, T. Chajek-Shaul, G. Keren, and J. George. 2007. Role of naturally occurring CD4+ CD25+ regulatory T cells in experimental atherosclerosis. *Arterioscler. Thromb. Vasc. Biol.* 27:893-900
15. Ait-Oufella, H., B. L. Salomon, S. Potteaux, A. K. Robertson, P. Gourdy, J. Zoll, R. Merval, B. Esposito, J. L. Cohen, S. Fisson, R. A. Flavell, G. K. Hansson, D. Klatzmann, A. Tedgui, and Z. Mallat. 2006. Natural regulatory T cells control the development of atherosclerosis in mice. *Nat. Med.* 12:178-180
16. Yang, G. X., Z. X. Lian, Y. H. Chuang, Y. Moritoki, R. Y. Lan, K. Wakabayashi, A. A. Ansari, R. A. Flavell, W. M. Ridgway, R. L. Coppel, K. Tsuneyama, I. R. Mackay, and M. E. Gershwin. 2008. Adoptive transfer of CD8(+) T cells from transforming growth factor beta receptor type II (dominant negative form) induces autoimmune cholangitis in mice. *Hepatology.* 47:1974-1982

17. Zhou, X., A. Nicoletti, R. Elhage, and G. K. Hansson. 2000. Transfer of CD4(+) T cells aggravates atherosclerosis in immunodeficient apolipoprotein E knockout mice. *Circulation* 102:2919-2922

18. Zhou, X., A. K. Robertson, C. Hjerpe, and G. K. Hansson. 2006. Adoptive transfer of CD4+ T cells reactive to modified low-density lipoprotein aggravates atherosclerosis. *Arterioscler. Thromb. Vasc. Biol.* 26:864-870

19. Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte/macrophage colony-stimulating factor. *J. Exp. Med.* 176: 1693-1702

20. Lecoeur, H., M. Fevrier, S. Garcia, Y. Riviere, and M. L. Gougeon. 2001. A novel flow cytometric assay for quantitation and multiparametric characterization of cell-mediated cytotoxicity. *J. Immunol. Methods* 253:177-187

21. Palinski, W., E. Miller, and J. L. Witztum. 1995. Immunization of low density lipoprotein (LDL) receptor-deficient rabbits with homologous malondialdehyde-modified LDL reduces atherogenesis. *Proc. Natl. Acad. Sci. U.S. A* 92:821-825

22. Ameli, S., A. Hultgardh-Nilsson, J. Regnstrom, F. Calara, J. Yano, B. Cercek, P. K. Shah, and J. Nilsson. 1996. Effect of immunization with homologous LDL and oxidized LDL on early atherosclerosis in hypercholesterolemic rabbits. *Arterioscler. Thromb. Vasc. Biol.* 16:1074-1079

23. Freigang, S., S. Horkko, E. Miller, J. L. Witztum, and W. Palinski. 1998. Immunization of LDL receptor-deficient mice with homologous malondialdehyde-modified and native LDL reduces progression of atherosclerosis by mechanisms other than induction of high titers of antibodies to oxidative neoepitopes. *Arterioscler. Thromb. Vasc. Biol.* 18:1972-1982

24. George, J., A. Afek, B. Gilburd, H. Levkovitz, A. Shaish, I. Goldberg, Y. Kopolovic, G. Wick, Y. Shoenfeld, and D. Harats. 1998. Hyperimmunization of apo-E-deficient mice with homologous malondialdehyde low-density lipoprotein suppresses early atherogenesis. *Atherosclerosis* 138: 147-152

25. Zhou, X., G. Caligiuri, A. Hamsten, A. K. Lefvert, and G. K. Hansson. 2001. LDL immunization induces T-cell-dependent antibody formation and protection against atherosclerosis. *Arterioscler. Thromb. Vasc. Biol.* 21:108-114

26. Chyu, K. Y., 0. S. Reyes, X. Zhao, J. Yano, P. Dimayuga, J. Nilsson, B. Cercek, and P. K. Shah. 2004. Timing affects the efficacy of LDL immunization on atherosclerotic lesions in apo E (−/−) mice. *Atherosclerosis* 176:27-35

27. Zhou, X., A. K. Robertson, M. Rudling, P. Parini, and G. K. Hansson. 2005. Lesion development and response to immunization reveal a complex role for CD4 in atherosclerosis. *Circ. Res.* 96:427-434

28. Roselaar, S. E., P. X. Kakkanathu, and A. Daugherty. 1996. Lymphocyte populations in atherosclerotic lesions of apoE −/− and LDL receptor −/− mice. Decreasing density with disease progression. *Arterioscler. Thromb. Vasc. Biol.* 16:1013-1018

29. Zhou, X., S. Stemme, and G. K. Hansson. 1996. Evidence for a local immune response in atherosclerosis. CD4+ T cells infiltrate lesions of apolipoprotein-E-deficient mice. *Am. J. Pathol.* 149:359-366

30. Fyfe, A. I., J. H. Qiao, and A. J. Lusis. 1994. Immune-deficient mice develop typical atherosclerotic fatty streaks when fed an atherogenic diet. *J. Clin. Invest.* 94:2516-2520

31. Bobryshev, Y. V., T. Taksir, R. S. Lord, and M. W. Freeman. 2001. Evidence that dendritic cells infiltrate atherosclerotic lesions in apolipoprotein E-deficient mice. *Histol. Histopathol.* 16:801-808

32. Niessner, A., and C. M. Weyand. 2009. Dendritic cells in atherosclerotic disease. *Clin. Immunol.* 134:25-32

33. Paulson, K. E., S. N. Zhu, M. Chen, S. Nurmohamed, J. Jongstra-Bilen, and M. I. Cybulsky. 2010. Resident intimal dendritic cells accumulate lipid and contribute to the initiation of atherosclerosis. *Circ. Res.* 106:383-390

34. Liu, P., Y. R. Yu, J. A. Spencer, A. E. Johnson, C. T. Vallanat, A. M. Fong, C. Patterson, and D. D. Patel. 2008. CX3CR1 deficiency impairs dendritic cell accumulation in arterial intima and reduces atherosclerotic burden. *Arterioscler. Thromb. Vasc. Biol.* 28:243-250

35. Wu, H., R. M. Gower, H. Wang, X. Y. Perrard, R. Ma, D. C. Bullard, A. R. Burns, A. Paul, C. W. Smith, S. I. Simon, and C. M. Ballantyne. 2009. Functional role of CD11c+ monocytes in atherogenesis associated with hypercholesterolemia. *Circulation.* 119:2708-2717

36. Sakamoto, N., K. Tsuji, L. M. Muul, A. M. Lawler, E. F. Petricoin, F. Candotti, J. A. Metcalf, J. A. Tavel, H. C. Lane, W. J. Urba, B. A. Fox, A. Varki, J. K. Lunney, and A. S. Rosenberg. 2007. Bovine apolipoprotein B-100 is a dominant immunogen in therapeutic cell populations cultured in fetal calf serum in mice and humans. *Blood* 110:501-508

37. van den Elzen, p., S. Garg, L. Leon, M. Brigl, E. A. Leadbetter, J. E. Gumperz, C. C. Dascher, T. Y. Cheng, F. M. Sacks, P. A. Illarionov, G. S. Besra, S. C. Kent, D. B. Moody, and M. B. Brenner. 2005. Apolipoprotein-mediated pathways of lipid antigen presentation. *Nature* 437: 906-910

38. Mitchell D M, Ravkov E V, Williams M A Distinct roles for IL-2 and IL-15 in the differentiation and survival of CD8+ effector and memory T cells. J. Immunol. 2010 Jun. 15; 184(12):6719-30. Epub 2010 May 14

39. Perret R, Ronchese F. Effector CD8+ T cells activated in vitro confer immediate and long-term tumor protection in vivo. Eur J. Immunol. 2008 October; 38(10):2886-95.

40. Kamimura D, Bevan M J. Naive CD8+ T cells differentiate into protective memory-like cells after IL-2 anti IL-2 complex treatment in vivo. J Exp Med. 2007 Aug. 6; 204 (8):1803-12. Epub 2007 Jul. 30.

41. J. Immunol. 2006; 177:5868-5877

42. J. Immunol. 2004; 172:1991-1995

43. San-Hwan Chen et al The complete cDNA and amino acid sequence of Human Apolipoprotein B100 Journal of Biological Chemistry 1986 Vol. 261 No 28, Issue of October 5, 12918-12921

44. Chou P Y, Fasman G O, Adv Enzymol Relat Areas Mol BioI. 1978; 47: 45-148. Prediction of the secondary structure of proteins from their amino acid sequence;

45. Margalit H, Spouge J L, Cornette J L, Cease K B, Delisi C, Berzofsky J A, J., Immunol. 1987 Apr. 1; 138(7):2213-29. Prediction of immunodominant helper T cell antigenic sites from the primary sequence;

46. Jameson B A, Wolf H., Division of Biology, California Institute of Technology, Pasadena, Calif. 91125, Comput Appl BioscL 1988 March; 4(1): 181-6. The antigenic index: a novel algorithm for predicting antigenic determinants;

47. Reyes V E, Lew R A, Lu S., Humphreys R E, Methods Enzymol. 1991; 202:22538. Prediction of alpha helices and T cell-presented sequences in proteins with algorithms based on strip-of-helix hydrophobicity index (SOHHI);
48. Maksyutov A Z, Zagrebelnaya E S, Comput Appl BioscL 1993 June; 9(3): 291-7. ADEPT: a computer program for prediction of protein antigenic determinants;
49. Pellequer J L, Westhof E., J Mol Graph. 1993 September; 11(3): 204-10, 1912. PREDITOP: a program for antigenicity prediction;
50. Lu et al., Tibtech, vol. 9, July 1991 pp. 238-242 Common Principles in Protein Folding and Antigen Protection; and
51. Laura Raddrizzani and Juergen Hammer BRIEFINGS IN BIOINFORMATICS. VOL I. NO 2. 179-189. MAY 2000 Epitope scanning using virtual Matrix-based algorithms
52. R. Wu, R. Giscombe, G. Holm & A. K. Lefvert "Induction of Human Cytotoxic T Lymphocytes by Oxidized Low Density Lipoproteins" Scand. J. Immunol. 43,381-384, 1996.
53. Sakamoto, N and Rosenberg, A S. Apolipoprotein B binding domains: evidence that they are cell-penetrating peptides that efficiently deliver antigenic peptide for cross-presentation of cytotoxic T cells. J. Immunol. 4-15-2011; 186:5004-5011.

What is claimed is:

1. A method to treat hypertension in an individual, the method comprising:
   administering to the individual an effective amount of an immunogenic fragments of Apolipoprotein B-100 (ApoB-100);
   wherein said immunogenic fragment comprises the amino acid set forth in SEQ ID NO: 210, so as to treat hypertension in the individual.

2. The method of claim 1, wherein the individual is a human and the effective amount is less than 1 mg.

3. The method of claim 1, wherein the effective amount is administered between 1 and 3 times.

4. A method to treat hypertension in an individual, the method comprising:
   administering to the individual an effective amount of activated CD8(+) T cells specific for an immunogenic fragment of Apolipoprotein B-100 (ApoB-100),
   wherein the immunogenic fragment comprises the amino acid set forth in SEQ ID NO: 210, so as to treat hypertension in the individual.

5. The method claim 4, wherein the effective amount is between 500,000 and 2,000,000 CD8(+) T cells.

6. The method of claim 4, wherein the administering is performed by administering 1,000,000 CD8(+) T cells to the individual.

7. The method of claim 4, wherein the method further comprises administering an effective amount of one or more enhancer of CD8(+) T cells selected from interleukin-10 (IL-10), interleukin-2 (IL-2), interleukin-12 (IL-12), interleukin-4 (IL-4), interleukin-16 (IL-16), interleukin-15 (IL-15), transforming growth factor beta (TGF-beta), and IL-2-antiIL2 antibody complex.

8. The method of claim 4, wherein the activated CD8(+) T cells specific for the immunogenic fragment of Apolipoprotein B-100 (ApoB-100) are obtainable by contacting CD8(+) T cells with the amino acid set forth in SEQ ID NO: 210 for a time and under conditions to activate the CD8(+) T cells, wherein the activated CD8(+) T cells are specific for the amino acid set forth in SE. ID NO: 210.

* * * * *